US006787346B2

(12) United States Patent
Chen

(10) Patent No.: US 6,787,346 B2
(45) Date of Patent: Sep. 7, 2004

(54) KINASE CAPABLE OF SITE-SPECIFIC PHOSPHORYLATION OF IκBα

(75) Inventor: Zhijian J. Chen, Dallas, TX (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 8 days.

(21) Appl. No.: 10/052,005

(22) Filed: Jan. 17, 2002

(65) Prior Publication Data

US 2002/0151022 A1 Oct. 17, 2002

Related U.S. Application Data

(63) Continuation of application No. 09/406,293, filed on Sep. 24, 1999, now abandoned, which is a division of application No. 08/825,559, filed on Mar. 19, 1997, now Pat. No. 6,107,073, which is a continuation-in-part of application No. 08/616,499, filed on Mar. 19, 1996, now abandoned.

(51) Int. Cl.$^7$ ................................................ C12N 9/12
(52) U.S. Cl. ...................................................... 435/194
(58) Field of Search ......................................... 435/194

(56) References Cited

U.S. PATENT DOCUMENTS

| 5,830,756 | A | 11/1998 | Haskill et al. | |
|---|---|---|---|---|
| 5,972,674 | A | 10/1999 | Mercurio et al. | ........... 435/194 |
| 6,242,253 | B1 | 6/2001 | Karin et al. | ................ 435/325 |
| 6,258,579 | B1 | 7/2001 | Mercurio et al. | ........... 435/194 |
| 6,268,194 | B1 | 7/2001 | Karin et al. | ................ 435/194 |
| 6,576,437 | B2 | 6/2003 | Mercurio et al. | |

FOREIGN PATENT DOCUMENTS

| WO | 98/08955 | 3/1998 |
|---|---|---|
| WO | 98/37228 | 8/1998 |

OTHER PUBLICATIONS

Amason, T. and Ellison, M.J., "Stress resistance in *Saccharomyces cerevisiae* is strongly correlated with assembly of a novel type of multiubiquitin chain", Molecular and Cell Biology, vol. 14, No. 12, pp. 7876–7883 (1994).
Auphan, N., et al., "Immunosuppression by Glucocorticoids: Inhibition of NF–kB Activity Through Induction of IkB Synthesis" Science, vol. 270, pp. 286–290 (1995).
Baeuerle, P. and Henkel, T., "Function and Activation of NF–kB in the Immune System", Annual Review of Immunology, vol. 12, pp. 141–179 (1994).
Blank, J., et al., "Molecular Cloning of Mitogen–activated Protein/ERK Kinase Kinases (MEKK) 2 and 3", The Journal of Biological Chemistry, vol. 271, No. 10, pp. 5361–5368 (1996).
Chen, P., et al., "Multiple Ubiquitin–Conjugating Enzymes Participate in the In Vivo Degradation of the Yeast MATα2 Repressor", Cell, vol. 74, pp. 357–369 (1993).

Chen, Z., et al., "A 25–Kilodalton Ubiquitin Carrier Protein (E2) Catalyzes Multiubiquitin Chain Synthesis via Lysine 48 of Ubiquitin", The Journal of Biological Chemistry, vol. 265, No. 35, pp. 21835–21842 (1990).
Choi, K., et al., "Ste5 Tethers Multiple Protein Kinases in the MAP Kinase Cascade Required for Mating in *S. cerevisiae*", Cell, vol. 78, pp. 499–512 (1994).
Derijard, B., et al., "Independent Human MAP Kinase Signal Transduction Pathways Defined by MEK and MKK Isoforms" Science, vol. 267, pp. 682–685 (1995).
Derijard, B., et al., "JNK1: A Protein Kinase Stimulated by UV Light and Ha–RAS That Binds and Phosphorylates the c–Jun Activation Domain", Cell, vol. 76, pp. 1025–1037 (1994).
DiDonato, J., et al., "Phosphorylation of IkBα Precedes but is Not Sufficient for Its Dissociation from NF–kB", Molecular and Cellular Biology, vol. 15, No. 3, pp. 1302–1311 (1995).
Finco, T., et al., "Inducible phosphorlation of IkBα is not sufficient for its dissociation from NF–kB and is inhibited by protease inhibitors", Proceedings of the National Academy of Sciences USA, vol. 91, pp. 11884–11888 (1994).
Finco, T., et al., "Mechanistic Aspects of NF–kB Regulation: The Emerging Role of Phosphorylation and Proteolysis", Immunity, vol. 3, pp. 263–272 (1995).
Francis, S. and Corbin, D., "Structure and Function of Cyclic Nucleotide–Dependent Protein Kinases" Annual Review of Physiology, vol. 56, pp. 237–272 (1994).
Goldberg, A., "Functions of the Proteasome: The Lysis at the End of the Tunnel", Science, vol. 268, pp. 522–523 (1995).
Gupta, S., et al., "Transcription Factor ATF2 Regulation by the JNK Signal Transduction Pathway", Science, vol. 267, pp. 389–393 (1995).
Haskill, S., et al., "Characterization of an Immediate–Early Gene Induced in Adherent Monocytes That Encodes IkB–like Activity", Cell, vol. 65, pp. 1281–1289 (1991).

(List continued on next page.)

*Primary Examiner*—Charles L. Patterson, Jr.
(74) *Attorney, Agent, or Firm*—Millennium Pharmaceuticals, Inc.

(57) ABSTRACT

The present invention relates, in general, to a kinase which in its activated state is capable of site-specific phosphorylation of IκBα, IκBα kinase. In particular, the present invention relates to the purified kinase, antibodies having binding affinity specifically to the kinase, and hybridomas containing the antibodies. This invention further relates to bioassays using protein or antibodies of this invention to diagnose, assess, or prognose a mammal afflicted with an undesired activation of NF-κB. This invention also relates to ligands, agonists, and antagonists of the kinase, and diagnostic and therapeutic uses thereof. This invention also relates to bioassays using the kinase to identify ligands, agonists, and antagonists. More specifically, this invention relates to selective inhibitors of the kinase.

6 Claims, 32 Drawing Sheets

OTHER PUBLICATIONS

Hershko, A. and Heller, H., "Occurrence of a Polyubiquitin Structure in Ubiquitin–Protein Conjugates", Biochemical and Biophysical Research Communications, vol. 128, No. 3, pp. 1079–1086 (1985).

Hibi, M., et al., "Identification of an oncoprotein– and UV–responsive protein kinase that binds and potentiates the c–Jun activation domain" Genes and Development, vol. 7, pp. 2135–2148 (1993).

Higgins, K., et al., "Antisense inhibition of the p65 subunit of NF–kb blocks tumorigenicity and causes tumor regression", Proceedings of the National Academy of Sciences USA, vol. 90, pp. 9901–9905 (1993).

Hirano, M., et al., "MEK Kinase is Involved in Tumor Necrosis Factor α–Induced NF–kB Activation and Degradation of IkB–α", The Journal of Biological Chemistry, vol. 271 No. 22, pp. 13234–13238 (1996).

Lange–Carter, C.A., et al., "A Divergence in the MAP Kinase Regulatory Network Defined by MEK Kinase and Raf", Science, vol. 260, pp. 315–319 (1993).

Lin, Y.–C., et al., "Activation of NF–kB requires proteolysis of the inhibitor IkB–α: Signal–induced phosphorylation of IkB– α alone does not release active NF–kB", Proceedings of the National Academy of Sciences USA, vol. 92, pp. 552–556 (1995).

Mellits, K.H., et al., "Proteolytic degradation of MAD3 (IkB α) and enhanced processing of the NF–kB precursor p105 are obligatory steps in the activation of NF–kb", Nucleic Acids Research, vol. 21, No. 22, pp. 5059–5066 (1993).

Miyomoto, S., et al., "Tumor necrosis factor α–Induced phosphorylation of IkB α is a signal for its degradation but not dissociation from NF–kB", Proceedings of the National Academy of Sciences USA, vol. 91, pp. 12740–12744 (1994).

Read, M.A., et al., "The Proteasome Pathway is Required for Cytokine–Induced Endothelial–Leukocyte Adhesion Molecule Expression", Immunity, vol. 2, pp. 493–506 (1995).

Siebenlist, U., et al., "Structure, Regulation and Function of NF–kB", Annual Review of Cell Biology, vol. 10, pp. 405–455 (1994).

Thanos, D. and Maniatis, T., "NF–kB: A Lesson in Family Values", Cell, vol. 80, pp. 529–532 (1995).

Thevenin, C., et al., "Induction of Nuclear Factor–kB and the Human Immunodeficiency Virus Long Terminal Repeat by Okadaic Acid, a Specific Inhibitor of Phosphatases 1 and 2A", New Biologist, vol. 2, No. 9, pp. 793–800 (1990).

Traenckner, E.B., et al., "Phosphorylatin of Human IkB–α on Serines 32 and 36 Controls IkB– α Protealysis and NF–kB Activation in Response to Diverse Stimuli", The EMBO Journal, vol. 14, No. 12, pp. 2876–2883 (1995).

Yang, Y.–L., et al., "Deficient signaling in mice devoid of double–stranded RNA–dependent protein kinase", The EMBO Journal, vol. 14, No. 24, pp. 6095–6106 (1995).

Xu, S., et al., "Cloning of rat MEK kinase 1 cDNA reveals an endogenous membrane–associated 195–kDa protein with a large regulatory domain", Proceedings of the National Academy of Sciences USA, vol. 93, pp. 5291–5295 (1996).

Khoshnan, A., et al., "The Physical Association of Protein Kinase Cθ with a Lipid Raft–Associated Inhibitor of kB Factor Kinase (IKK) Complex Plays a Role in the Activation of the NF–kB Cascade by TCR and CD28[1]", the Journal of Immunology, vol. 165, pp. 6933–6940 (2000).

DiDonato, J.A., et al., "A Cytokine–responsive IkB kinase that Activates the Transcription Factor NF–kB", Nature, vol. 388, pp. 548–554 (Aug. 1997).

Miller, B.S. and Zandi, E., "Complete Reconstitution of Human IkB Kinase (IKK) Complex in Yeast", The Journal of Biological Chemistry, vol. 276, No. 39, pp. 36320–36326 (Sep. 28, 2001).

Fu, D.–X., et al., "Human T–lymphotropic Virus Type 1 Tax Activates I–kB Kinase by Inhibiting I–kB Kinase–associated Serine/Threonine Protein Phosphotase 2A", The Journal of Biological Chemistry, vol. 278, No. 3, pp. 1487–1493 (Jan. 17, 2003).

Storz, P. and Toker, A., "Protein kinase D mediates a stress–induced NF–kB Activation and Survival Pathway", The EMBO Journal, vol. 22, No. 1, pp. 109–120 (2003).

Yang, J., et al., "The Essential Role of MEKK3 in TNF–induced NF–kB Activation", Nature Immunology, vol. 2, No. 7, pp. 620–624 (Jul. 2000).

Zhao, Q. and Lee, F.S., "Mitogen–activated Protein Kinase/ ERK Kinase Kinases 2 and 3 and Activate Nuclear Factor–kB through IkB Kinase–α and IkB Kinase–β", The Journal of Biological Chemistry, vol. 274, No. 13, pp. 8355–8358 (Mar. 26, 1999).

Tojima, Y., et al., "NAK is an IkB kinase–activating kinase", Nature, vol. 404, pp. 778–782 (Apr. 13, 2000).

Wang, C., et al., "TAK1 Is a Ubiquitin–dependent kinase of MKK and IKK", Nature, vol. 412, pp. 346–351 (Jul. 19, 2001).

Regnier, C.H., et al., "Identification and Characterization of an IkB Kinase", Cell, vol. 90, pp. 373–383 (Jul. 25, 1997).

Connelly, M.A. and Marcu, K.B., "CHUK, A New Member of the Helix–loop–helix and Leucine Zipper Families of Interacting Proteins, Contains a Serine–Threonine Kinase Catalytic Domain", Cellular and Molecular Biology Research, vol. 41, No. 6, pp. 537–549 (1995).

Alkalay, et al., "In Vitro Stimulation of IkB Phosphorylation Is Not Sufficient to Activate NF–κB", Mol. Cell. Biol., vol. 15, No. 3, pp. 1294–1304 (1995).

Alkalay, et al., "Stimulation–Dependent IκB–α Phosphorylation Marks the NF–κB inhibitor for Degradation via the Ubiquitin–Proteasome Pathway" Proc. Natl. Acad. Sci. USA, vol. 92, pp. 10599–10603 (1995).

Auffray, et al., "IMAGE: Integrated Molecular Analysis of the Human Genome and Its Expression" Sciences, vol. 318, pp. 263–272 (1995).

Baldi, et al., "Critical Role for Lysines 21 and 22 in Signal–Induced, Ubiquitin–Mediated Proteolysis of IκB–α " vol. 271, No. 1, pp. 376–379 (1996).

Barroga et al., "Constitutive Phosphorylation of IκB–60 by Casein Kinase II" Proc. Natl. Acad. Sci., vol. 92, pp. 7637–7641 (1995).

Beg, et al., "Tumor Necrosis Factor and Interleukin–1 Lead to Phosphorylation and Loss of IκB–α: a Mechanism for NF–κB Activation." Mol. Cell. Biol. 1316 pp. 3301–3310 (1993).

Belvin, et al., " Cactus Protein Degradation Mediates Drosophila Dorsal–Ventral Signaling" Genes and Dev., vol. 9, pp. 783–793 (1995).

Brockman, J.A., "Coupling of a Signal Response Domain in IκB–α to Multiple Pathways for NF–κB Activation" Mol. Cell. Biol., vol. 15, No. 5 2809–2818 (1995)

Brown, et al., "Control of IκB–α Proteolysis by Site–Specific, Signal–Induced Phosphorylation" Science, vol. 267, pp. 1485–1488 (1995).

Chau, "a Multiubiquitin Chain is Confined to Specific Lysine in a Targeted Short–Lived Protein" *Science*, vol. 243, pp. 1576–1583 (1989).

Chen, et al., "Signal–Induced Site–Specific Phosphorylation Targets IκB–α to the Ubiquitin–Proteasome Pathway" *Genes and Dev.*, vol. 9, pp. 1586–1597 (1995).

Ciechanover. "The Ubiquitin–Proteasome Proteolytic Pathway" *Cell*, vol. 79, pp. 13–21 (1994).

Devary, et al., "NF–κB Activation by Ultraviolet Light Not Dependent on a Nuclear Signal" *Science*, vol. 261, pp. 1442–1445 (1993).

Diaz–Meco. "ζPKC Induces Phosphorylation and Inactivation of I kappa B–alpha In Vitro" *EMBO J.*, vol. 13, No. 12, pp. 2842–2848 (1994).

Dominguez, et al., "Inhibition of Protein Kinase C ζ Subspecies Blocks the Activation of an NF–κB–like activity in *Xenopus laevis* Oocytes" *Mol. Cell. Biol.*, vol. 13, No. 2, pp. 1290–1295 (1993).

Finco and Baldwin, "78 B Site–Dependent Induction of Gene Expression by Diverse Inducers of Nuclear Factor κB Requires Raf–1", *J. Biol. Chem.*, vol. 268, No. 24, pp. 17676–17679 (1993).

Ghosh and Baltimore, "Activation Invitro of NF–κB by Phosphorylation of its Inhibitor IκB" *Nature*, vol. 344, pp. 678–682 (1990).

Henkel, et al., " Rapid Proteolysis of IκB–α is Necessary for Activation of Transcription Factor NF–κB" *Nature*, vol. 365, pp. 182–185 (1993).

Hershko and Ciechanover, "The Ubiquitin System for Protein Degradation" *Annu. Rev. Biochem.*, vol. 61, pp. 761–807 (1992).

Kumar, A., et al., "Double–Stranded RNA–Dependent Protein Kinase Activates Transcription Factor NF–κB by Phosphorylating IκB" *Proc. Natl. Acad. Sci. USA* vol. 91, pp. 6288–6292 (1994).

Kuno, et al., "Identification of an IκB–α—Associated Protein Kinase in a Human Monocytic Cell Line and Determination of its Phosphorylation Sites on IκB–α " *Biol. Chem.* vol. 270, No. 46 pp. 27914–27919 (1995).

Li and Sedivy "Raf–1 Protein Kinase Activates the NF–κB Transcription Factor By Disassociating the Cytoplasmic NF–κB–IκB complex" *Proc Natl Acad Sci USA.*, vol. 90, pp. 9247–9251 (1993).

Lin and Desiderio, "Regulation of V(D)J Recombination Activator Protein RAG–2 by Phosphorylation" *Science*, vol. 260, pp. 953–959 (1993).

Nishizawa, M., et al., "Degradation of MOS by the N–terminal Proline (Pro2)–Dependent Ubiquitin Pathway on Fertilization of Xenopus Eggs: Possible Significance of Natural Selection for Pro2 in MOS" *EMBO J.*, vol. 12, No. 10, pp. 4021–4027 (1993).

Palombella , et al., "The Ubiquitin–Proteasome Pathway is Required For Processing the NF–κB1 Precursor Protein and the Activation of NF–κB" *Cell*, vol. 78, pp. 773–785 (1994).

Pawlak, et al., "Characterization of a Large Population of mRNAs From Human Testis" *Genomics*, vol. 26, pp. 151–158 (1995).

Pickart and Rose, "Functional Heterogeneity of Ubiquitin Carrier Proteins" *J. Biol. Chem.*, vol. 260, No. 3, pp. 1573–1581 (1985).

Rodriguez, M.S., et al., "Inducible Degradation of IκBα In Vitro and In Vivo Requires the Acidic C–Terminal Domain of the Protein" Mol. Cell. Biol., vol. 15(5), pp. 2413–2419 (1995).

Scherer, et al., "Signal–Induced Degradation of IκB–α requires site–specific Ubiquitination" *Natl. Acad. Sci. USA*, vol. 92, pp. 11259–11263 (1995).

Schreck, et al., "Reactive Oxygen Intermediates as Apparently Widely Used Messengers in the Activation of the NF–κB Transcription Factor and HIV–1" EMBO J., vol. 10, No. 8, pp. 2247–2258 (1991).

Schutze, et al., "TNF Activates NF–kappa B by Phosphatidylcholine–Specific Phospholipase C–Induced "Acidic" Sphingomyelin Breakdown" *Cell*, vol. 71 pp. 765–777.

Sun, et al., "NF–κB Controls Expression of Inhibitor IκB–α: Evidence For An Inducible Autoregulatory Pathway", *Science*, vol. 259, pp. 1912–1915 (1993).

Traenckner et al., "A Proteasome Inhibitor Prevents Activation of KF–κB and Stabilizes a Newly Phosphorylated Form of IκB–α That is Still Bound to NF–κB" *EMBO J.*, vol. 13, pp. 5433–5441 (1994).

Verma, et al., "ReI/NF–κB/IκB Family: Intimate Tales of Association and Disassociation" *Genes and Dev.*, vol. 9 pp. 2723–2735 (1995).

Wasserman, "A Conserved Signal Transduction Pathway Regulating the Activity of the Rel–Like Proteins Dorsal and NF–κB" *Mol. Biol. Cell.*, vol. 4, pp. 767–771 (1993).

Whiteside, et al., "N– and C– Terminal Sequences Control Degradation of MAD3/IκB–α in Response to Inducers of NF–κB Activity" *Mol. Cell. Biol.*, vol. 15, No. 10, pp. 5339–5345 (1995).

Yaglom, et al., "p34Cdc28–Mediated Control of Cln3 Cyclin Degradation" *Mol. Cell. Biol.*, vol. 15, No. 2, pp. 731–741 (1995).

EMBL Database entry Hs369288, Accession No. N56369, from International Search Report, International Application No. PCT/US97/04195.

EMBL Database entry Hs2038, Accession No. T19203, from International Search Report, International Application No. PCT/US97/04195.

Lee et al., "Activation of the IκBα Kinase Complex by MEKK1, a Kinase of the JNK Pathway" *Cell*, vol. 88, pp. 213–222 (1997).

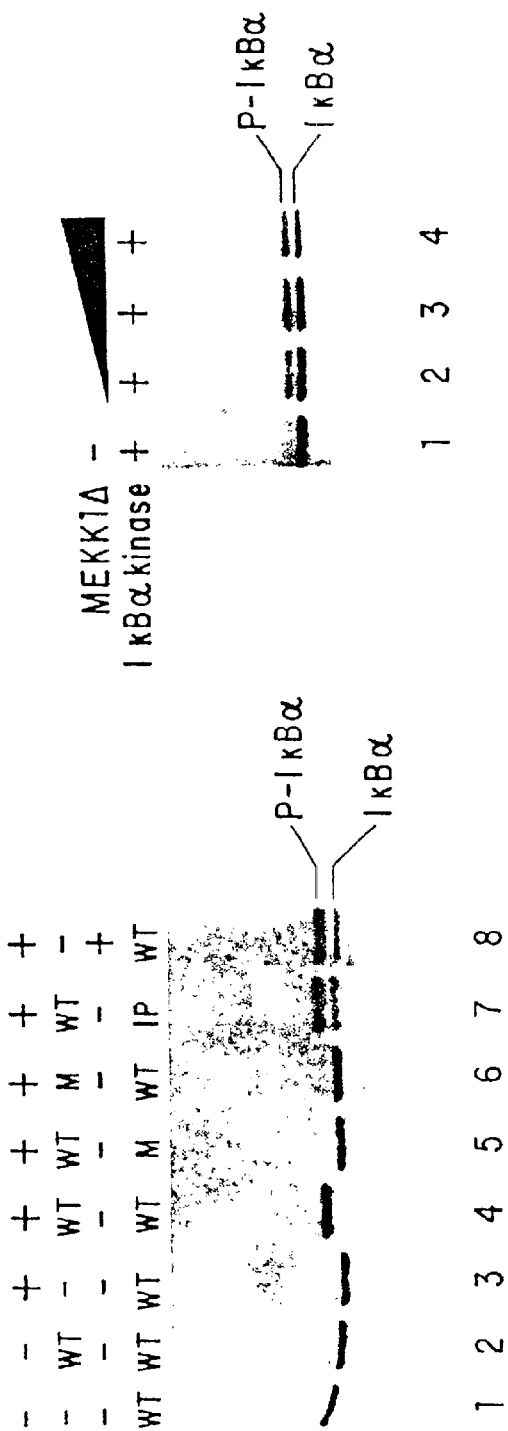

A  
B  p50:    pep1:  [L/I] [Y] [V] [E] [L/I] [E] [R]
         pep2:  [L/I] [Q/K] [E] [V] [L/I] [E] [T] [L/I] [L/I] [S]
                [L/I] [E] [K*]
C        pep3:  [L/I] [F] [T] [T] [M] [E] [L/I] [M] [R]

D  p40:    pep4:  [T] [Y] [H] [A] [L*] [S] [N] [L*] [P] [K*]

FIG.21

```
  1 gggtgacgag tggtggccga agcaggggga cagcaaggga cgctcaggcg gggaccatgg
 61 cggacggcgg ctcggagcgg gctgacgggc gcatcgtcaa gatggaggtg gactacagcg
121 ccacggtgga tcagcgccta cccgagtgtg cgaagtatgc caaggaagga agacttcaag
181 aagtcattga aacccttctc tctctggaaa agcagactcg tactgcttcc gatatggtat
241 cgacatcccg tatcttagtt gcagtagtga agntgtgcta tgaggctaaa gaatgggatt
301 tacttaatta aaaatattat tgctttttgt ccaaaaggcg gagtcaagtt aaaaacaagc
361 tagttgacaa aaaatggatt naacagttgc tgtnacttat tgttt
```

```
  1 ataccaagag gtaccaggaa gcattgcatt tgggttctca gctgctgcgg gagttgaaaa
 61 agatggacga caaagctctt ttggtggaag tacagctttt agaaagcaaa acataccatg
121 ccctgagcaa cctgccgaaa gcccgagctg ccttaacttc ttctcgaacc acagcaaatg
181 ccatctactg cccccctaaat tgcaggccac cttggacatg cagtcgggta ttatccatgc
241 agcagaagag aaggcttgaa actcgtactc atacttctat gaggcattta gggtatgact
301 catcgacagc ccaaggcatc aca
```

FIG.22

KINASE CAPABLE OF SITE-SPECIFIC PHOSPHORYLATION OF IκBα

CROSS REFERENCE TO RELATED APPLICATIONS

This application is a continuation of U.S. patent application Ser. No. 09/406,293, filed on Sep. 24, 1999, now abandoned, which is a divisional of U.S. patent application Ser. No. 08/825,559, filed on Mar. 19, 1997, now U.S. Pat. No. 6,107,073, which, in turn, is a continuation-in-part of U.S. patent application Ser. No. 08/616,499, filed on Mar. 19, 1996, now abandoned.

BACKGROUND OF THE INVENTION

1. Field of the Invention

The present invention relates, in general, to a kinase which in its activated state is capable of site-specific phosphorylation of IκBα, IκBα kinase. In particular, the present invention relates to the purified kinase, purified polypeptide subunits of the kinase, nucleic acid molecules coding for the purified polypeptide subunits; recombinant nucleic acid molecules; cells containing the recombinant nucleic acid molecules; antibodies having binding affinity specifically to the kinase or its polypeptide subunits; hybridomas containing the antibodies; nucleic acid probes for the detection of the nucleic acid encoding the kinase; a method of detecting nucleic acids encoding the kinase or polypeptides of the kinase in a sample; and kits containing nucleic acid probes or antibodies. This invention further relates to bioassays using the nucleic acid sequence, protein or antibodies of this invention to diagnose, assess, or prognose a mammal afflicted with an undesired activation of NF-κB. This invention also relates to ligands, agonists, and antagonists of the kinase, and diagnostic and therapeutic uses thereof. This invention also relates to bioassays using the kinase or polypeptides of the kinase of this invention to identify ligands, agonists, and antagonists. More specifically, this invention relates to selective inhibitors of the kinase and to structure-based design of ligands, agonists, and antagonists of the kinase. This invention further relates to gene therapy using the nucleic acids of the invention.

2. Related Art

Regulation of the immune and inflammatory responses requires the activation of specific sets of genes by a variety of extracellular signals. These signals include mitogens (e.g., LPS and PMA), cytokines (e.g., TNF-α and IL-1β), viral proteins (e.g., HTLV-1 Tax), antigens, phosphatase inhibitors (e.g., okadaic acid and calyculin A), and UV light. The rel/NF-κB family of transcriptional activator proteins plays an essential role in the signal transduction pathways that link these signals to gene activation (reviewed by Siebenlist, U. et al., *Annu. Rev. Cell. Biol.* 10:405–455 (1994); Baerle & Henkel, *Annu. Rev. Immunol.* 12:141–179 (1994); Thanos & Maniatis, *Cell* 80:529–532 (1995); Finco & Baldwin, *J. Biol. Chem.* 24:17676–17679 (1993); Verma, I. M. et al., *Genes & Dev.* 9:2723–2735 (1995)). NF-κB (p50/RelA(p65)), and other heterodimeric rel family proteins are sequestered in the cytoplasm through their association with IκBα or IκBβ, members of the IκB family of inhibitor proteins. In the case of IκBα, and most likely IκBβ, stimulation of cells leads to rapid phosphorylation and degradation of the inhibitor. Consequently NF-κB is released and translocates into the nucleus where it activates the expression of target genes. Phosphorylation of IκBα per se is not sufficient to dissociate NF-κB from the latent complex (Palombella, V. J., *Cell.* 78:773–785 (1994); Traenckner, E. B.-M. et al., *EMBO J.* 13:5433–56441 (1994); Finco, T. S. et al., *Proc. Natl. Acad. Sci. USA* 91:11884–11888 (1994); Miyamoto, S. et al., *Proc. Natl. Acad. Sci. USA* 91:12740–12744 (1994); Lin, Y.-C. et al., *Proc. Natl. Acad. Sci. USA* 92:552–556 (1995); Alkalay, I. et al., *Mol. Cell. Biol.* 15:1294–1304 (1995); DiDonato, J. A. et al., *Mol. Cell. Biol.* 15:1302–1311 (1995)). Rather, phosphorylation triggers the degradation of IκBα (Brown, K. et al., *Science* 267:1485–1491 (1995); Brockman, J. A. et al., *Mol. Cell. Biol.* 15:2809–2818 (1995); Traenckner, E. B.-M. et al., *EMBO J.* 14:2876–2883 (1995); Whiteside, S. T. et al., *Mol. Cell. Biol.* 15:5339–5345 (1995)).

Recently, it has been shown that signal-induced degradation of IκBα is mediated by the ubiquitin-proteasome pathway (Chen, Z. J. et al., *Genes & Dev.* 9:1586–1597 (1995); Scherer, D. C. et al., *Proc. Natl. Acad. Sci. USA* 92:11259–11263 (1995); Alkalay, I. et al., *Proc. Natl. Acad. Sci. USA.* 92:10599–10603 (1995)). In this pathway, a protein targeted for degradation is first modified by covalent attachment of ubiquitin, a highly conserved polypeptide of 76 amino acids (reviewed by Hershko & Ciechanover, *Annu. Rev. Biochem.* 61:761–807 (1992); Ciechanover, A., *Cell* 79:13–21 (1994)). Ubiquitination is a three-step process: First, ubiquitin is activated by a ubiquitin activating enzyme (E1); the activated ubiquitin is then transferred to a ubiquitin carrier protein (E2, also referred to as ubiquitin conjugating enzyme or UBC); finally, ubiquitin is conjugated to a protein substrate by forming an isopeptide bond between the carboxyl terminal glycine residue of ubiquitin and the ε-amino group of one or more lysine residues of the protein substrate. This conjugation step often requires a ubiquitin protein ligase (E3). Multiple molecules of ubiquitin can be ligated to a protein substrate to form multi-ubiquitin chains, which are then recognized by a large, ATP-dependent protease (MW ~2000 kDa) called the 26S proteasome. The 26S proteasome is composed of a 20S catalytic core, and a 19S regulatory complex (reviewed by Goldberg, A. L., *Science* 268:522–523 (1995)).

Multiple E2s and E3s function together to mediate the ubiquitination of a variety of cellular proteins. For example, there are at least a dozen E2s in yeast that display distinct substrate specificities and carry out distinct cellular functions. The closely related E2 proteins UBC4 and UBC5 are involved in the turnover of many short-lived and abnormal proteins, and they play an essential role in the stress response (Seufert & Jentsch, *EMBO J.* 9:543–550 (1990)). Homologs of UBC4/UBC5 mediate the ubiquitination of the P53 protein in conjunction with the HPV-16 E6-E6AP complex, which functions as an E3 (Schaffner, M. et al., *Cell.* 75:495–505 (1993)). These E2s have also been implicated in the ubiquitination of the MATα2 Processor (Chen, P. et al., *Cell* 74:357–369 (1993)), cyclin B (King, R. W. et al., *Cell* 81:279–288 (1995)), and the NF-κB precursor protein P105 (Orian, A. et al., *J. Biol. Chem.* 270:21707–21714 (1995)). The involvement of UBC4/UBC5 in the ubiquitination of such diverse substrates indicates that these E2s alone cannot confer substrate specificity. However, they may act together with specific E3s to recognize specific substrates. Although relatively few E3s have been identified thus far, the existence of a large family of these proteins is likely (Huibregtse, J. M. et al., *Proc. Natl. Acad. Sci. USA* 92:2563–2567 (1995)).

Ubiquitination of IκBα is regulated by signal-induced phosphorylation at two specific residues, serines 32 and 36 (Chen, Z. J. et al., *Genes & Dev.* 9:1586–1597 (1995)). Single amino acid substitutions of one or both of these residues abolish the signal-induced phosphorylation and degradation of IκBα (Brown, K. et al., *Science* 267:1485–1491 (1995); Brockman, J. A. et al., *Mol. Cell Biol.* 15:2809–2818 (1995); Traenckner, E. B.-M. et al., *EMBO J.* 14:2876–2883 (1995); Whiteside, S. T. et al., *Mol. Cell. Biol.* 15:5339–5345 (1995)). The same mutations also abolish the okadaic acid-induced phosphorylation and ubiquitination of IκBα in vitro (Chen, Z. J. et al., *Genes & Dev.* 9:1586–1597 (1995)). Relatively little is known about the signal transduction pathways and the kinase(s) responsible for the site-specific phosphorylation of IκBα. Mutants of IκBα lacking serines 32 and 36 are resistant to induced phosphorylation by a variety of stimuli, suggesting that different signal transduction pathways converge on a specific kinase or kinases. However, despite considerable effort, the identification of this IκBα kinase has remained elusive (Verma, I. M. et al., *Genes & Dev.* 9:2723–2735 (1995)).

Several serine/threonine kinases, including protein kinase C (PKC), heme-regulated eIF-2α kinase (HRI), protein kinase A (Ghosh & Baltimore, *Nature* 344:678–682 (1990)), casein kinase II (Barroga, C. F. et al., *Proc. Natl. Acad. Sci. USA* 92:7637–7641 (1995)) and a recently described 42 kDa kinase (Kano, K. et al., *J. Biol. Chem.* 270:27914–27919 (1995)), have been shown to phosphorylate IκBα in vitro. However, none of these kinases have been shown to phosphorylate IκBα at serines 32 and 36. Various kinases have also been implicated in the regulation of NF-κB in vivo, such as ζPKC (Dominguez, I. et al., *Mol. Cell. Biol.* 13:1290–1295 (1993); Diaz-Meco, M. T. et al., *EMBO J.* 13:2842–2848 (1994)), ceramide-dependent protein kinase (Schutze, S. et al., *Cell* 71:765–776 (1992)), tyrosine kinases (Devary, Y. et al., *Science* 261:1442–1445 (1993)), Raf (Finco & Baldwin, *J. Biol. Chem.* 24:17676–17679 (1993); Li & Sedivy, *Proc. Natl. Acad. Sci. USA* 90:9247–9251 (1993)), and the Drosophila pelle kinase, which is required for the inactivation of cactus, a Drosophila IκB homolog (Wassermann, S. A., *Mol. Biol. Cell* 4:767–771 (1993)). These kinases may function at various steps in the signal transduction pathway upstream of IκBα phosphorylation, but none have been shown to directly phosphorylate IκBα at relevant sites.

Although the diverse nature of NF-κB stimuli suggests that the initial steps in the signal transduction pathways are distinct, these pathways appear to converge on the generation of reactive oxygen intermediates (ROIs, such as $H_2O_2$), which are thought to function as common second messenger-like molecules in the activation of NF-κB (Schreck, R. et al., *EMBO J.* 10:2247–2258 (1991)). At present the mechanistic link between ROIs and IκBα phosphorylation is not understood.

The establishment of an in vitro system for signal-induced phosphorylation and ubiquitination of IκBα was previously reported (Chen, Z. J. et al., *Genes & Dev.* 9:1586–1597 (1995)). The present invention involves fractionating HeLa cell cytoplasmic extracts and assaying for specific phosphorylation and ubiquitination of IκBα. The present invention provides a high molecular weight kinase complex that, in its activated state, specifically phosphorylates IκBα at serines 32 and 36. Surprisingly, UBC4/UBC5, ubiquitin, and E1 are not only involved in the ubiquitination of IκBα, but may also be required for the phosphorylation of IκBα. Additional experiments reveal that this IκBα kinase can be activated by a prior ubiquitination event. In this case, ubiquitination serves a regulatory function without involving proteolysis. Additionally, this IκBα may be activated by MEKK1.

SUMMARY OF THE INVENTION

Signal-induced activation of the transcription factor NF-κB requires specific phosphorylation of the inhibitor IκBα (SEQ ID NO:9) and its subsequent proteolytic degradation. Phosphorylation of serine residues 32 and 36 targets IκBα to the ubiquitin-proteasome pathway. The present invention provides a substantially purified large, multi-subunit kinase (MW~700 kDa) that, in its active state, phosphorylates IκBα at serines 32 and 36. Preferably, the kinase comprises an amino acid sequence which is at least 60% homologous to the amino acid sequence of any one of FIGS. 21A–D. Remarkably, this kinase may be activated by a ubiquitination event requiring the ubiquitin activating enzyme (E1), a specific ubiquitin carrier protein (E2) of the UBC4/UBC5 family, and ubiquitin. Thus, in this case, ubiquitination serves a novel regulatory function that does not involve proteolysis. Alternatively, the kinase may be activated via phosphorylation by MEKK-1. Additional activation routes, e.g. phosphorylation by a kinase other than MEKK-1, may also be possible.

The invention further provides the substantially pure polypeptide subunits of the above-described kinase.

The invention provides isolated nucleic acid molecules coding for subunits of the above-described kinase.

The invention also provides a nucleic acid probe for the specific detection of the presence of nucleic acid encoding the above-described kinase or its subunits or a fragment thereof in a sample.

The invention further provides a method of detecting the above-described nucleic acid in a sample.

The invention also provides a kit for detecting the presence of the above-described nucleic acid in a sample.

The invention further provides a recombinant nucleic acid molecule comprising, 5' to 3', a promoter effective to initiate transcription in a host cell and the above-described nucleic acid molecule.

The invention also provides a recombinant nucleic acid molecule comprising a vector and the above-described nucleic acid molecule.

The invention also provides a cell that contains the above-described recombinant nucleic acid molecule.

The invention further provides a non-human organism that contains the above-described recombinant nucleic acid molecule.

The invention also provides an antibody having binding affinity specifically to the above-described kinase or to a subunit of the above-described kinase.

The invention further provides a method of detecting the above-described kinase or one of its subunits in a sample.

The invention also provides a method of measuring the amount of the above-described kinase in a sample.

The invention further provides a diagnostic kit comprising a first container means containing the above-described antibody, and a second container means containing a conjugate comprising a binding partner of the monoclonal antibody and a label.

The invention also provides a hybridoma which produces the above-described monoclonal antibody.

The invention further provides diagnostic methods for human disease, in particular diseases, disorders, and injuries resulting from an undesired activation of NF-κB.

The invention also provides methods for therapeutic uses involving (1) the nucleic acid sequence encoding the above-described kinase or a subunit thereof and/or (2) the above-described kinase or a subunit thereof.

The invention provides ligands, agonists, and antagonists of the above-described kinase and diagnostic and therapeutic uses for these molecules. Preferably, the molecule is a selective inhibitor of kinase activity, i.e. the ability to phosphorylate IκBα at serine residues 32 and 36.

The invention also provides assays for the identification of ligands, agonists and antagonists of the above-described kinase.

Further objects and advantages of the present invention will be clear from the description that follows.

DEFINITIONS

In the description that follows, a number of terms used in recombinant DNA (rDNA) technology, protein purification, and diagnostic and therapeutic methods are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA.

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome can be digested by a particular restriction endonuclease into a discrete set of restriction fragments.

Polyacrylamide Gel Electrophoresis (PAGE). The most commonly used technique (though not the only one) for achieving a fractionation of polypeptides on the basis of size is polyacrylamide gel electrophoresis. The principle of this method is that polypeptide molecules migrate through the gel as though it were a sieve that retards the movement of the largest molecules to the greatest extent and the movement of the smallest molecules to the least extent. Note that the smaller the polypeptide fragment, the greater the mobility under electrophoresis in the polyacrylamide gel. Both before and during electrophoresis, the polypeptides typically are continuously exposed to the detergent sodium dodecyl sulfate (SDS), under which conditions the polypeptides are denatured. Native gels are run in the absence of SDS.

The polypeptides fractionated by polyacrylamide gel electrophoresis can be visualized directly by a staining procedure if the number of polypeptide components is small.

Western Transfer Procedure. The purpose of the Western transfer procedure (also referred to as blotting) is to physically transfer polypeptides fractionated by polyacrylamide gel electrophoresis onto a nitrocellulose filter paper or another appropriate surface or method, while retaining the relative positions of polypeptides resulting from the fractionation procedure. The blot is then probed with an antibody that specifically binds to the polypeptide of interest.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Antibody Probe. To visualize a particular polypeptide sequence in the western blot procedure, a labeled antibody probe is exposed to the fractionated polypeptides bound to the nitrocellulose filter. The areas on the filter that carry polypeptides that bind to the labeled antibody probe become labeled themselves as a consequence of the binding. The areas of the filter that exhibit such labeling are visualized.

Stringent Hybridization Conditions. Examples of hybridization conditions can be found in Ausubel, F. M. et al., *Current protocols in Molecular Biology*, John Wily & Sons, Inc., New York, N.Y. (1989). A nitrocellulose filter is incubated overnight at 68° C. with labeled probe in a solution containing 50% formamide, high salt (either 5× SSC[20×: 3M NaCl/0.3M trisodium citrate] or 5× SSPE [20×: 3.6M NaCl/0.2M $NaH_2PO_4$/0.02M EDTA, pH 7.7]), 5× Denhardt's solution, 1% SDS, and 100 μg/ml denatured salmon sperm DNA. This is followed by several washes in 0.2× SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens or by site-directed mutagenesis. A mutant variation of a nucleic acid molecule results from a mutation. A mutant polypeptide can result from a mutant nucleic acid molecule.

Species. A "species" is a group of actually or potentially interbreeding natural populations. A species variation within a nucleic acid molecule or protein is a change in the nucleic acid or amino acid sequence that occurs among species and can be determined by DNA sequencing of the molecule in question.

Purified. A "purified" protein or nucleic acid is a protein or nucleic acid preparation that is generally free of contaminants, whether produced recombinantly, chemically synthesized or purified from a natural source.

% Homologous. When referring to one amino acid sequence as being X% homologous to another amino acid sequence, what is meant is the percentage of sequence identity or sequence similarity. Amino acid sequence similarity is further described in Table 1, infra.

Subunit of the Kinase. The kinase is a multi-subunit protein. Each subunit is defined herein to be a single polypeptide which is encoded by a nucleic acid sequence.

p85, p70, p62, p55, p50, p43, p40, p38, p36, p33, p31.

For purposes of the invention, these terms refer to polypeptide subunits of the above-described kinase, wherein each subunit has a corresponding molecular weight observed by SDS PAGE. For example, p85 is a polypeptide subunit with approximate molecular weight of 85 KDa observed by SDS PAGE, of a large, multisubunit kinase that in its active state phosphorylates IκBα at serines 32 and 36. p70 has an approximate molecular weight by SDS PAGE of 70 KDa, p62 has an approximate molecular weight by SDS PAGE of 62 kDa, and so on.

Substrate. A substrate for the kinase is a ligand which becomes phosphorylated as a result of its interaction with the kinase.

Ligand. Ligand refers to any molecule that can interact with the above-described kinase or a subunit thereof. The ligand can be a naturally occurring polypeptide, or may be synthetically or recombinantly produced. The ligand can be soluble or membrane bound. The ligand can also be a nonprotein molecule that acts as a ligand when it interacts with the kinase. Interactions between the ligand and the kinase include, but are not limited to, any covalent or non-covalent interactions. Preferably, the ligand interacts selectively with the kinase. Agonists and antagonists of the kinase that can interact with the kinase are examples of ligands according to the present invention. Preferably, the ligand is a selective inhibitor of the kinase activity, i.e. the ability to phosphorylate IκB-α at serine residues 32 and 36.

Disease states characterized by undesired activation of NF-κB. The phrase disease states characterized by undesired activation of NF-κB includes, but is not limited to, disease states in a mammal which can include inflammation, HIV infection, cancer, sepsis, psoriasis, and restenosis.

Drug. Drugs include, but are not limited to, proteins, peptides, degenerate peptides, agents purified from conditioned cell medium, organic molecules, inorganic molecules, antibodies or oligonucleotides. Other candidate drugs include analogs of the above-described kinase ligand or ligands. The drug can be naturally occurring or synthetically or recombinantly produced. One skilled in the art will understand that such drugs can be developed by the assays described below.

BRIEF DESCRIPTION OF THE FIGURES

FIG. 2.

FIG. 3.

FIG. 4.

FIG. 5.

FIG. 6.

FIG. 7.

FIG. 10.

FIG. 11.

FIG. 13. FIGS. 13A–13D are representations of autoradiographs of SDS-PAGE gels demonstrating that MEKK1 directly activates IκBα kinase.

FIG. 14.

FIG. 15.

FIG. 16.

FIG. 19.

FIG. 21. FIGS. 21A–21D are amino acid sequences for pep1–pep4.

FIG. 22. FIGS. 22A–22B are nucleic acid sequences encoding p50 and p40, respectively.

DETAILED DESCRIPTION OF THE PREFERRED EMBODIMENTS

Figure 1:
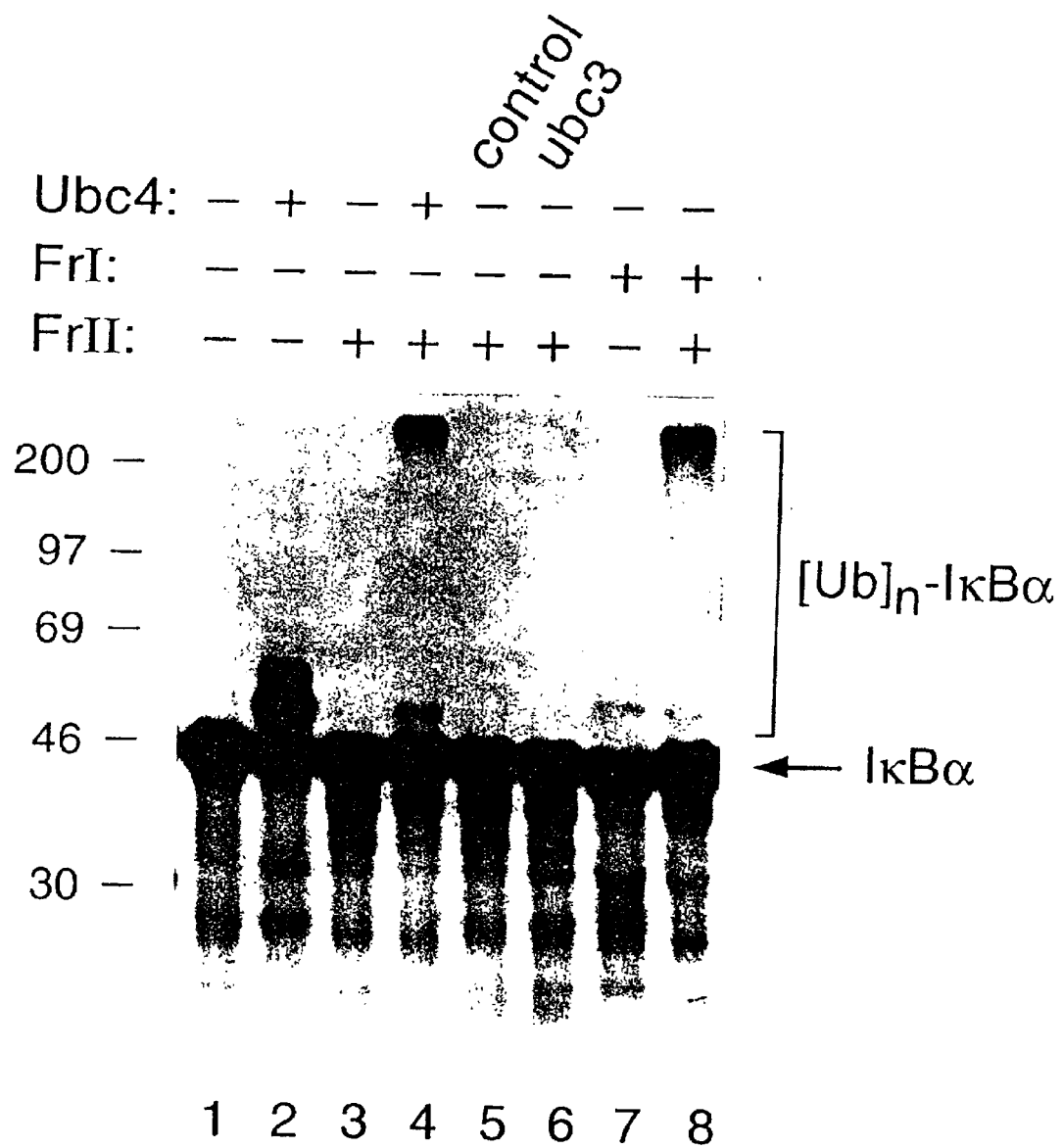
FIG. 1. Representation of an autoradiograph of an SDS-PAGE gel demonstrating that ubc4, but not ubc3, supports ubiquitination of IκBα.

For purposes of clarity of disclosure, and not by way of limitation, the detailed description of the invention is divided into the following subsections:

I. A Substantially Pure Kinase and Subunits Thereof.

II. Isolated Nucleic Acid Molecules Coding for the Kinase Subunits.

III. A Nucleic Acid Probe for the Specific Detection of Nucleic Acid encoding the Kinase or A Subunit or Fragment Thereof.

IV. A Method of Detecting The Presence of Nucleic Acid Encoding the Kinase or a Subunit or Fragment Thereof in a Sample.

V. A Kit for Detecting the Presence of the Kinase or A Subunit Thereof in a Sample.

VI. DNA Constructs Comprising a Nucleic Acid Molecule Encoding a Kinase Subunit and Cells Containing These Constructs.

VII. An Antibody Having Specific Binding Affinity to the Kinase or Subunit Thereof and a Hybridoma Containing the Antibody.

VIII. A Method of Detecting the Kinase or A Subunit Thereof in a Sample.

IX. A Diagnostic Kit Comprising Antibodies to the Kinase or A Subunit Thereof.

X. Diagnostic Screening and Treatment.
XI. Ligands of the Kinase
XII. Bioassays for obtaining ligands of the kinase.
XIII. Transgenic and "Knock-Out" Mice.

I. A Purifed Kinase and Subunits Thereof.

The present invention relates to a purified kinase which, in its activated state, is capable of site-specific phosphorylation of IκBα (SEQ ID NO:9); subunits thereof; and functional derivatives thereof. More specifically, the kinase is capable of activation by ubiquitination or via phosphorylation by MEKK1.

It is preferred that the purified kinase comprise an amino acid sequence which is at least 60–100% homologous to any one of the amino acid sequences of FIGS. 21A–21D or is encoded by a nucleic acid which hybridizes to a second nucleic acid having the nucleotide sequence of any one of FIGS. 22A–B. Preferably, the kinase comprises an amino acid sequence that is at least 60, 65, 70, 75, 80 or 85% homologous to any one of the amino acid sequences of FIGS. 21A–21D or is encoded by a nucleic acid which preferentially hybridizes or hybridizes under low stringency conditions to a second nucleic acid having the nucleotide sequence of any one of FIGS. 22A–B. More preferably, the kinase comprises an amino acid sequence that is at least 90, 95, 98 or 100% homologous to any one of the amino acid sequences of FIGS. 21A–21D or is encoded by a nucleic acid which hybridizes under moderate or high stringency condition to a second nucleic acid having the nucleotide sequence of any one of FIGS. 22A–B. Most preferably the purified kinase comprises any one of the amino acid sequences of FIGS. 21A–21D or is encoded by a nucleic acid comprising the nucleotide sequence of any one of FIGS. 22A–B. More preferably, the purified kinase comprises at least 2 or 3, most preferably 4, of the amino acid sequences of FIGS. 21A–21D or amino acid sequences that are 60, 65, 70, 75, 80, or 85% homologous to the amino acid sequences of FIGS. 21A–21D.

In a further embodiment, the present invention relates to a purified polypeptide subunit of the kinase complex which phosphorylates IκBα at serine residues 32 and 36 or a functional derivative thereof. The subunit may be a catalytic, regulatory, or structural subunit. Preferably, the subunit is a regulatory or catalytic subunit, more preferably a catalytic subunit which when active is capable of phosphorylating IκBα. Preferably, the subunit is selected from the group consisting of p85, p70, p62, p55, p50, p43, p40, p38, p36, p33, p31 or is a mutant or species variation thereof, or has at least 70% identity or at least 85% similarity thereto (preferably, at least 90%, 95%, 96%, 97%, 98%, or 99% identity or at least 95%, 96%, 97%, 98%, or 99% similarity thereto), or at least 6 contiguous amino acids thereof (preferably, at least 10, 15, 20, 25, or 50 contiguous amino acids thereof).

Preferably, the p40 subunit or functional derivative thereof comprises an amino acid sequence that is at least 60–100% (more preferably at least 60, 65, 70, 75, 80 or 85%, most preferably at least 90, 95, 98 or 100%) homologous to the amino acid sequence of FIG. 21D.

Preferably, the p50 subunit or functional derivative thereof comprises an amino acid sequence that is at least 60–100% (more preferably at least 60, 65, 70, 75, 80 or 85%, more preferably at least 90, 95, 98 or 100%) homologous to any one of, or any combinantion of, the amino acid sequences of FIGS. 21A–21C.

In a preferred embodiment, the invention relates to an epitope of the above-described subunit polypeptide. The epitope of these polypeptides is an immunogenic or antigenic epitope. An immunogenic epitope is that part of the protein which elicits an antibody response when the whole protein is the immunogen. An antigenic epitope is a fragment of the protein which can elicit an antibody response. Methods of selecting antigenic epitope fragments are well known in the art. See, Sutcliffe et al., *Science* 219:660–666 (1983). Antigenic epitope-bearing peptides and polypeptides of the invention are useful to raise an immune response that specifically recognizes the polypeptides. Antigenic epitope-bearing peptides and polypeptides of the invention comprise at least 7 amino acids (preferably, 9, 10, 12, 15 or 20 amino acids) of the proteins of the invention.

Degradation of a number of proteins has been shown to be induced by phosphorylation (Lin & Desiderio, *Science* 260:953–959 (1993); Yagiom, J. et al., *Mol. Cell. Biol.* 15:731–741 (1995)) and dephosphorylation (Nishizawa, M. et al., *EMBO J.* 12:4021–4027 (1993)), and in some cases the ubiquitin-proteasome pathway has been implicated. The degradation of IκBα is a well characterized example of coupling between phosphorylation and ubiquitination (Chen, Z. J. et al., *Genes & Dev.* 9:1586–1597 (1995); Scherer, D.C. et al., *Proc. Natl. Acad. Sci. USA* 92:11259–11263 (1995); Alkalay, I. et al., *Proc. Natl. Acad. Sci. USA* 92:10599–10603 (1995)). It was previously shown that ubiquitination of IκBα is regulated by its phosphorylation at serines 32 and 36 (Chen, Z. J. et al., *Genes & Dev.* 9:1586–1597 (1995)), residues required for the signal-induced phosphorylation and degradation of IκBα in vivo (Brown, K. et al., *Science* 267:1485–1491 (1995); Brockman, J. A. et al., *Mol. Cell. Biol.* 15:2809–2818 (1995); Traenckner, E. B.-M. et al., *EMBO J.* 14:2876–2883 (1995); Whiteside, S. T. et al., *Mol. Cell. Biol.* 15:5339–5345 (1995)).

The kinase activity described here has several properties expected for a bona fide IκBα kinase. The activated kinase phosphorylates both free IκBα and IκBα bound to RelA at serine residues 32 and 36. In addition, IκBα phosphorylated by this kinase remains bound to NF-κB, a property expected from in vivo studies (reviewed by Finco & Baldwin, *Immunity* 3:263–272 (1995)). This property of the kinase is in contrast to previous examples of in vitro IκBα phosphorylation, which resulted in the dissociation of the NF-κB/IκBα complex (Ghosh & Baltimore, *Nature* 344:678–682 (1990); Kumar, A. et al., *Proc. Natl. Acad. Sci. USA* 91:6288–6292 (1994)). Finally, the in vitro phosphorylated IκBα can be ubiquitinated at specific lysine residues (K21 and K22) (Chen, Z. J. et al., *Genes & Dev.* 9:1586–1597 (1995); Scherer et al., *Proc. Natl. Acad. Sci. USA* 92:11259–11263 (1995); Baldi et al., *J. Biol. Chem.* 271:376–379 (1996)), and these residues are required for signal-induced degradation of IκBα in vivo (Scherer, D. C. et al., *Proc. Natl. Acad. Sci. USA* 92:11259–11263 (1995)).

Purification of the Kinase

The phosphatase inhibitor, okadaic acid, was previously demonstrated to induce the phosphorylation and ubiquitination of in vitro translated IκBα in a HeLa cell cytoplasmic extract (Chen, Z. J. et al., *Genes & Dev.* 9:1586–1597 (1995)). To identify the enzymes involved in the in vitro ubiquitination of IκBα, the cytoplasmic extracts were separated into two fractions by monoQ ion-exchange chromatography. Fraction I (Fr.I) is the monoQ column flow-through, while fraction II (Fr.II) is the 0.5 M KCl eluate. Each fraction was assayed for its ability to support the ubiquitination of IκBα. The reaction mixture contained in vitro translated $^{35}$S-labeled IκBα, an ATP regenerating system, E1, ubiquitin, ubiquitin aldehyde (to inhibit isopeptidases) and okadaic acid (Chen, Z. J. et al., *Genes & Dev.* 9:1586–1597 (1995)).

Neither fraction alone was sufficient to support the ubiquitination of IκBα (FIG. 1, lanes 3 and 7). However, when Fr.I was mixed with Fr.II multi-ubiquitination of IκBα was observed (FIG. 1, lane 8). Fr.I is known to contain a subfamily of E2s called UBC4/UBC5, whereas Fr.II contains all other known E2s (Pickart & Rose, *J. Biol. Chem.* 260:1573–1581 (1985)). Experiments were carried out to determine whether recombinant yeast UBC4 can substitute for Fr.I in catalyzing the ubiquitination of IκBα. Yeast UBC4 alone catalyzed the formation of low molecular weight ubiquitinated conjugates of IκBα (FIG. 1, lane 2). The E3-independent formation of low molecular weight conjugates catalyzed by certain E2s was previously reported (Pickart & Rose, *J. Biol. Chem.* 260:1573–1581 (1985)). The biological significance of this ubiquitination is not clear, since these conjugates are not degraded by the 26S proteasome (Hershko and Heller, *Biochem. Biophys. Res. Comm.* 128:1079–1086 (1985)). Only protein substrates conjugated to a multi-ubiquitin chain are recognized and degraded by the 26S proteasome (Chau, V. et al., *Science* 243:1576–1583 (1989)). When recombinant UBC4 is added together with Fr.II, multi-ubiquitination of IκBα is reconstituted (FIG. 1, lane 4). As a control, a mock *E.coli* extract or recombinant UBC3 (also called CDC34) did not mediate the ubiquitination of IκBα in conjunction with Fr.II (FIG. 1, lanes 5 and 6). Recombinant human UBC5 (UBCh5) also supported the ubiquitination of IκBα when added together with Fr.II. Therefore, the E2 required for ubiquitination of IκBα in HeLa cell extracts belongs to the UBC4/UBC5 family of E2s. Recently, another member of the UBC4/UBC5 family (E2-F1) has been shown to be required for the degradation of IκBα in vitro (Alkalay, I. et al., *Mol. Cell. Biol.* 15:1294–1301 (1995)). An important implication of these results is that fraction II contains both the kinase and the E3 necessary for the phosphorylation and ubiquitination of IκBα.

Figure 2A:
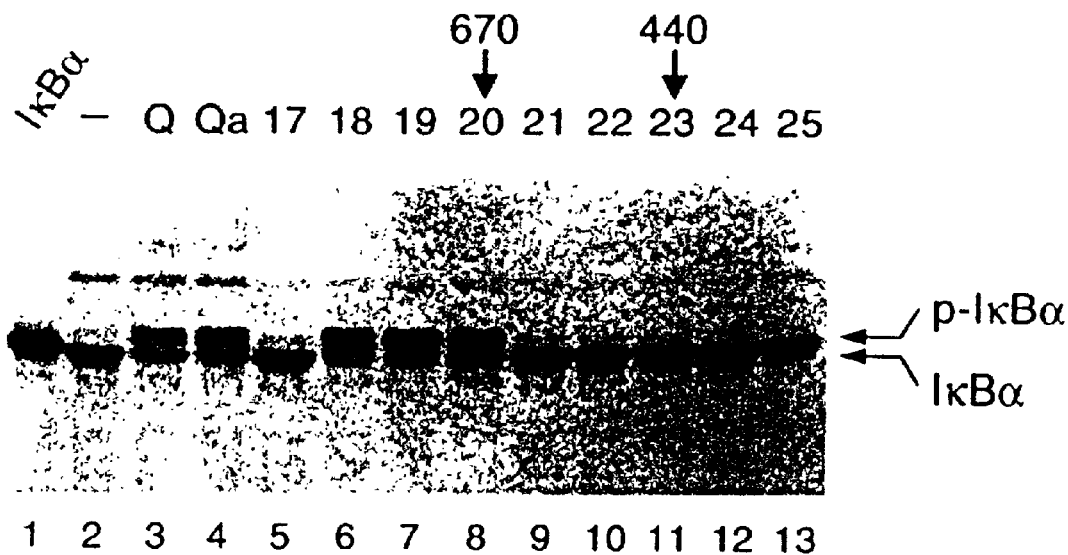
FIGS. 2A–2E are representations of autoradiographs of SDS-PAGE gels demonstrating that the high molecular weight kinase described herein phosphorylates IκBα at serines 32 and 36.

Fraction II was subjected to further purification as a means of identifying the IκBα kinase and E3. To assay the kinase activity, the observation that signal-induced phosphorylation of $^{35}$S-labeled IκBα leads to a reduction in its electrophoretic mobility on SDS-PAGE was taken advantage of (Chen, Z. J. et al., *Genes & Dev.* 9:1586–1597 (1995)). Fraction II was separated by FPLC/monoQ chromatography into five fractions using, isocratic elution with 0.1 M, 0.2M, 0.3M, 0.4M and 0.5M KCl. The IκBα kinase activity was detected in the 0.3M fraction. This fraction was concentrated by ammonium sulfate (40%) precipitation, resuspended and fractionated by size exclusion chromatography using FPLC/Superdex 200 (FIG. 2A). The peak of the IκBα kinase activity eluted in fraction 19, corresponding to an apparent molecular mass of approximately 700 kDa. To rule out the possibility that the large size is due to aggregation, the kinase containing fractions were further fractionated on monoQ ,with a linear gradient of 0.15M–0.4M NaCl, and the peak activity was pooled and resized on Superdex-200.

Figure 2C:
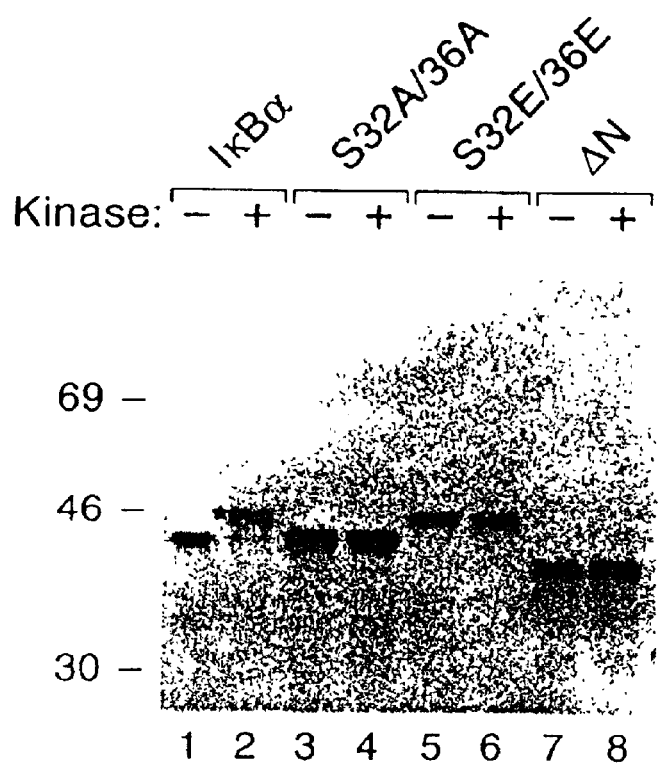
Figure 2B:
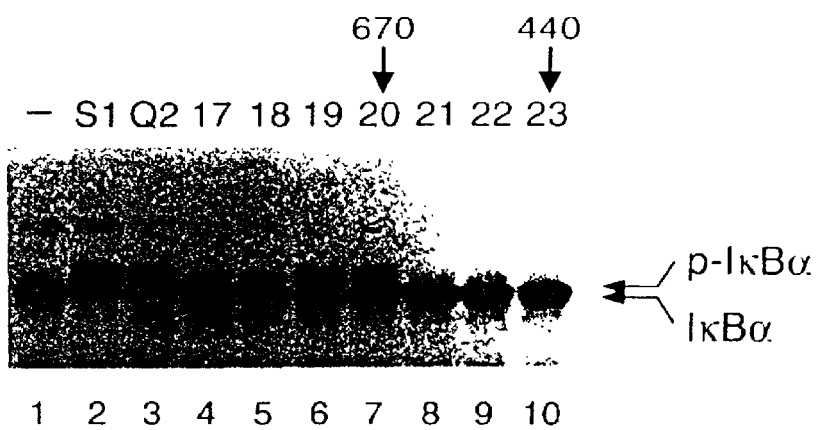

As shown in FIG. 2B, the peak of kinase activity again eluted in fraction 19. Ovalbumin, which was included as a carrier protein, eluted in a fraction corresponding to its expected molecular mass (43 kDa). Thus, the apparent high molecular weight of the kinase is not due to the formation of non-specific aggregates. When the kinase-containing fraction was analyzed on a native polyacrylamide gel, three predominant high molecular weight bands were observed. Although the molecular weights of these complexes cannot be accurately estimated on the native gel system, the bands migrated with mobilities corresponding to molecular weights of approximately 700 kDa, consistent with the size predicted by gel filtration. On SDS-PAGE, these large proteins were separated into distinct multiple lower molecular weight species suggesting that the kinase is a multi-subunit complex. The active Superdex-200 fractions was used to investigate the biochemical requirements for the kinase activity.

A critical test of the specificity of the kinase activity is to determine whether it phosphorylates serine residues 32 and 36 of IκBα. A panel of IκBα mutants was tested including: ΔN (N-terminal truncation at amino acid 72), S32A/S36A (serine to alanine substitutions at residues 32 and 36), and S32E/S36E (serine to glutamic acid substitutions at residues 32 and 36) (Brockman, J. A. et al., *Mol. Cell. Biol.* 15:2809–2818 (1995)). As shown in FIG. 2C, phosphorylation of wild type IκBα resulted in a reduction in the electrophoretic mobility (lane 2). By contrast, incubation of the mutant IκBα proteins with the kinase fraction did not lead to a change in electrophoretic mobility (FIG. 2C, lanes 4, 6, 8). The S32E/36E mutant exhibited a decreased electrophoretic mobility (due to the two negative charges), which was unaffected by the kinase activity.

Figure 2D:
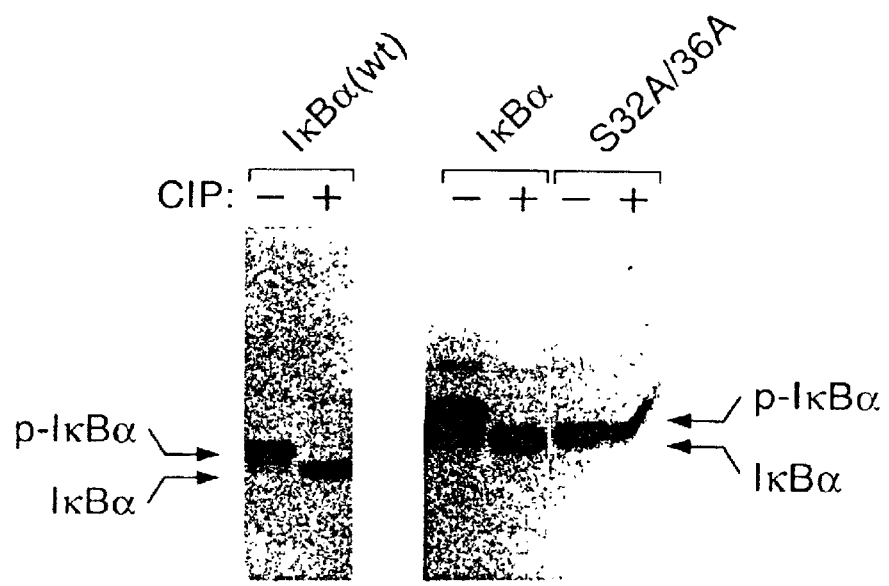

Although the results shown in FIG. 2C strongly suggest that the kinase phosphorylates IκBα at serine residues 32 and 36, there is a remote possibility that these two serine residues function as an "anchor" site for the kinase, and phosphorylation actually occurs elsewhere. To rule out this possibility, the N-terminal fragment of the phosphorylated IκBα was removed with thrombin, which cleaves after residue 62. It was determined whether the N-terminal fragment was still phosphorylated (FIGS. 2D and E). In FIG. 2D, wild type IκBα (lanes 3 and 4) and the S32A/S36A mutant (lanes 5 and 6) were incubated with the kinase fraction and then analyzed before and after treatment with calf intestine alkaline phosphatase (CIP). Since both the wild type and mutant proteins were tagged by a FLAG epitope at their N-termini (Brockman, J. A. et al., *Mol. Cell. Biol.* 15:2809–2818 (1995); Chen, Z. J. et al., *Genes & Dev.* 9:1586–1597 (1995)), wild type IκBα that was not epitope-tagged (lanes 1 and 2) was tested to ensure that the FLAG epitope does not complicate the interpretation of the results.

Figure 2E:
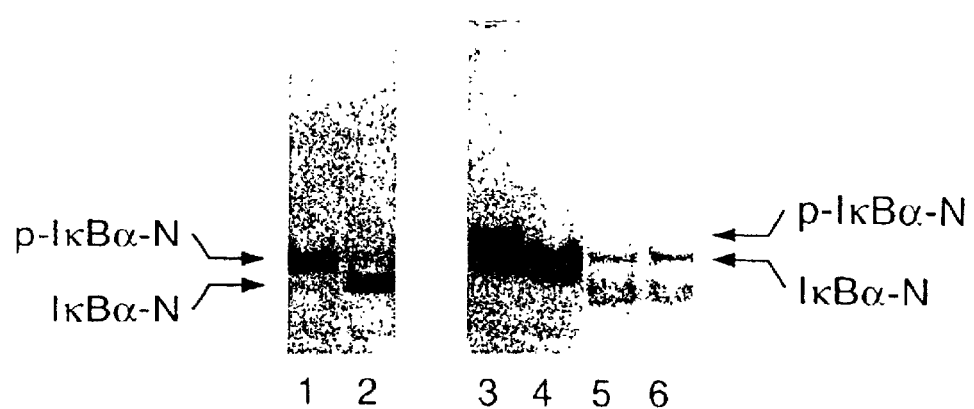

Phosphatase treatment of the phosphorylated wild type IκBα converted the slower migrating form into the faster migrating form (FIG. 2D, lanes 1–4), and this conversion was blocked by phosphatase inhibitors. When the thrombin-cleaved N-terminal fragments from the wild type protein were analyzed on a 16.5% Tris-tricine gel (FIG. 2E), the N-terminal fragments (approximately 8 kDa) were found to contain phosphoryl groups which could be dephosphorylated with CIP (lanes 1–4). Phosphatase treatment did not alter the electrophoretic mobility of either the intact protein or the N-terminal fragment of the S32A/S36A mutant (FIGS. 2D and E, lanes 5 and 6), indicating that this mutant was not phosphorylated at the N-terminus. Since the only residues at the N-terminus of IκBα that can be phosphorylated are serines 32 and 36 (Haskill, S. et al., *Cell* 65:1281–1289 (1991)), it was concluded that phosphorylation of IκBα by the high molecular weight IκBα kinase occurs at serines 32 and 36.

UBC4/UBC5 May Be Required for the Phosphorylation of IκBα

Figure 3A:
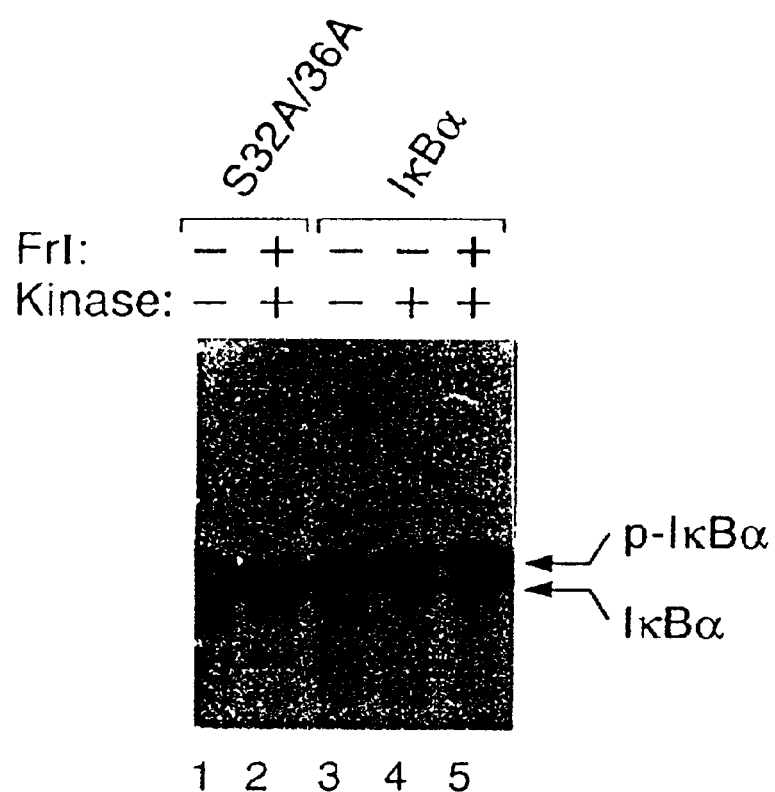
FIGS. 3A–3E are representations of autoradiographs of SDS-PAGE gels demonstrating that under the conditions of the experiment phosphorylation of IκBα by the kinase described herein requires ubc4/ubc5.
Figure 3B:
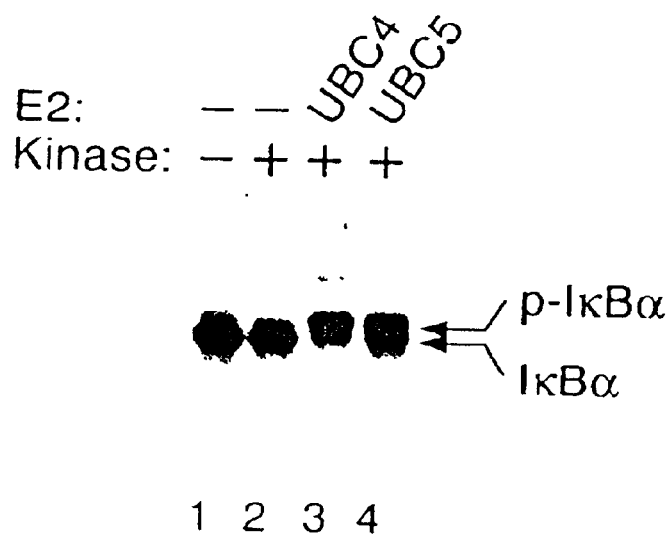
Figure 3C:
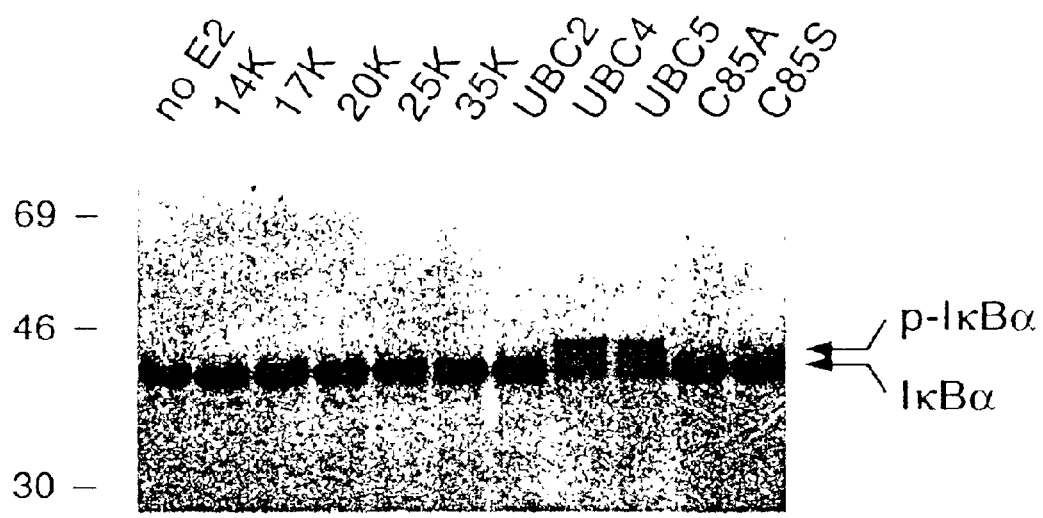
Figure 3D:
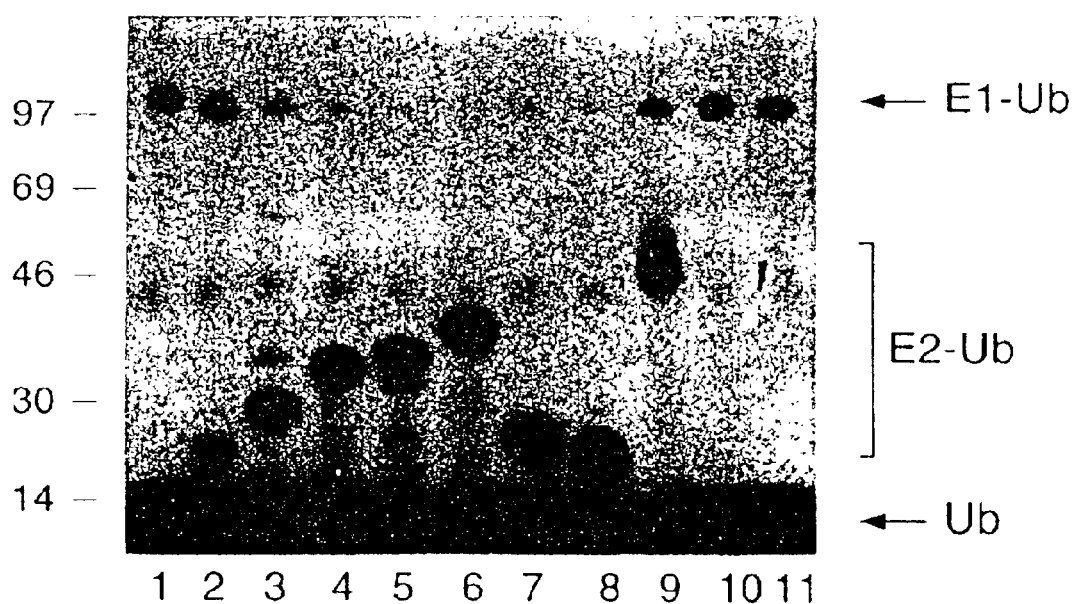

The IκBα phosphorylation assays were initially carried out under the same conditions as the assays for the ubiquitination of IκBα, i.e., fraction I was always added to the reaction. When fraction I was omitted from the reaction, phosphorylation of IκBα was markedly reduced (FIG. 3A, lanes 4 and 5). As expected, fraction I did not stimulate the phosphorylation of the IκBα mutant, S32A/S36A (lanes 1 and 2). The kinase-stimulatory activity of fraction I could be replaced by purified recombinant yeast UBC4 or human UBC5 (GST-UBCh5) (FIG. 3B). The specificity of this E2-stimulatory activity was addressed by testing five other purified E2 proteins from rabbit reticulocytes, including $E2_{14K}$, $E2_{17K}$, $E2_{20K}$, $E2_{25K}$ and $E2_{35K}$. Remarkably, none of these E2s stimulated the kinase activity (FIG. 3C, lanes 2–6). Similarly, recombinant human UBC2 (FIG. 3C, lane 7) and yeast UBC3 also failed to stimulate the kinase activity. All of these E2's form thioester with $^{125}$I-labeled ubiquitin in the presence of E1 and ATP (FIG. 3D). Therefore, among all E2s tested thus far, UBC4/UBC5 have the unique ability to stimulate the IκBα kinase activity.

Figure 3E:
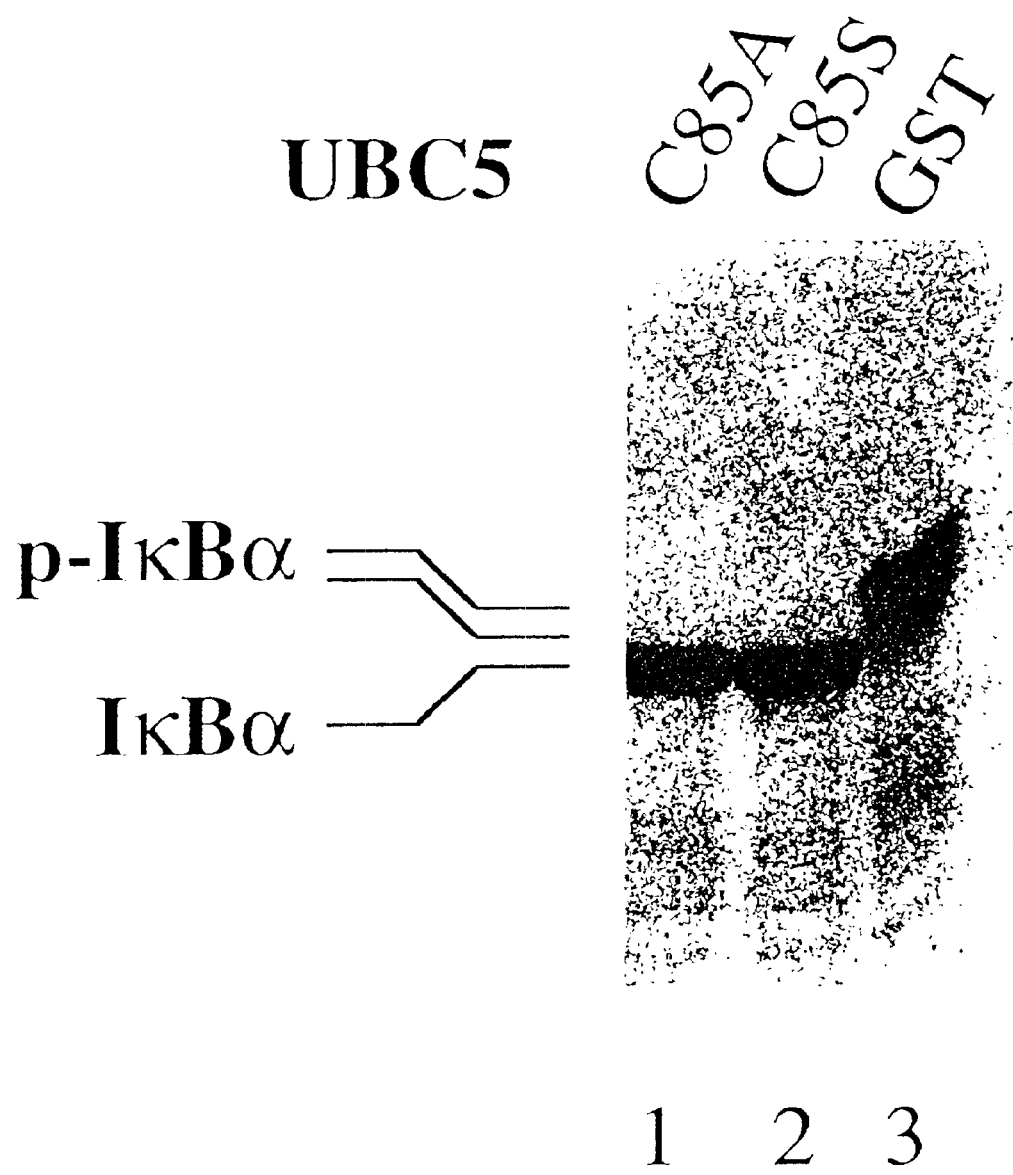

It was next determined whether the catalytic activity of E2 proteins is required for their ability to stimulate the IκBα kinase activity. Specifically, the active site cysteine residue of UBCh5 was substituted to alanine (C85A) or serine (C85S), and analyzed the effects of these substitutions on E2-dependent IκBα phosphorylation. As expected, these two mutants were defective in forming thioesters with $^{125}$I-ubiquitin (FIG. 3D, lanes 10–11). Significantly, they also failed to stimulate the phosphorylation of IκBα by the IκBα kinase (FIG. 3C, lanes 10–11). It was also found that inactivation of UBC4 or UBC5 by N-ethylmaleimide (NEM), resulted in a loss of IκBα kinase stimulatory activity. Finally, when C85A or C85S mutants of GST-UBCh5 were added in large excess (mutant:wild type=20:1) to the phosphorylation reaction, the UBC5 dependent phosphorylation of IκBα was inhibited (FIG. 3E, lanes 1 and 2). As a control, GST had no effect on the phosphorylation of IκBα (lane 3). Thus, the active site mutants of UBC5 appear to function as dominant negative mutants in inhibiting the phosphorylation of IκBα. These results show that under these conditions, the ubiquitin conjugating function of UBC4/UBC5 is required for the phosphorylation of IκBα by the IκBα kinase.

Ubiquitin May Be Required for the Phosphorylation of IκBα

Figure 4A:
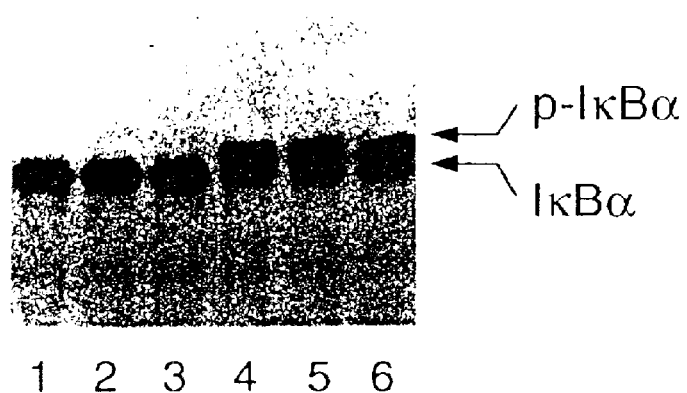
FIGS. 4A–4B are representations of autoradiographs of SDS-PAGE gels demonstrating that under the conditions of the experiment ubiquitin is required for phosphorylation of IκBα by the kinase described herein.

The unusual requirement for catalytically active E2 in the IκBα kinase assay suggested that ubiquitin, which was present in our assay mixture, might also be required. In fact, IκBα phosphorylation was not observed when ubiquitin was not added to the reaction (FIG. 4A, lane 1). However, significant levels of phosphorylation of IκBα was observed in the presence of 1 μM of ubiquitin (lane 4), which is less than the physiological concentration of ubiquitin (10–20 μM; Haas & Bright, J. Biol. Chem. 250:12464–12473 (1985)). The concentration-dependence of the ubiquitin requirement suggests a highly cooperative behavior, consistent with the possibility that multi-ubiquitin chain formation is necessary for IκBα phosphorylation.

Figure 4B:

A number of observations rule out the possibility that the kinase-stimulatory effect of ubiquitin is due to a contaminant in the ubiquitin preparation (Sigma). First, recombinant ubiquitin (both bovine and yeast) expressed in E. coli stimulate the kinase activity; second, when ubiquitin (Sigma) was further purified by FPLC-monoS, the kinase-stimulatory activity co-purified with ubiquitin; third, methylated ubiquitin (MeUb) does not stimulate the kinase activity, but instead competitively inhibits the ubiquitin-dependent phosphorylation of IκBα (FIG. 4B). Previous studies have shown that MeUb is activated by E1, transferred to E2, and then conjugated to protein substrates. However, conjugates containing MeUb cannot be multi-ubiquitinated due to the lack of free lysine residues in MeUb (Hershko & Heller, Biochem. Biophys. Res. Comm. 128:1079–1086 (1985)).

When an E2-Ub thioester is first allowed to form between UBC4 and a low concentration of ubiquitin (2.4 μM), and then mixed with a large excess of MeUb (40 μM), the phosphorylation of UκBα is inhibited (FIG. 4B, lane 4). This inhibition can be reversed by adding a large excess of ubiquitin during, the thioester formation (lane 5). However, if UBC4 and MeUb form a thioester first, followed by the addition of ubiquitin, no phosphorylation of IκBα is observed, even when ubiquitin is in excess (FIG. 4B, lanes 7 and 8). Thus, under these conditions, multi-ubiquitination appears to be required for the kinase activity. Consistent with this possibility, the isopeptidase inhibitor ubiquitin aldehyde enhances the phosphorylation of IκBα in crude extracts. However, this enhancement is not observed with the more purified kinase fractions, presumably due to the absence of contaminating isopeptidases.

Additional Requirements for the Phosphorylation of IκBα

Figure 5A:
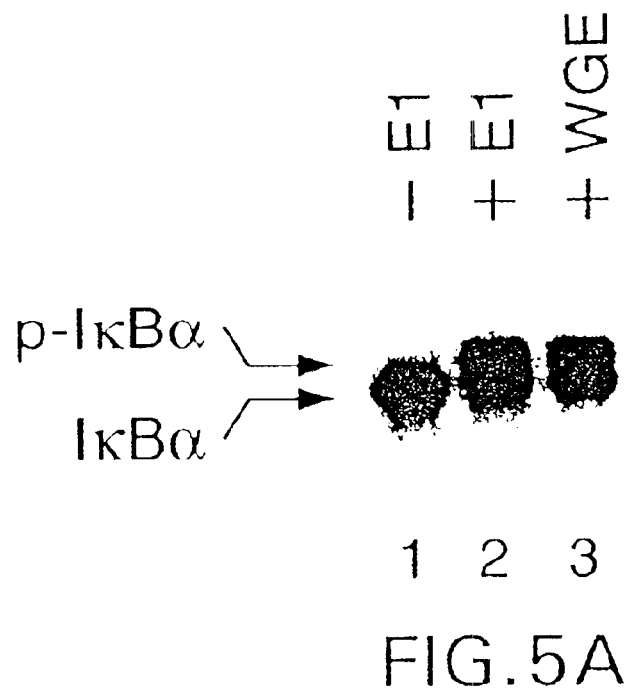
FIGS. 5A–5B are representations of autoradiographs of SDS-PAGE gels demonstrating that under the conditions of the experiment E1 is required for phosphorylation of IκBα by the kinase described herein. There is no requirement for okadaic acid or Rel A.

The UBC4/UBC5 and ubiquitin requirement for the phosphorylation of IκBα prompted us to determine whether E1 is also required for this activity. The IκBα used in these experiments was translated in a wheat germ extract which contains wheat E1. Thus, it was necessary to isolate IκBα from the extract by immunoprecipitation. IκBα was first allowed to associate with recombinant RelA homodimer, and the complex was then precipitated with the antisera against RelA. The immunoprecipitates were used directly as a substrate in the IκBα phosphorylation assay. As shown in FIG. 5A, phosphorylation of IκBα required the addition of E1 or wheat germ extract. This experiment also showed that no other component in the wheat germ extract was required for the phosphorylation of IκBα.

Figure 5B:
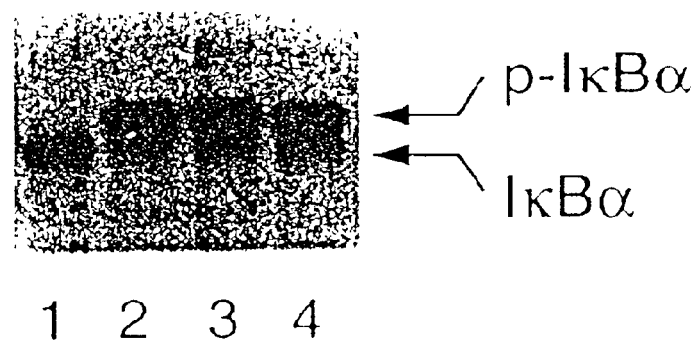

The phosphatase inhibitor okadaic acid is necessary to observe phosphorylation and ubiquitination of IκBα in crude HeLa cell cytoplasmic extracts (Chen, Z. J. et al., Genes & Dev. 9:1586–1597 (1995)). These extracts also contained substantial amounts of rel proteins. Thus, it is possible that IκBα must be in a complex with rel proteins in order to be accurately phosphorylated. For these reasons, all phosphorylation assays described above contain okadaic acid and recombinant RelA homodimers. Although the presence of okadaic acid was necessary to observe IκBα kinase activity during the early stages of kinase purification, it was not required for the activity of the partially purified IκBα kinase (FIG. 5B, lane 4). Thus, an okadaic acid-sensitive phosphatase must have been removed during the purification of IκBα kinase. RelA is not required for the in vitro phosphorylation of IκBα (FIG. 5B, lane 3). This observation is consistent with a recent report that the Drosophila IκB homolog Cactus undergoes signal-induced degradation (and presumably also phosphorylation) in Drosophila embryos lacking the rel family protein Dorsal (Belvin, M. P. et al., Genes & Dev. 9:783–793 (1995)).

A Ubiquitination Event Activates IκBα Kinase

Figure 6A:
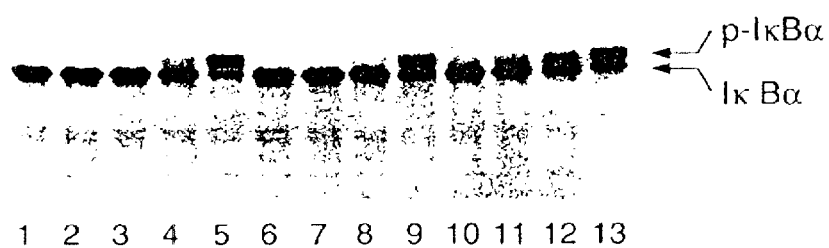
FIG. 6A is a representation of an autoradiograph of an SDS-PAGE gel demonstrating that under the conditions of the experiment IκBα kinase is activated by a prior ubiqutination event. Preincubation of IκBα kinase with ubiquitination enzymes and ubiquitin eliminates the lag phase in the phosphorylation of IκBα.
Figure 6B:
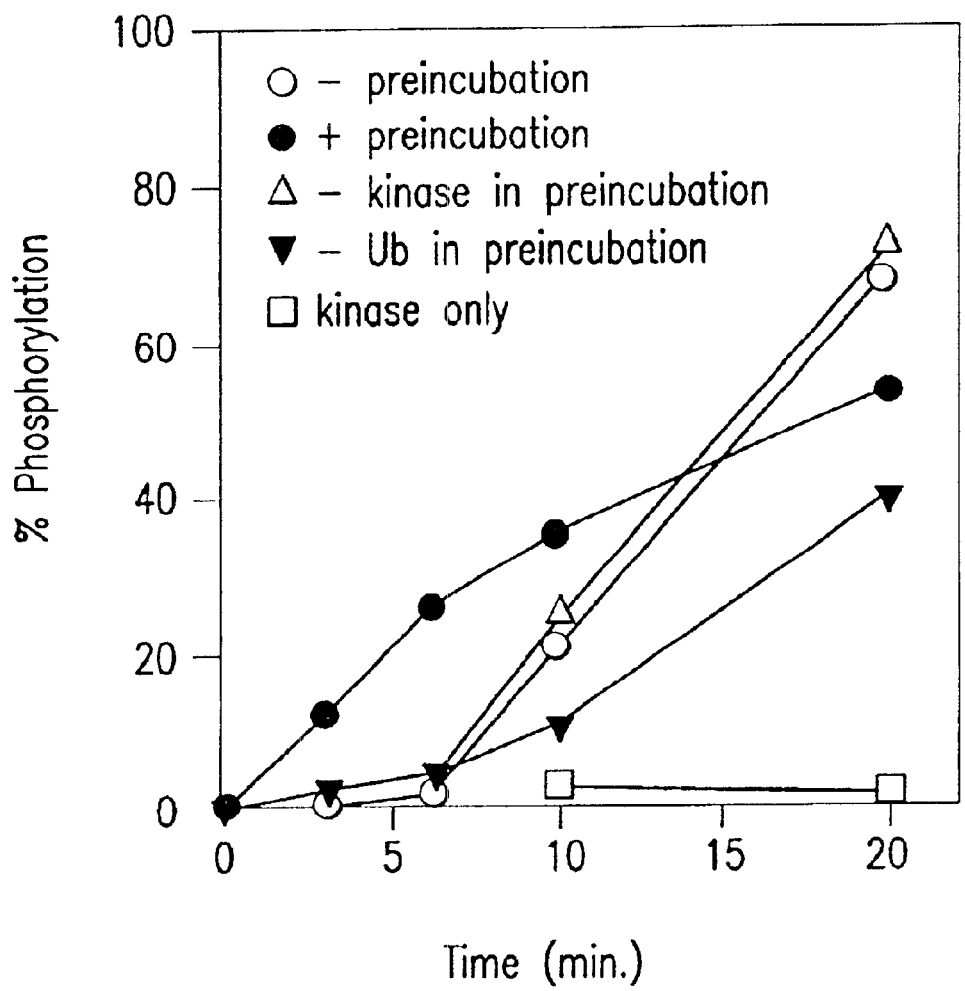
FIG. 6B is a graphical representation of the same data quantitated by PhosphorImager analysis.

Why may phosphorylation of IκBα by the IκBα kinase require E1, UBC4 or UBC5, and ubiquitin? One possibility is that ubiquitination of an as-yet unidentified factor is necessary for the activation of IκBα kinase. This possibility is consistent with the time course of IκBα phosphorylation, which is biphasic: a lag of 6 minutes followed by a burst of IκBα phosphorylation (FIG. 6A, lanes 1–5; FIG. 6B). This kinetic behavior suggests that an additional event precedes kinase activation. To test this possibility, the partially purified IκBα kinase was preincubated with E1, UBC4 and ubiquitin in the presence of ATP at 37° C. for 10 min, and then initiated the phosphorylation reaction b the addition of $^{35}$S-labeled IκBα (FIG. 6A, lanes 10–13; FIG. 6B). Remarkably, the preincubation eliminated the lag, phase of IκBα phosphorylation. When the IκBα kinase was not added to the preincubation mixture (FIG. 6B), or when ubiquitin was omitted from the preincubation mixture (FIG. 6A, lanes 6–9; FIG. 6B), the lag phase of IκBα phosphorylation persisted. The extent of IκBα phosphorylation was reduced slightly when IκBα kinase was included in the preincubation mixture (compare lanes 5, 9, and 13 in FIG. 6A). This is probably due to the instability of IκBα kinase when incubated at 37° C. for an additional 10 minutes. These results strongly suggest that the IκBα kinase was activated during the preincubation period, most likely by a ubiquitination event.

Figure 7A:
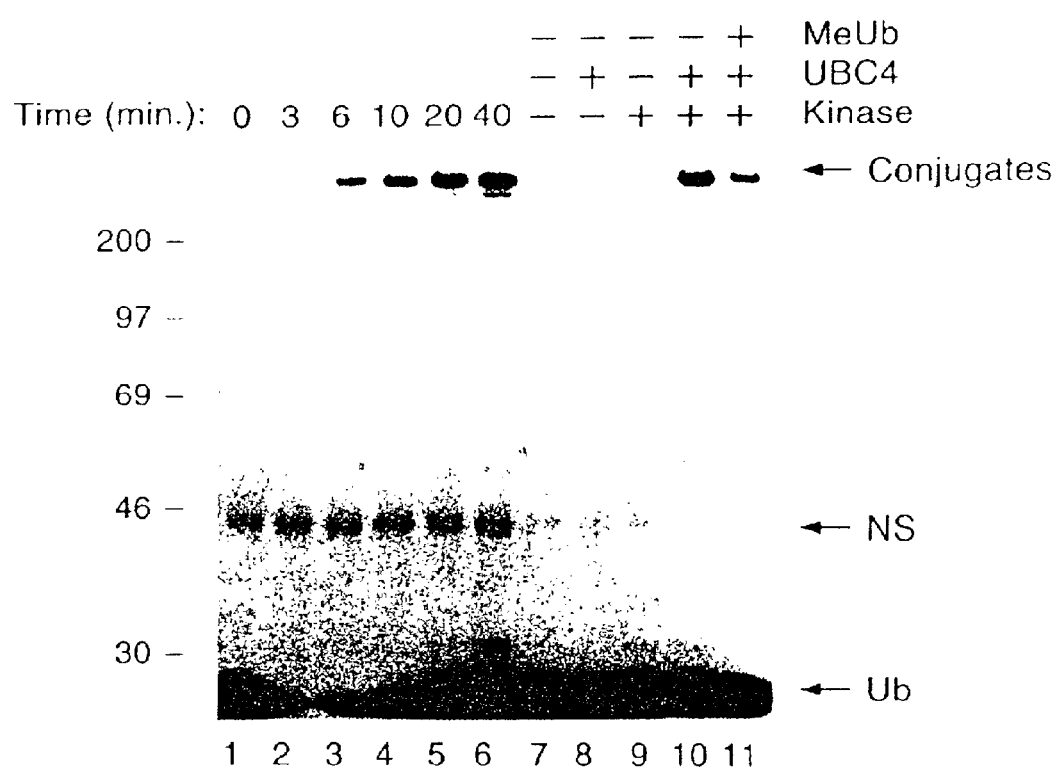
FIG. 7A is a representation of an autoradiograph of an SDS-PAGE gel demonstrating that IκBα kinase is ubiquitinated by ubc4.
Figure 7B:
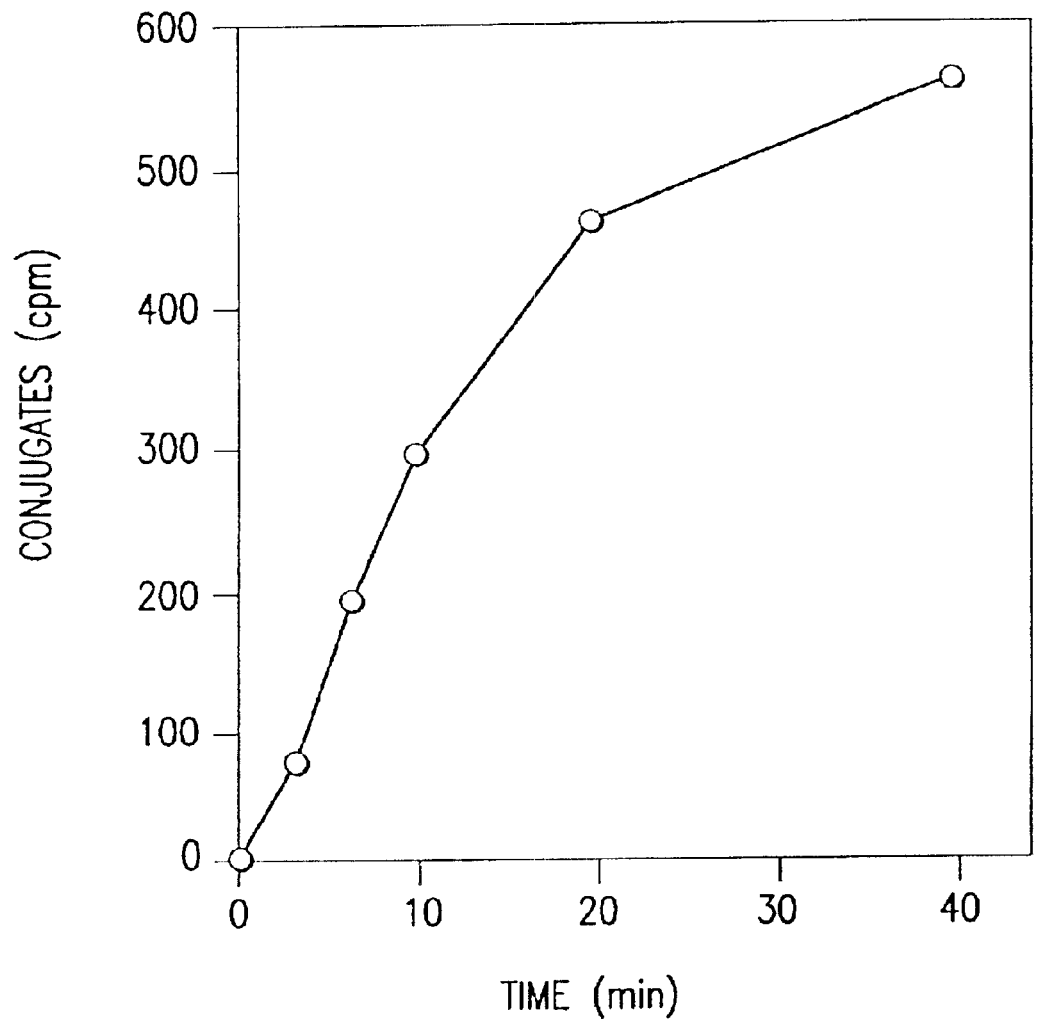
FIG. 7B is a graphical representation of the kinetics of IκBα kinase ubiqutination.

To directly demonstrate that ubiquitination occurs during the preincubation reaction, E1, UBC4, and IκBα kinase were incubated with $^{125}$I-Ub in the presence of ATP at 37° C. As shown in FIG. 7A, a time-dependent accumulation of high molecular weight ubiquitinated conjugates was observed (these conjugates were unable to enter the 5% stacking gel). The kinetics of conjugate accumulation paralleled that of IκBα phosphorylation only when IκBα kinase was preincubated with E1, UBC4 and ubiquitin (compare FIG. 6B and FIG. 7B). This observation is consistent with the idea that formation of these conjugates precedes the phosphorylation of IκBα. Conjugate formation was not observed when either UBC4 or the IκBα kinase was removed from the conjugation reaction (FIG. 7A, lanes 8 and 9). Furthermore, the formation of these conjugates was reduced by approximately 50% by the presence of excess MeUb (lane 11). The complete inhibition of the kinase activity by MeUb observed in the experiment of FIG. 4B, was likely the consequence of allowing the E2 to form a thioester with a large excess of MeUb prior to the addition of ubiquitin. All of these results support the hypothesis that ubiquitination of an unknown factor (factor X, probably as part of the kinase complex) is required for the activation of the IκBα kinase. Since multi-ubiquitination of protein substrates usually requires an E3, the IκBα kinase complex probably contains an E3 activity.

Another example of the coupling of phosphorylation and ubiquitination is provided by the ubiquitination of mitotic cyclins by the cyclosome, a 20S complex that harbors an E3 activity (E3-C; Sudakin, V. et al., *Mol. Biol. Cell* 6:185–198 (1995); King, R. W. et al., *Cell* 81:279–288 (1995)). The activity of E3-C is dependent on cdc2, a cyclin-dependent kinase. The activation of E3-C by cdc2 is indirect, however, since pretreatment of cyclosome with cdc2 abolishes a lag phase in the ubiquitination of cyclins. Therefore, a phosphorylation cascade may be propagated from cdc2 within the cyclosome.

The determination of the role of this kinase in vivo will require the identification and inactivation of the gene(s) encoding the kinase complex. It is interesting in this regard that heat inactivation of a mutant E1 protein results in the accumulation of unphosphorylated IκBα in cells stimulated by IL-1 (Alkalay, I. et al., *Proc. Natl. Acad. Sci. USA* 92:10599–10603 (1995)). By contrast, stimulated cells treated with proteasome inhibitors accumulate both phosphorylated and unphosphorylated IκBα. These observations are consistent with the possibility that E1 is required for both the phosphorylation and degradation of IκBα in vivo.

Ubiquitination, not ubiquitin-dependent degradation, activates the kinase, since proteolytic activity is not required for IκBα phosphorylation in the partially purified system. Furthermore, proteasome inhibitors do not inhibit the phosphorylation of IκBα in vivo (Palombella, V. J., *Cell.* 78:773–785 (1994), Traenckner, E. B.-M. et al., *EMBO J.* 13:5433–56441 (1994); Brockman, J. A. et al., *Mol. Cell. Biol.* 15:2809–2818 (1995); Chen, Z. J. et al., *Genes & Dev.* 9:1586–1597 (1995)) or in vitro (Scherer, D.C. et al., *Proc. Natl. Acad. Sci. USA* 92:11259–11263 (1995)). In addition, the activation of the IκBα kinase in vitro correlates with the accumulation of multi-ubiquitinated conjugates that are not degraded (FIGS. 6 and 7). Finally, in contrast to methylated ubiquitin in which all seven lysine residues are blocked by methylation, a ubiquitin mutant (K48R), which cannot form multi-ubiquitin chains through K48, is still capable of stimulating the IκBα kinase activity. K48-linked multi-ubiquitin chains are thought to be specifically recognized by the 26S proteasome (Chau, V. et al., *Science* 243:1576–1583 (1989)). However, multi-ubiquitin chains with linkages through lysine residues other than K48 also exist in cells and they play important roles in stress response (Arnason & Ellison, *Mol. Cell. Biol.* 14:7876–7883 (1994)) and DNA repair (Spence, J. et al., *Mol. Cell Biol.* 15:1265–1273 (1995)). It is possible that different multi-ubiquitin chain configurations may be involved in the regulation of protein activity, rather than proteolysis (Arnason & Ellison, *Mol. Cell. Biol.* 14:7876–7883 (1994)).

Although a component of the partially purified kinase is ubiquitinated in vitro when the kinase is activated by ubiquitination, the target of ubiquitination has not been identified. This target could be the kinase or an essential component of the kinase complex. This covalent modification of the IκBα kinase complex could activate the kinase by inducing a conformational change, or ubiquitination could inactivate a kinase inhibitor. Several cyclin-dependent kinase (CDK) inhibitors, such as P40$^{SIC1}$ (Schwob, E. et al., *Cell* 79:233–244 (1994)); Farl (McKinney, J. D. et al., *Gene & Dev.* 7:833–843 (1993)), and p27 (Pagano, M. et al., *Science* 269:2682–685 (1995)) have been shown to be targets of the ubiquitin-proteasome pathway, but none of these appear to be inactivated by ubiquitination alone. Other examples of proteins whose activities might be regulated by ubiquitination are receptor associated kinases (reviewed by Ciechanover, A., *Cell* 79:13–21 (1994)). For instance, it has been reported that the antigen-induced ubiquitination of the immunoglobulin E receptor (FCERI) is not dependent on the prior receptor phosphorylation, but is linked to the activation of the molecule (Paolini & Kinet, *EMBO J.* 12:779–786 (1993)). Disengagement of antigen results in rapid deubiquitination. It is not known whether ubiquitination serves to trigger receptor down-regulation by proteolysis, or whether it carries out other regulatory functions.

A ubiquitination event may be required for the activation of the IκBα kinase in vitro (FIG. 8), but it has not been determined whether this event is regulated in vivo. It is possible that the kinase activity is constitutive in vivo and IκBα phosphorylation is controlled by inactivation of a phosphatase. Alternatively, the kinase activity is regulated by signals that induce NF-κB. The former possibility is consistent with the observation that okadaic acid is not required to activate the kinase activity in our most purified fractions (FIG. 5B). In addition, the IκBα kinase was purified from unstimulated HeLa cell extracts. However, HeLa cells may have a relatively high level of "constitutive" kinase activity compared to normal (untransformed) cells. NF-κB can be activated by okadaic acid alone in transformed cells, whereas an additional signal such as $H_2O_2$ is required to activate NF-κB in primary cells (Menon, S. D. et al., *J. Biol. Chem.* 268:26805–26812 (1993)). It is also possible that the state of phosphorylation of IκBα in vivo is determined by a balance between kinase and phosphatase activities, and a small upregulation of the kinase would be sufficient to target IκBα to the degradation pathway. It may not be possible to mimic these conditions in vitro where ubiquitination enzymes and ubiquitin are in large excess.

Most, if not all, of the known NF-κB inducers result in oxidative stress through the generation of reactive oxygen intermediates (ROIs, Schmidt et al., 1995). ROIs could affect the phosphorylation of IκBα directly by activating IκBα kinase(s) or by inactivating IκBα phosphatase(s). Alternatively, the effect of ROIs on IκBα phosphorylation may be indirect. For example, ROIs might trigger a stress response, which would in turn lead to the phosphorylation of IκBα.

A possible connection between ROIs and the ubiquitin-proteasome pathway is provided by certain proteins (i.e., RNase A) in which mild oxidation of methionine residues greatly increases their susceptibility to ubiquitination (Hershko, A. et al., *J. Biol. Chem.* 261:11992–11999 (1986)). Similarly, oxidation of glutamine synthetase in *E. coli* at a single histidine residue by $H_2O_2$ results in the inactivation and degradation of this enzyme (Levine, R. L., *J. Biol. Chem.* 258:11823–11827 (1983); Fucci, L. et al., *Proc. Natl. Acad. Sci. USA* 80:1521–1525 (1983)). Thus, one model of NF-κB signal transduction is that NF-κB inducers cause oxidative stress, thus enhancing the multi-ubiquitination of a component of the IκBα kinase, which leads to the phosphorylation of IκBα at specific sites.

If the IκBα kinase complex is regulated by ROIs, the oxidative target could be the kinase, the E3 or other components of the ubiquitination machinery. It seems unlikely, however, that E2s are the targets of ROIs. The activity of UBC4/UBC5 is generally considered to be constitutive, though the synthesis of the proteins can be up-regulated in response to stress (Seufert & Jentsch, *EMBO J.* 9:543–550 (1990)). Since the phosphorylation of IκBα occurs within minutes following stimulation, and it does not require new protein synthesis, it is unlikely that phosphorylation of IκBα is regulated a the level of UBC4/UBC5 synthesis. These E2s alone probably do not determine substrate specificities, since they participate in the ubiquitination of a variety of proteins. Instead, these E2s function in conjunction with specific E3s to recognize target proteins. The specific recognition of phosphorylated IκBα probably requires an E3 (E3y, FIG. 8), which remains to be identified.

Figure 8:
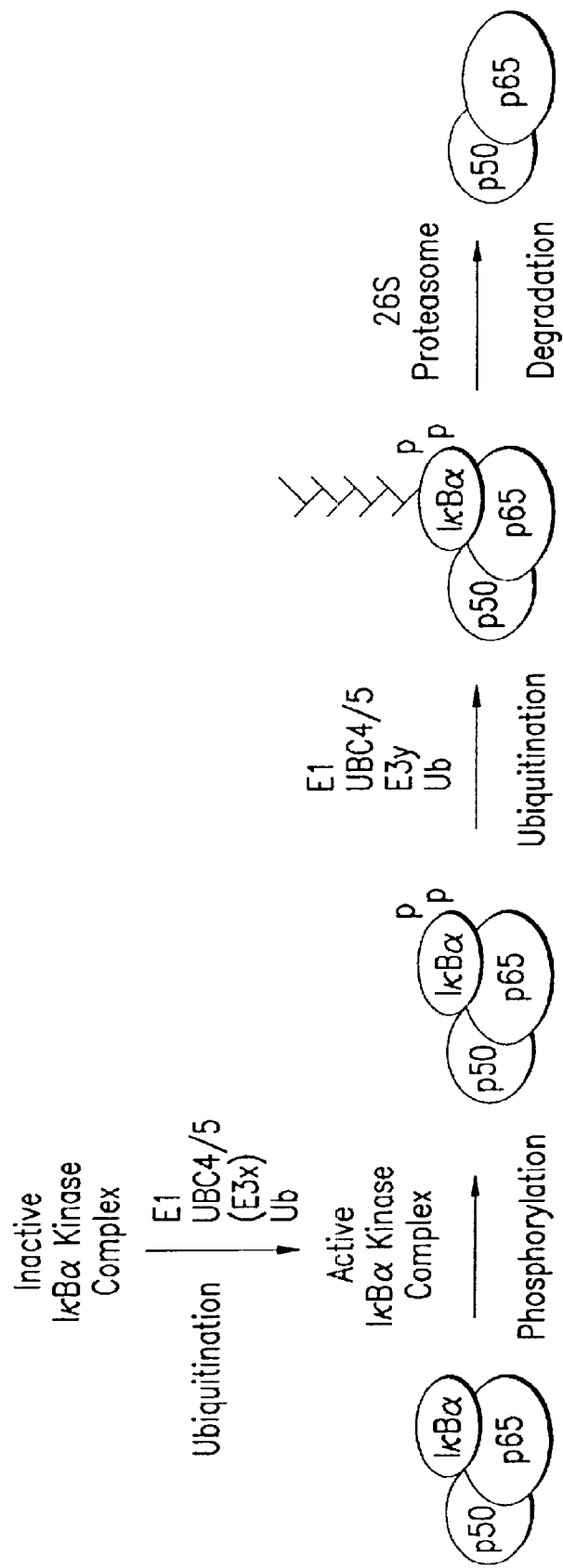
FIG. 8. Schematic representation of the steps involved in IκBα degradation. When the kinase is activated by ubiquitination, ubiquitination is required both for activation of IκBα kinase and for targeting of IκBα for degradation by the proteasome.

Thus, here it is shown that an ubiquitination event may be required for the activation of an IκBα kinase, which phosphorylates IκBα at serines 32 and 36. This two-step ubiquitination pathway for IκBα degradation is illustrated in FIG. 8. The ubiquitination of the IκBα kinase does not require an exogenous E3, suggesting that the IκBα kinase complex possesses an E3 activity ($E3_x$, FIG. 8). The activated kinase then phosphorylates IκBα, thus targeting the inhibitor to the ubiquitin proteasome pathway. The E3 required for the second ubiquitination event ($E3_y$) may be distinct from $E3_x$ since the partially purified kinase is not capable of ubiquitinating IκBα in the presence of E1, UBC4/UBC5 and Ub.

Not only is IκBα phosphorylated in response to a variety of extracellular signals, but a basal level of phosphorylation is also observed. The basal phosphorylation sites have been mapped to the C-terminal casein kinase II (CKII) sites in the PEST region of IκBα, and the Ser-293 is the preferred site of phosphorylation (Barroga, C. F. et al., *Proc. Natl. Acad. Sci. USA* 92:7637–7641 (1995); Kano, K. et al., *J. Biol. Chem.* 270:27914–27919 (1995)). Casein kinase II and a 42 kDa kinase (probably similar to casein kinase II) binds to IκBα and catalyzes the basal phosphorylation of IκBα in vitro. However, deletion of a C-terminal region of IκBα that includes the PEST sequence, or mutation of the basal phosphorylation sites does not prevent the inducible phosphorylation of IκBα (Brown, K. et al., *Science* 267:1485–1491 (1995); Brockman, J. A. et al., *Mol. Cell. Biol.* 15:2809–2818 (1995); Traenckner, E. B.-M. et al., *EMBO J.* 14:2876–2883 (1995); Whiteside, S. T. et al., *Mol. Cell. Biol.* 15:5339–5345 (1995); Verma, I. M. et al., *Genes & Dev.* 9:2723–2735 (1995)). Consistent with this result, it was found that deletion of the C-terminal 75 amino acids of IκBα does not prevent the kinase described here from phosphorylating this mutant. On the other hand, induced degradation of IκBα is hindered by the deletion of C-terminal PEST sequence (Brown, K. et al., *Science* 267:1485–1491 (1995); Rodriguez, M. S. et al., *Mol. Cell. Biol.* 15:2413–2419 (1995); Whiteside, S. T. et al., *Mol. Cell. Biol.* 15:5339–5345 (1995)). This may not be due to the lack of basal phosphorylation, since the IκBα mutant in which all five CKII sites at the C-terminus are mutated to alanine is still degraded upon TNFα stimulation (reviewed by Verma, I. M. et al., *Genes & Dev.* 9:2723–2735 (1995)). Thus, the role of the C-terminal PEST sequence, if any, in the induced degradation of IκBα remains to be established.

IκBα Kinase Activity is Inducible by TNF-α

Figure 10A:
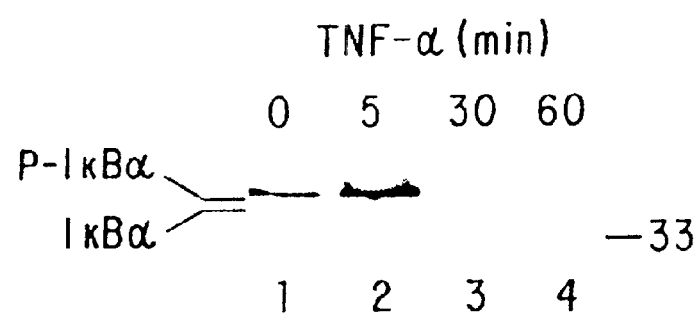
FIGS. 10A–10D are representations of autoradiographs of SDS-PAGE gels demonstrating that IκBα kinase activity is inducible and that it is activated coordinately with JNK activation.
Figure 10B:
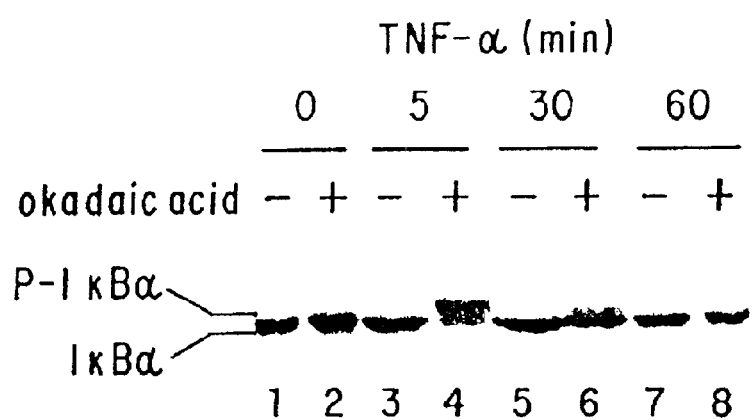

Previous studies left open the question of whether the IκBα kinase is regulated by inducers of NF-κB. In those studies, the IκBα kinase was detected as an apparently constitutive activity in S100 cytoplasmic extracts prepared from uninduced HeLa cells using the hypotonic lysis procedure of Dignam, J. D. et al., *Nucl. Acids Res.* 11:1475–1489 (1983) (Chen, Z. J. et al., *Cell* 84:853–862 (1996)). Using an alternative method for preparing cytoplasmic extracts (a rapid lysis procedure detailed supra), the IκBα kinase is found to be inducible by TNF-α. HeLa cells were treated with TNF-α for differing lengths of time, and the rapid lysis extracts assayed for the presence of endogenous IκBα by Western blotting and for IκBα kinase activity by incubation with exogenous $^{35}$S-labeled IκBα in the presence of okadaic acid (FIGS. 10A and 10B). In these and all subsequent experiments, okadaic acid is employed strictly as a phosphatase inhibitor (i.e., to preserve the phosphorylated IκBα species) rather than as an inducer of IκBα phosphorylation (Thevenin, C. et al., *New Biol.* 2:793–800 (1990); Traenckner, E. B.-M. et al., *EMBO J.* 14:2876–2883 (1995)). Consistent with previous results (Henkel, T. et al., *Nature* 365:182–185 (1993); Mellits, K. H. et al., *Nucl. Acids Res.* 21:5059–5066 (1993)), extracts from uninduced HeLa cells contain hypophosphorylated IκBα (FIG. 10A, lane 1), but after only 5 min of TNF-α treatment a significant portion of the endogenous IκBα is phosphorylated (as revealed by the slower migrating IκBα species, lane 2). After 30 min of treatment, virtually all of the IκBα is degraded (lane 3). Parallel assays with the same extracts reveal that the IκBα kinase activity is absent in uninduced cells (FIG. 10B, lane 2) (activity is weakly detectable when higher concentrations of these extracts are employed). However, after exposure of cells to TNF-α for only 5 min, IκBα kinase activity can be readily detected, as evidenced by the slower-migrating IκBα species (lane 4). Fractionation of these extracts by gel filtration reveals that the TNF-α inducible IκBα kinase activity resides in a large (approximately 700 kDa) complex. Interestingly, this activity persists and is present after 30 min of TNF-α induction (lane 6), a time at which the endogenous IκBα has been degraded (FIG. 10A, lane 3). IκBα kinase activity is essentially absent at 60 min (FIG. 10B, lane 8). It is formally possible that the IκBα kinase activity is constitutive and that TNF-α treatment simply results in the inactivation of a phosphatase in the extract that dephosphorylates IκBα. To address this possibility, the same extract were incubated with $^{35}$S-labeled IκBα in the absence of okadaic acid (FIG. 10B, lanes 1, 3, 5, and 7). Under these conditions, the IκBα mobility shift is completely abolished (for example, compare lanes 3 and 4). Thus, the effects of TNF-α treatment cannot be accounted for solely by inactivation of an okadaic acid-sensitive IκBα phosphatase, implying that TNF-α treatment induces IκBα kinase activity. Furthermore, the rapid induction of IκBα kinase activity correlates with the rapid appearance of the phosphorylated form of IκBα.

Coordinate Activation of IκBα Kinase and JNK Activities in Vitro

Figure 10C:
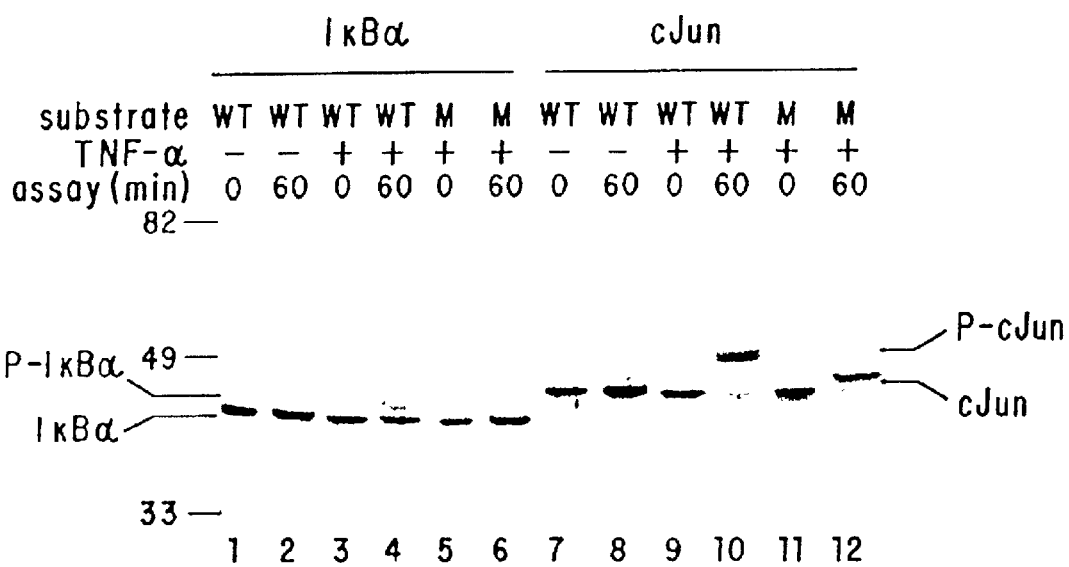
Figure 10D:
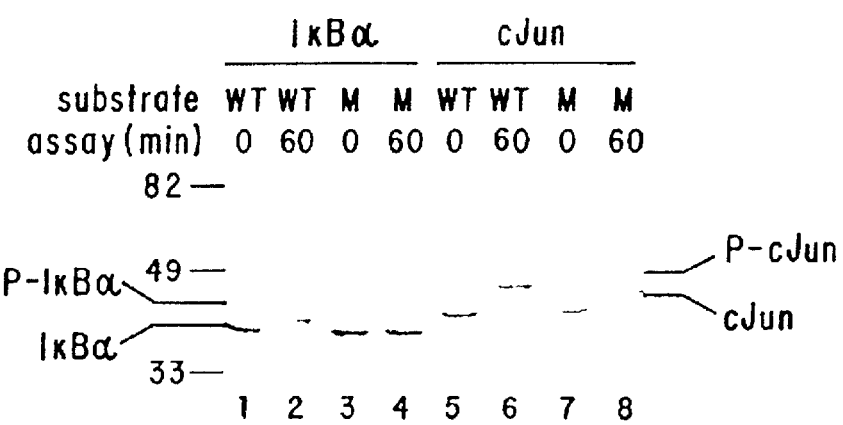

TNF-α treatment also leads to the activation of c-Jun by JNK (Hibi, M. et al., *Genes & Dev.* 7:2135–2148 (1993)). Experiments were carried out to determine whether the IκBα kinase and JNK are coactivated in extracts from TNF-α-treated cells. Cytoplasmic extracts from uninduced and TNF-α-induced HeLa cells were incubated with in vitro translated, $^{35}$S-labeled IκBα or c-Jun, and the proteins fractionated by SDS-PAGE (FIG. 10C). As before, IκBα kinase activity is detected in extracts from TNF-α-induced cells but not in those from uninduced cells (compare lanes 2 and 4). The specificity of phosphorylation is indicated by the fact that the S32A/S36A mutation in IκBα completely abolishes the IκBα shift (lane 6). Similarly, extracts from TNF-α-induced cells show JNK activity, as evidenced by the appearance of a c-Jun species with markedly reduced mobility (compare lanes 9 and 10). The observed shift is a result of JNK activity, since amino acid substitutions at the sites of JNK phosphorylation (S63A/S73A) in c-Jun abolish this shift (lane 12). A distinct shift is observed with the c-Jun mutant, suggesting that JNK may phosphorylate c-Jun at residues other than Ser-63 and -73. Importantly, extracts from uninduced cells show no significant NIK activity (lane 8). Thus, both the IκBα kinase and JNK activities are activated in the rapid lysis extracts prepared from TNF-α-treated, but not untreated, cells.

By contrast, the IκBα kinase activity is readily detected in S100 cytoplasmic extracts prepared from unstimulated HeLa cells using the hypotonic lysis procedure (Chen, Z. J. et al., *Genes & Dev.* 9:1586–1597 (1995)). It is possible that stress pathways are activated by this procedure, since another form of osmotic stress, hyperosmolar shock, has been shown to be an efficient activator of the JNK pathway (Galcheva-Gargova, Z. et al., *Science* 265:806–808 (1994)). Indeed, both the IκBα kinase and the JNK activities were detected when the S100 extracts were incubated for 60 min (FIG. 10). A time-dependent activation of JNK was detected when the S100 extracts were incubated and then examined by an in-gel kinase assay employing the JNK substrate ATF-2. Thus, both the JNK and IκBα kinase may be activated during incubation of the S100 extracts, possibly owing to the hypotonic lysis conditions.

MEKK1 Activates NF-κB in Vivo

Figure 11A:
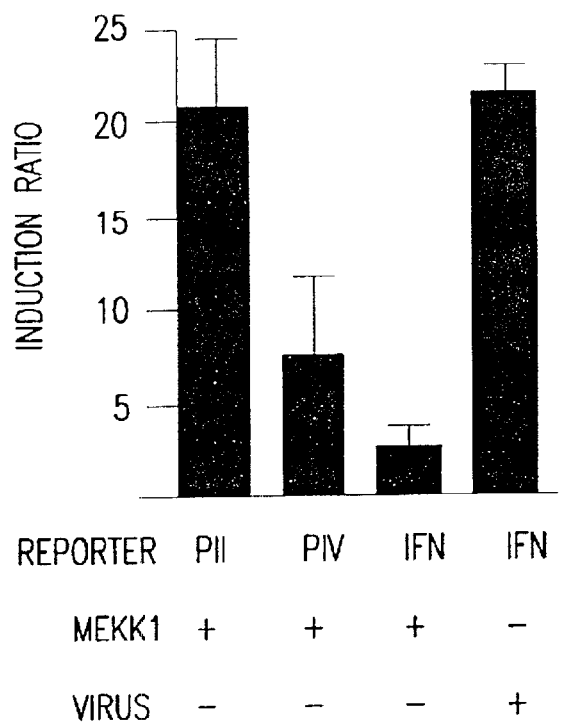
FIGS. 11A–11D are graphical representations of chloramphenicol acyl transferase (CAT) reporter activity, demonstrating that MEKK1 is required for TNF-α induction of NF-κB-dependent gene products.

Transient transfection studies were conducted to examine the relationship between the activation of the IκBα kinase and JNK in vivo. The IFN-β enhancer contains multiple positive regulatory domains (PRDs) that bind distinct transcription factors, including NF-κB (PRDII) and AFT-2/c-Jun (PRDV) (reviewed in Thanos, D. et al. *Cold Spring Harbor Sump. Quant. Biol.* 58:73–81 (1993)). HeLa cells were transfected with reporters linked to either two copies of PRDII (PII), six copies of PRDIV (PIV), or the intact IFN-β enhancer (IFN), which includes these as well as other PRDs, and either an expression vector for MEKK1 or an expression vector alone. Note that in these and all subsequent experiments, MEKK1 and MEKK1Δ refer to the 672 and 321 residue C-terminal fragments, respectively, of the full-length molecule (for discussion, see Xu, S. et al., *Proc. Natl. Acad. Sci. (USA)* 93:5291–5295 (1996)). Both kinases are constitutively active and indistinguishable in transfection studies. As expected, MEKK1 activates the reporter linked to a multitimer of PRDIV (FIG. 11A), which binds to either an AFT-2 homodimer or an AFT-2/c-Jun heterodimer (Du, W. and Maniatis, T., *Cell* 74:887–898 (1993)). Both AFT-2 and c-Jun contain transcriptional activation domains that are phosphorylated by the JNK pathway (Gupta, S. et al., *Science* 267:389–393 (1995)). Importantly, MEKK1 also activates the PRDII reporter. MEKK1 does not activate all promoters, since its effect on a reporter gene containing the intact IFN-β enhancer is only marginal. This enhancer contains additional PRDs that bind factors other than NF-κB or ATF-2/c-June (see Thanos, D. et al. *Cold Spring Harbor Sump. Quant. Biol.* 58:73–81 (1993)). As expected, the IFN-β enhancer is effectively activated by virus infection, which activates all of the PRDs. Thus, MEKK1 can activate both ATF-2/c-Jun and NF-κB in vivo.

Figure 11B:
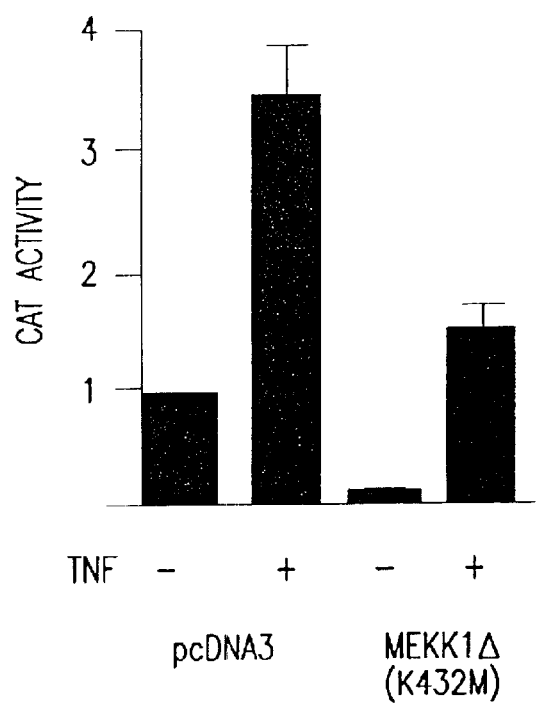
Figure 11C:
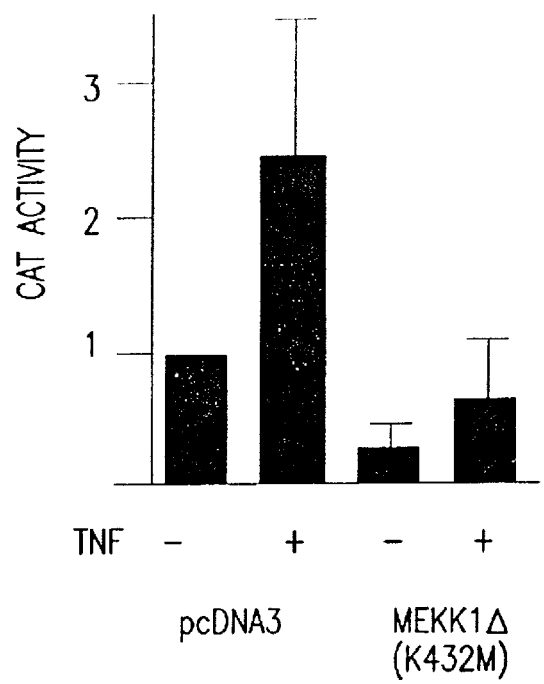
Figure 11D:
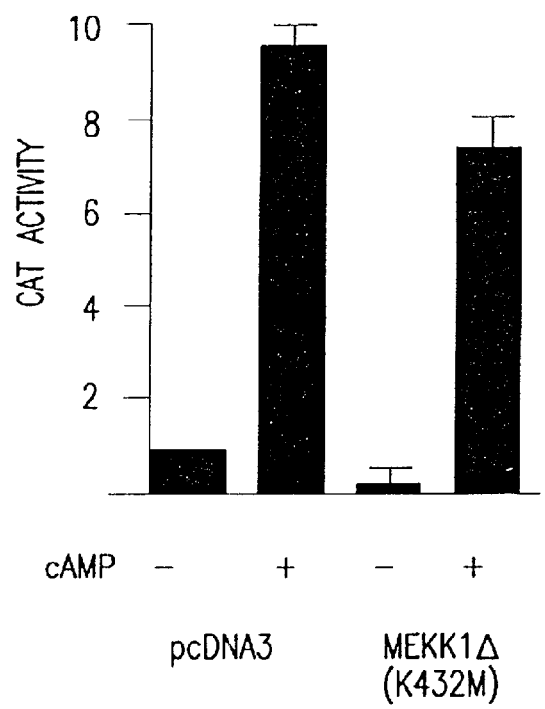

To examine whether MEKK1 plays a role in the activation of NF-κB in response to TNF-α, HeLa cells were transfected with a PRDII reporter and expression vector for catalytically inactive (K432M) MEKK1Δ, or empty expression vector. Some cells were then stimulated with TNF-α, and subsequently all cells were harvested and examined for reporter gene activity. As expected, TNF-α activates the PRDII reporter efficiently (FIG. 11B). By contrast, the mutant MEKK1Δ (K432M) inhibits both the basal and TNF-α-induced activity of this reporter, thus behaving as a dominant negative inhibitor, as has also been shown by Hirano, M. et al., *J. Biol. Chem.* 271:13234–13238 (1996)). Similar results are observed in L929 cells (FIG. 11C). As a negative control, cAMP activation of a cAMP response element reporter is not significantly affected by dominant negative MEKK1Δ (FIG. 11D). These results suggest that MEKK1 plays a role in TNF-α activation of NF-κB.

MEKK1 Activation of NF-κB Occurs Through Site-Specific Phosphorylation of IκBα

Numerous stimuli that activate NF-κB have been shown to induce site-specific phosphorylation of IκBα at Ser-32 and -36 (Brockman, J. A. et al., *Mol. Cell. Biol.* 15:2809–2818 (1995); Brown, K. et al., *Science* 267:1485–1491 (1995); Traenckner, E. B.-M. et al., *EMBO J.* 14:2876–2883 (1995)). Experiments were therefore conducted to examine whether MEKK1 induces this same phosphorylation. HeLa cells were trasnfected with expression vectors for Flag-tagged wild-type or mutant (S32A/S36A) IκBα, and an expression vector for MEKK1 or the expression vector alone. IκBα was then immunoprecipitated with anti-Flag antibodies, and then visualized by Western blotting using anti-IκBα antibodies. MEKK1 induces the appearance of an IκBα species with reduced mobility compared to that isolated from uninduced cells (FIG. 12A, lane 2). This species is sensitive to treatment with calf intestinal alkaline phosphatase (compare lanes 2 and 6), consistent with its being a phosphorylated form of IκBα. Most importantly, ser-to-Ala mutations at residues 32 and 36 of IκBα abolish this species (lane 4). Thus, MEKK1 induces site-specific phosphorylation of IκBα at Ser-32 and -36.

MEKK1 Coordinately Activates the IκBα Kinase and JNK in Vitro

Figures 13A, 13B:
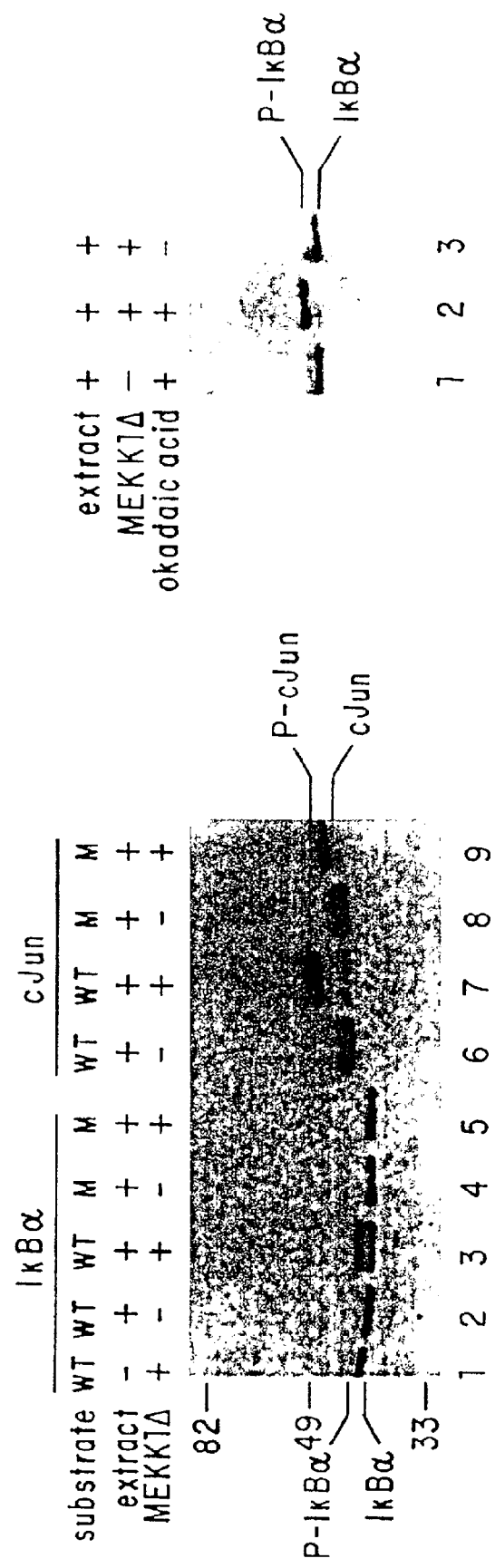

The transfection data show that MEKK1 expression leads to the site-specific phosphorylation of IκBα. To investigate the possibility that MEKK1 activates the IκBα kinase, cytoplasmic extracts were prepared from uninduced HeLa cells by the rapid lysis procedure and then treated with recombinant MEKK1Δ. In the absence of MEKK1Δ, these extracts show no significant site-specific IκBα kinase of JNK activity when incubated with in vitro-translated, $^{35}$S-labeled IκBα or c-Jun, respectively (FIG. 13A, lanes 2 and 6). By contrast, when recombinant MEKK1Δ was added to the extract, site-specific phosphorylation of c-Jun was observed (compare lanes 7 and 9). Importantly, site-specific IκBα kinase activity was also observed (compare lanes 3 and 5), but MEKK1Δ alone fails to induce this site-specific phosphorylation (lane 1). To rule out the possibility that MEKK1Δ inactivates an IκBα phosphatase, extracts were incubated with MEKK1Δ in the absence of presence of the phosphatase inhibitor okadaic acid (FIG. 13B). In the absence of okadaic acid, the MEKK1Δ-induced IκBα shift is largely abolished (compare lanes 2 and 3). Thus, the effects of MEKK1Δ cannot be accounted for solely by the inactivation of an okadaic acid-sensitive IκBα phosphatase, implying that MEKK1Δ activates the IκBα kinase. Thus, MEKKΔcoordinately activates the IκBα kinase and JNK pathways in cytoplasmic extracts.

MEKK1 Directly Activates the IκBα Kinase

In the JNK pathway, MEKK1 phosphorylates and activates MK4, which, in turn, activates JNK. It is therefore possible that IκBα could be a substrate for MEKK1, MKK4, or JNK. When expressed as recombinant proteins, however, neither MKK4 nor JNK1 phosphorylated IκBα, with appropriate control experiments demonstrating that these proteins were enzymatically active. MEKK1Δ did phosphorylate IκBα directly; however, the degree of phosphorylation was over 10-fold less than that seen with MKK4 as a substrate, and, as shown below, MEKK1Δ does not phosphorylate IκBα at Ser-32 or -36. In addition, recent experiments indicate the IκBα kinase activity resides in a large, approximately 700 kDa, multiprotein complex (Chen, Z. J. et al., Cell 84:853–862 (1996)), and Western blotting of this complex fails to reveal the presence of MEKK1, MKK4, JNK1, or JNK2. A reasonable hypothesis, therefore, is that MEKK1 or one of the downstream kinases phosphorylates IκBα indirectly by stimulating the IκBα kinase.

To distinguish between these possibilities, MEKK1Δ was incubated with purified, ubiquitination-inducible IκBα kinase (Chen, Z. J. et al., Cell 84:853–862 (1996)) and in vitro-translated, $^{35}$S-labeled IκBα (FIG. 13C). In the absence of the ubiquitin-conjugating enzyme Ubc5 and ubiquitin, the IκBα kinase is inactive (lane 3), while in their presence the kinase is active, as evidenced by the shift in mobility of the $^{35}$S-labeled IκBα (lane 8), as shown previously (Chen, Z. J. et al., Cell 84:853–862 (1996)). Strikingly, addition of MEKK1Δ independently activates the IκBα kinase (lane 4), while MEKK1Δ alone does not site-specifically phosphorylate IκBα (lane 2). That this shift reflects phosphorylation of IκBα at Ser-32 and -36 is indicated by the fact that the S32A/S36A mutant fails to display this shift (lane 5). The activation of the IκBα kinase depends on the catalytic activity of MEKK1Δ, since mutant MEKK1Δ (K432M) fails to activate (lane 6). Neither recombinant MKK4 nor JNK1 augments MEKKΔ stimulation of the IκBα kinase, ruling out the possibility that MEKK1Δ activation of the IκBα kinase is mediated by an insect (Sf9) cell MKK4- or JNK-like activity copurifying in trace amounts with the MEKK1Δ protein. To eliminate the possibility that MEKK1Δ activation of the IκBα kinase is mediated through a factor present in the wheat germ extract employed for in vitro translation of IκBα, immunoprecipitation IκBα was employed as a substrate. As shown in lane 7, this IκBα is also a substrate for MEKK1Δ-activated IκBα kinase. Thus, MEKK1Δ activation of the IκBα kinase is direct. Additional experiments indicate that MEKK1Δ is a potent activator of the IκBα kinase (FIG. 13D), with activation demonstratible with MEKK1Δ doses as low as 5 ng (lane 2). Finally, IκBα complexed with RelA (p65) is a substrate for MEKK1Δ-activated IκBα kinase, just as it is for the ubiquitination-activated kinase.

The MEKK1-Inducible IκBα Kinase is a High Molecular Weight Complex

Figures 14A, 14B, 14C, 14D:
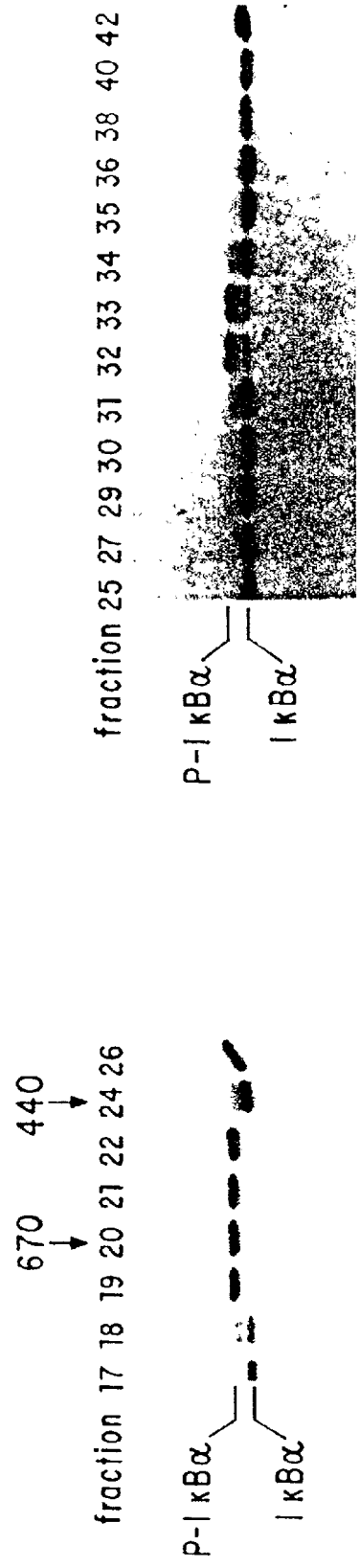
FIGS. 14A–14D are representations of autoradiographs of SDS-PAGE gels in which HeLa cell cytoplasmic extract functions were assayed for IκBα kinase activity in the presence of either (A and C) ubiquitination components or (D) MEKK1Δ.

To further examine the relationship between the MEKK1Δ- and the ubiquitination-inducible IκBα kinase previously reported (Chen, Z. J. et al., Cell 84:853–862 (1996)), HeLa cell cytoplasmic extracts were fractionated and assayed for both activities (FIG. 14). Notably, both MEKK1Δ- and ubiquitination-inducible IκBα kinase activities copurify during the first four steps of fractionation, which include ion exchange chromatography, ammonium sulfate fractionation, hydroxylapatite chromatography, and gel filtration (FIGS. 14A and 5B). With regard to the gel filtration step, the peak of MEKK1Δ-inducible IκBα kinase activity elutes at a position (fractions 19 to 20) corresponding to a native molecular weight of approximately 700 kDa, indistinguishable from that of the ubiquitination-inducible IκBα kinase (Chen, Z. J. et al., Cell 84:853–862 (1996)). Further fractionation by anion exchange chromatography reveals that the MEKK1Δ-inducible IκBα kinase activity elutes in a broader peak than the ubiquitination-inducible activity (FIGS. 14C and 14D). Thus, some fractions (e.g., 32 and 33) are inducible by both MEKK1Δ and ubiquitination, while others (e.g., 29 and 30) are inducible only by MEKK1Δ. Thus, the two kinase complexes are largely similar but may have subtle differences in structure or subunit composition.

MEKK1 is a Selective Activator of the IκBα Kinase

Figure 15A:
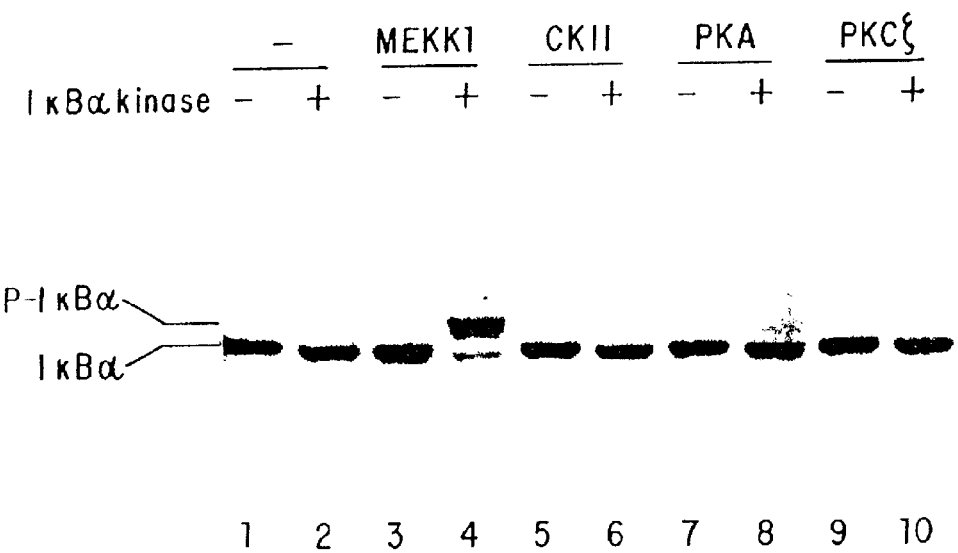
FIGS. 15A–15B are representations of autoradiographs of SDS-PAGE gels demonstrating that MEKK1 is a selective activator of IκBα kinase.
Figure 15B:
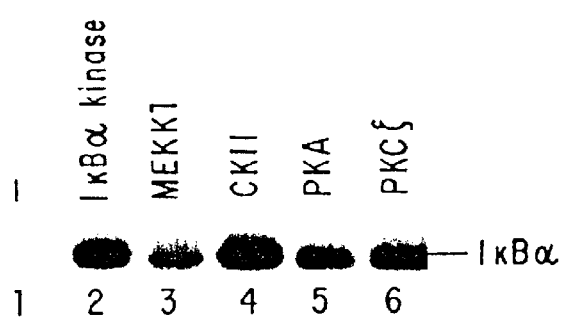

To examine the specificity of MEKK1 Δ activation of the IκBα kinase, three additional kinases, casein kinase II (CKII), protein kinase A (PKA), and protein kinase Cζ (PKCζ), were assayed for their capacity to activate the IκBα kinase (FIG. 15). In marked contrast to MEKKΔ, none of these enzymes activates the IκBα kinase (FIG. 15A). The enzymatic activity of the kinases is demonstrated by their roughly comparable degree of phosphorylation of recombinant IκBα with [γ-$^{32}$P]ATP (FIG. 15B). The experiment shown in FIG. 15A also demonstrates that none of the enzymes, aside from the IκBα kinase, phosphorylates IκBα at Ser-32 or -36 under the conditions employed. Phosphorylation by these other enzymes presumably occurs at residues other than Ser-32 or -36.

MEKK1 Activates the IκBα Kinase Complex by Phosphorylation

Figure 16A:
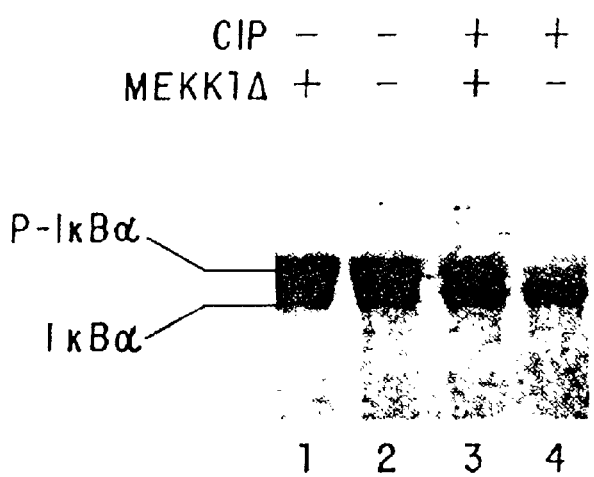
FIGS. 16A–16B are representations of autoradiographs of SDS-PAGE gels demonstrating that MEKK1 activates the IκBα kinase complex by phosphorylation.
Figure 16B:
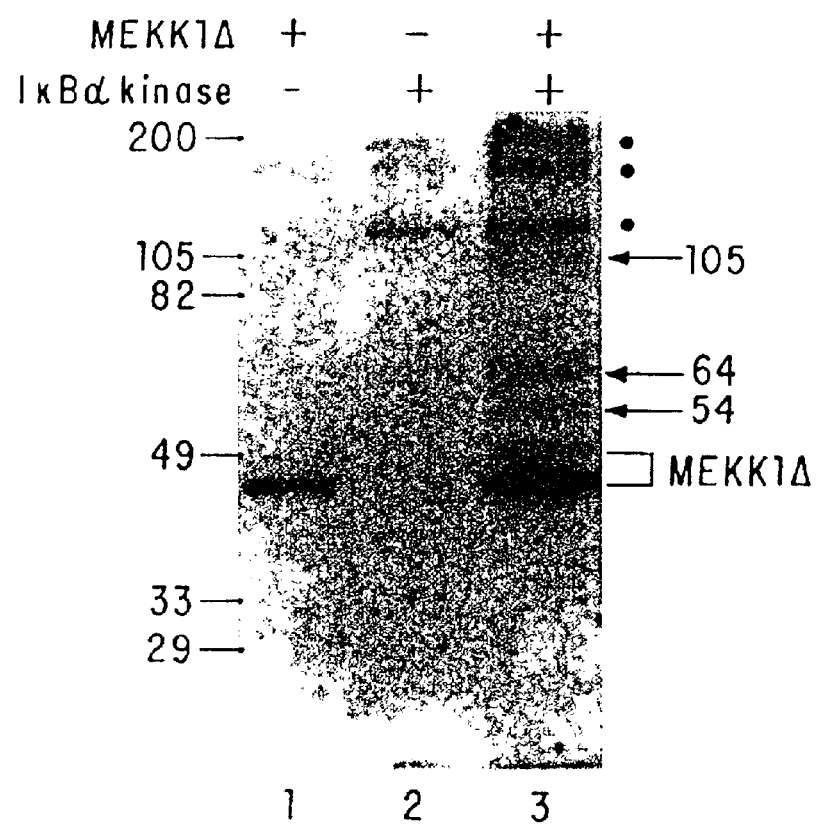

The fact that the catalytically inactive MEKK1Δ does not activate the IκBα kinase (FIG. 13C, lane 6) strongly suggests that MEKK1Δ phosphorylates the IκBα kinase complex. To further examine this possibility, MEKK1Δ activated IκBα kinase was incubated with or without calf intestinal alkaline phosphatase, and the IκBα kinase was then assayed for activity against $^{35}$S-labeled IκBα in the absence or presence of MEKK1Δ. As shown in FIG. 16A, treatment of the MEKK1Δ-activated IκBα kinase with phosphatase results in inactivation of IκBα kinase activity (compare lanes 2 and 4). Subsequent addition of MEKK1Δ results in substantial, though incomplete, restoration of IκBα kinase activity (compare lanes 2, 3, and 4). To extend these observations, the purified IκBα kinase was incubated with or without MEKK1Δ in the presence of [γ-$^{32}$P]ATP (FIG. 16B). In the absence of MEKK1Δ, $^{32}$P label was incorporated into three subunits (approximately 200, 180, and 120 kDa) of the IκBα kinase complex (lane 2). In the presence of MEKK1Δ, $^{32}$P label was incorporated into three additional subunits of molecular weights of approximately 105, 64, and 54 kDa (lane 3). In conjunction with the experiment employing the catalytically inactive MEKK1Δ (FIG. 13C), these experiments show that MEKK1Δ activates the IκBα kinase complex by phosphorylation.

Figure 17:
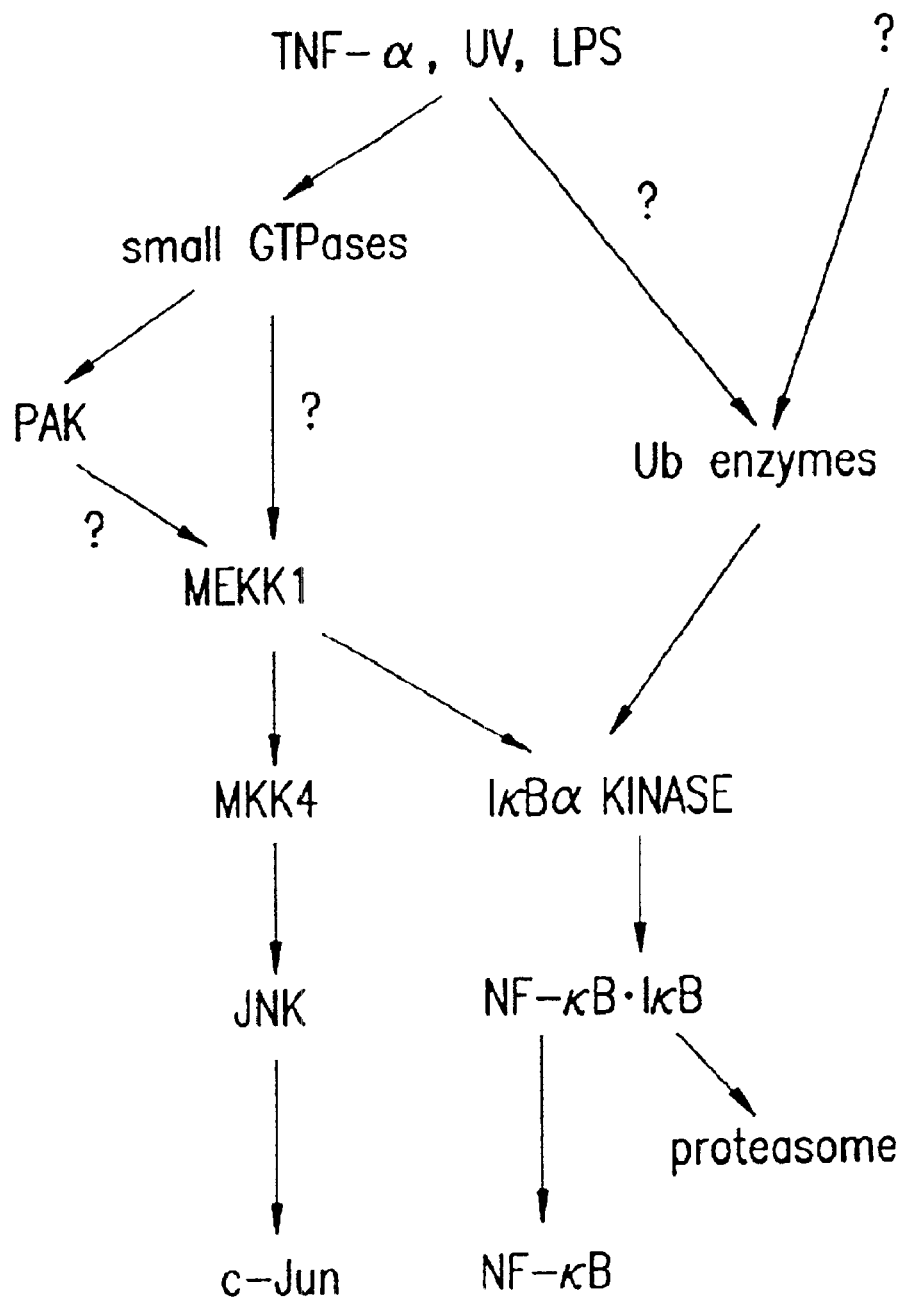
FIG. 17. Schematic representation of a model for coordinate activation of IκBα kinase and the JNK pathway by MEKK1.

The activation of the IκBα kinase and JNK pathway by a single protein, MEKK1, provides a compelling explanation for how multiple stimuli can simultaneously activate these two distinct kinases (FIG. 17). Thus, TNF-α, UV irradiation, and lipopolysaccharide have all been shown to activate the JNK pathway. Their implied activation of MEKK1 now provides a mechanism for the activation of the IκBα kinase. Stimuli such as phorbol myristate acetate/ionomycin could also potentially act through this pathway; in T cells, for example, phorbol myristate acetate and ionomycin synergistically activate the JNK pathway (Su, B. et al., *Cell* 77:727–736 (1994)) and thus may activate the IκBα kinase through MEKK1. The coordinate activation of the IκBα kinase and JNK raises the possibility that potential upstream activators of MEKK1, such as the small GTP-binding proteins Rac1, Cdc42, and Ras, as well as protein kinases that they activate, such as PAK, may also be common elements of a single upstream signal transduction mechanism.

Previous studies have implicated kinases other than MEKK1 in the activation of NF-κB. For example, PKA has been shown to dissociate the NF-κB-IκB complex (Ghosh, S. and Baltimore, D., *Nature* 344:678–682 (1990)), while PKCζ coimmunoprecipitates with a factor that can phosphorylate IκBα (Diaz-Meco, M. T. et al., *EMBO J.* 13:2842–2848 (1994)); with regard to the latter, it has been suggested that PKCζ activates a kinase that phosphorylates IκBα. Neither PKA nor PKCζ, however, phosphyroylates IκBα at Ser-32 and -36, nor does either activate the IκBα kinase (FIG. 15A). Additional kinases that have been implicated in NF-κB activation are raf-1 and the double-stranded RNA-activated protein kinase (PKR) (Finco, T. S. and Baldwin, A. S., *J. Biol. Chem.* 268:17676–17679 (1993); Yang, Y. L. et al., *EMBO J.* 14:6095–6106 (1995)). In preliminary experiments, activation of the IκBα kinase by enzymatically active c-raf (UBI) has not been observed.

MEKK1 is a member of a family of enzymes that share a conserved C-terminal catalytic domain and may thus share overlap in substrates (Lange-Carter, C. A. et al., *Science* 260:315–319 (1993); Blank, J. L. et al., *J. Biol. Chem.* 271:5361–5368 (1996); Xu, S. et al., *Proc. Natl. Acad. Sci. (USA)* 93:5291–5295 (1996)). Hence, it is conceivable that MEKK isoforms other than MEKK1 can activate the IκBα kinase. Different MEKK isoforms could potentially be involved in signaling responses to different stimuli. For example, MEKK1 has been shown to bind Ras in a GTP-dependent manner and thus its activity may be regulated in a similar fashion (Russell, M. et al., *J. Biol. Chem.* 270:11757–11760 (1995)). Indeed, Ha-Ras activation of NF-κB (Devary, Y. et al., *Science* 261:1442–1445 (1993)) could be mediated, in part, by activation of MEKK1. Aside from its interaction with Ras, little is known about the regulation and activation of MEKK1. The recent identification of MEKK1 as a large membrane-associated protein, with its C-terminal catalytic domain constituting less than 20% of the molecule, raises the possibility of complex modes of regulation (Xu, S. et al., *Proc. Natl. Acad. Sci. (USA)* 93:5291–5295 (1996)). While yet to be demonstrated, other MEKKs could conceivably be regulated by other upstream regulators such as Rac1, Cdc42, and PAK. These data also leave open the possibility that there may be other IκBα kinases that respond to stimuli distinct from those that signal through MEKK1.

It has been shown (Hirano, M. et al., *J. Biol. Chem.* 271:13234–13238 (1996)) that dominant negative MEKK1 inhibits TNF-α activation of an NF-κB reporter gene in vivo. This is in contrast to a recent report that reveals no effect of dominant negative MEKK1 in similar experiments, which conclude that MEKK1 lies on a pathway distinct from that of the IκBα kinase (Liu, Z.-G. et al., *Cell* 87:565–576 (1996)). At present, there is no explanation for this discrepancy. However, the transfection results are strongly supported by the observation that the IκBα kinase is phosphorylated and activated by MEKK1Δ in vitro. Thus, the IκBα kinase and MEKK1, or minimally an MEKK isoform, are indeed part of the same pathway.

The IκBα kinase can be activated by ubiquitination independently of phosphorylation (FIG. 17). This dual regulation by phosphorylation or ubiquitination is unprecedented. Thus, the IκBα kinase itself can be considered a signal integrator, responding to both phosphorylation and ubiquitination. Different stimuli may therefore activate one, the other, or both pathways. In principle, then, it may be possible to isolate an induced IκBα kinase species that is not ubiquitination-dependent, or one that is not phosphorylation-dependent. Indeed, the fractionation of highly purified IκBα kinase by ion exchange chromatography reveals kinase species that are phosphorylation but not ubiquitination inducible (FIGS. 14C and 14D).

A puzzling result from previous studies is that while IκBα kinase is easily assayed when present in HeLa cell S 100 cytoplasmic extracts, the purified kinase is inactive, requiring ubiquitination components for activity (Chen, Z. J. et al., *Cell* 84:853–862 (1996)). One possibility is that purification of the kinase separates the ubiquitination components from the kinase; hence, the purified kinase is inactive. The results described here raise a second and distinct possibility, namely that the IκBα kinase is activated by MEKK1 in the extract during the course of assay for IκBα kinase activity. Thus, purification of the IκBα kinase from S100 extracts removes it from both the ubiquitination components and MEKK1 present in the extract; in fact, Western blotting indicates that MEKK1 is not present in the IκBα kinase complex. Either ubiquitination or MEKK1-dependent phosphorylation can activate the purified IκBα kinase (FIG. 13C).

The detailed molecular mechanism by which MEKK1 activates the IκBα kinase remains to be determined. One possibility is that MEKK1 inactivates a negative regulatory subunit of the IκBα kinase, just as cAMP binds to and induces the dissociation of the regulatory subunit of PKA (Francis, S. H. and Corbin, J. D., *Annu. Rev. Physiol.* 56:237–272 (1994)). Alteratively, MEKK1 may activate the catalytic subunit of the IκBα kinase that subsequently phosphorylates Ser-32 and -36 of IκBα. Yet another possibility is that MEKK1 initiates a MAPK-like cascade within the IκBα kinase complex, with the terminal kinase the subunit that phosphorylates Ser-32 and -36; this would be somewhat analogous to the organization of MAPK modules as high molecular weight complexes in yeast (Choi, K. Y. et al., Cell 78:499–512 (1994)). The incorporation of $^{32}$P into multiple subunits of the IκBα kinase complex in the presence of MEKK1Δ (FIG. 16) could be consistent with any of these possibilities.

Amino acid sequence variants of the above-described kinase, subunits thereof or functional derivatives thereof can be prepared by mutations in the DNA or by chemical synthesis. Such variants include, for example, deletions from, or insertions or substitutions of, residues within the amino acid sequence of the kinase subunits or derivatives. Any combination of deletion, insertion, and substitution can also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure.

While the site for introducing an amino acid sequence variation is predetermined, the mutation per se need not be predetermined. For example, to optimize the performance of a mutation at a given site, random mutagenesis can be conducted at the target codon or region and the expressed above-described kinase subunit variants screened for the optimal combination of desired activity. Techniques for making substitution mutations at predetermined sites in DNA having a known sequence are well known, for example, site-specific mutagenesis.

Preparation of an above-described kinase variant in accordance herewith is preferably achieved by site-specific mutagenesis of DNA that encodes an earlier prepared variant or a nonvariant version of the protein. Site-specific mutagenesis allows the production of kinase variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., DNA 2:183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981). These phage are readily commercially available and their use is generally well known to those skilled in the art. Alternatively, plasmid vectors that contain a single-stranded phage origin of replication (Vieira et al., Meth. Enzymol. 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., Proc. Natl. Acad. Sci. (USA) 75:5765 (1978). This primer is then annealed with the single-stranded protein-sequence-containing vector, and subjected to DNA-polymerizing enzymes such as E. coli polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement.

After such a clone is selected, the mutated protein region can be removed and placed in an appropriate vector for protein production, generally an expression vector of the type that can be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within a complete kinase subunit sequence) can range generally from about 1 to 10 residues, more preferably 1 to 5.

The third group of variants are those in which at least one amino acid residue in the above-described kinase molecule, and preferably, only one, has been removed and a different residue inserted in its place. Such substitutions preferably are made in accordance with the following Table 1 when it is desired to modulate finely the characteristics of the above-described kinase.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of the above-described kinase. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of a native kinase subunit encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified kinase molecule variant is then screened in a suitable screening assay for the desired characteristic. For example, a change in the immunological character of the above-described kinase molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide or polypeptide of the present invention. In one embodiment, the peptide or polypeptide is purified from tissues or cells which naturally produce the peptide. Alternatively, the above-described isolated nucleic acid fragments could be used to express the above-described kinase or subunit thereof in any organism. The samples of the present invention include cells, protein extracts or membrane extracts of cells, or biological fluids. The sample will vary based on the assay format, the detection method and the nature of the tissues, cells or extracts used as the sample. Additionally, the peptide or polypeptide can be chemically synthesized, for example, using an automated solid-phase peptide synthesizer (See, Ausubel, F. M. et al., *Current protocols in Molecular Biology*, John Wiley & Sons, Inc., New York, N.Y. (1989), specifically, at page 18.6.11 of Supplement 35).

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the above-described kinase or subunit thereof free of natural contaminants. These include those listed in the Examples as well as, but are not limited to: immunochromotography, size-exclusion chromatography, HPLC, ion-exchange chromatography, and immunoaffinity chromatography.

In a preferred embodiment, the purification procedures comprise ion-exchange chromatography and size exclusion chromatography. Any one of a large number of ion-exchange resins known in the art can be employed, including for example, monoQ, sepharose Q, macro-prepQ, AG1-X2, or HQ. Examples of suitable size exclusion resins include, but are not limited to, Superdex 200, Superose 12, and Sephycryl 200. Elution can be achieved with aqueous solutions of potassium chloride or sodium chloride at concentrations ranging from 0.01M to 2.0M.

II. Isolated Nucleic Acid Molecules Coding for Kinase Subunits.

In another embodiment, the present invention relates to an isolated nucleic acid molecule coding for a polypeptide having an amino acid sequence corresponding to the above-described kinase or to a subunit of the above-described kinase.

Preferably, the isolated nucleic acid molecule which encodes a polypeptide having an amino acid sequence corresponding to the above-described kinase hybridizes to a second nucleic acid molecule having the nucleotide sequence set forth in any one of FIGS. 22A–B. More preferably, said isolated nucleic acid hybridizes preferentially or hybridizes under low stringency conditions, even more preferably moderate stringent, and even more preferably under high stringency conditions to a second nucleic acid having the nucleotide sequence of any one of FIGS. 22A–B. Most preferably, the nucleic acid molecule comprises the nucleotide sequence set forth in any one of FIGS. 22A–B.

Also included within the scope of this invention are the functional equivalents of the herein-described isolated nucleic acid molecules and derivatives thereof. For example, the nucleic acid sequences can be altered by substitutions, additions or deletions that provide for functionally equivalent molecules. Due to the degeneracy of nucleotide coding sequences, other DNA sequences which encode substantially the same amino acid sequence as a kinase subunit can be used in the practice of the present invention. These include but are not limited to nucleotide sequences comprising all or portions of the kinase subunit nucleic acids which are altered by the substitution of different codons that encode a functionally equivalent amino acid residue within the sequence, thus producing a silent change.

Such functional alterations of a given nucleic acid sequence afford an opportunity to promote secretion and/or processing of heterologous proteins encoded by foreign nucleic acid sequences fused thereto. All variations of the nucleotide sequence of the above-described kinase gene and fragments thereof permitted by the genetic code are, therefore, included in this invention.

In addition, the nucleic acid sequence can comprise a nucleotide sequence which results from the addition, deletion or substitution of at least one nucleotide to the 5'-end and/or the 3'-end of the nucleic acid formula of the above-described kinase gene or a derivative thereof. Any nucleotide or polynucleotide can be used in this regard, provided that its addition, deletion or substitution does not alter the amino acid sequence of the above-described kinase gene which is encoded by the nucleotide sequence. Moreover, the nucleic acid molecule of the present invention can, as necessary, have restriction endonuclease recognition sites added to its 5'-end and/or 3'-end.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid

In one aspect of the present invention, isolated nucleic acid molecules coding for polypeptides having amino acid sequences corresponding to the above-described kinase subunits are provided. In particular, the nucleic acid molecule can be isolated from a biological sample containing human RNA or DNA.

The nucleic acid molecule can be isolated from a biological sample containing human RNA using the techniques of cDNA cloning and subtractive hybridization. The nucleic acid molecule can also be isolated from a cDNA library using a homologous probe.

The nucleic acid molecule can be isolated from a biological sample containing human genomic DNA or from a genomic library. Suitable biological samples include, but are not limited to, blood, semen and tissue. The method of obtaining the biological sample will vary depending upon the nature of the sample.

One skilled in the art will realize that the human genome can be subject to slight allelic variations between individuals. Therefore, the isolated nucleic acid molecule is also intended to include allelic variations, so long as the sequence is a functional derivative of the above-described kinase gene. When the kinase allele does not encode the identical sequence to a known allele, it can be isolated and identified as the kinase allele using the same techniques used herein, and especially PCR techniques to amplify the appropriate gene with primers.

One skilled in the art will realize that organisms other than humans will also contain kinase subunit genes (for example, eukaryotes; more specifically, mammals, birds, fish, and plants; more specifically, gorillas, rhesus monkeys, and chimpanzees). The invention is intended to include, but not be limited to, above-described kinase subunit nucleic acid molecules isolated from the above-described organisms.

B. Synthesis of Nucleic Acid

Isolated nucleic acid molecules of the present invention are also meant to include those chemically synthesized. For example, a nucleic acid molecule with the nucleotide sequence which codes for the expression product of the above-described kinase gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185–3191 (1981) or by using an automated DNA synthesizer.

An oligonucleotide can be derived synthetically or by cloning. If necessary, the 5'-ends of the oligomers can be phosphorylated using T4 polynucleotide kinase. Phosphorylation of single strands prior to annealing or for labeling can be achieved using an excess of the enzyme. If phosphorylation is for the labeling of probe, the ATP can contain high specific activity radioisotopes. Then, the DNA oligomer can be subjected to annealing and ligation with T4 ligase or the like.

III. A Nucleic Acid Probe for the Specific Detection of Nucleic Acid Encoding the Kinase or a Subunit or Fragment Thereof.

In a further embodiment, the present invention relates to a nucleic acid probe for the specific detection of the presence of the above-described kinase or a subunit thereof in a sample comprising the above-described nucleic acid molecules or at least a fragment thereof which binds under stringent conditions to a nucleic acid molecule encoding the above-described kinase or a subunit thereof.

In one prefered embodiment, the present invention relates to an isolated nucleic acid probe consisting of 10 to 1000 nucleotides (prefererably, 10 to 500, 10 to 100, 10 to 50, 10 to 35, 20 to 1000, 20 to 500, 20 to 100, 20 to 50, or 20 to 35) which hybridizes preferentially to RNA or DNA of the above-described kinase or a subunit thereof (preferably, the probe will hybridize only to sequences which fully or partially encode the above-described kinase or subunit thereof), wherein said nucleic acid probe is or is complementary to a nucleotide sequence consisting of at least 10 consecutive nucleotides (preferably, 15, 20, 25, or 30) from the nucleic acid molecule comprising a polynucleotide sequence at least 90% identical to a sequence of the above-described kinase or a subunit thereof.

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (cf. *Molecular Cloning: A Laboratory Manual, second edition*, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the Above-described kinase or subunit thereof. Thus, the synthesized nucleic acid probes can be used as primers in a polymerase chain reaction (PCR) carried out in accordance with recognized PCR techniques, essentially according to *PCR Protocols, A Guide to Methods and Applications*, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. *Molecular Cloning: A Laboratory Manual, second edition*, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting the Presence of Nucleic Acid Encoding the Kinase or a Subunit or Fragment Thereof in a Sample.

In another embodiment, the present invention relates to a method of detecting the presence of the above-described kinase or subunit thereof in a sample comprising a) contacting the sample with (i) the above-described nucleic acid probe, under conditions such that hybridization occurs; (ii) a nucleic acid molecule which hybridizes to a second nucleic acid molecule having the nucleotide sequence set forth in anyone of FIGS. 22A–B; or (iii) a nucleic acid molecule which comprises the nucleotide sequence set forth in anyone of FIGS. 22A–B and b) detecting the presence of the probe bound to the nucleic acid molecule.

One skilled in the art would select the nucleic acid molecule according to techniques known in the art as described above. Samples to be tested include but should not be limited to RNA samples of human tissue.

Altered expression levels of kinase subunit RNA in an individual, as compared to normal levels, can indicate the presence of disease. The above-described kinase probes can further be used to assay cellular activity in general.

V. A Kit for Detecting the Presence of the Kinase or a Subunit Thereof in a Sample.

In another embodiment, the present invention relates to a kit for detecting the presence of the above-described kinase or a subunit thereof in a sample comprising at least one container means having disposed therein the above-described nucleic acid molecule. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid molecules and probes described in the present invention can readily be incorporated into one of the established kit formats which are well known in the art.

VI. DNA Constructs Comprising a Nucleic Acid Molecule Encoding a Kinase Subunit and Cells Containing These Constructs.

In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding the above-described kinase subunit gene can be obtained by the above-described methods. This region can be retained for its transcriptional termination regulatory sequences, such as termination and polyadenylation. Thus, by retaining the 3'-region naturally contiguous to the DNA sequence encoding the kinase gene, the transcriptional termination signals can be provided. Where the transcriptional termination signals are not satisfactorily functional in the expression host cell, then a 3' region functional in the host cell can be substituted.

Two DNA sequences (such as a promoter region sequence and an above-described kinase subunit sequence) are said to be operably linked if the nature of the linkage between the two DNA sequences does not (1) result in the introduction of a frame-shift mutation, (2) interfere with the ability of the promoter region sequence to direct the transcription of an above-described kinase subunit gene sequence, or (3) interfere with the ability of the above-described kinase subunit gene sequence to be transcribed by the promoter region sequence. Thus, a promoter region would be operably linked to a DNA sequence if the promoter were capable of effecting transcription of that DNA sequence.

The present invention encompasses the expression of any of the above-described kinase subunit genes (or a functional derivative thereof) in either prokaryotic or eukaryotic cells. Prokaryotic hosts are, generally, the most efficient and convenient for the production of recombinant proteins and, therefore, are preferred for the expression of the above-described kinase subunit gene.

Prokaryotes most frequently are represented by various strains of *E. coli*. However, other microbial strains can also be used, including other bacterial strains. In prokaryotic systems, plasmid vectors that contain replication sites and control sequences derived from a species compatible with the host can be used. Examples of suitable plasmid vectors include pBR322, pCDNA, pGEX, pGEM, pUC118, pUC119 and the like; suitable phage or bacteriophage vectors include λgt10, λgt11 and the like; and suitable virus vectors include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express an above-described kinase subunit in a prokaryotic cell, it is necessary to operably link the kinase sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of Bacillus (Gryczan, In: *The Molecular Biology of the Bacilli*, Academic Press, Inc., NY (1982)), and Streptomyces promoters (Ward et al., *Mol. Gen. Genet.* 203:468–478 (1986)). Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell.

Host cells which can be used in the expression systems of the present invention are not strictly limited, provided that they are suitable for use in the expression of an above-described kinase subunit of interest. Suitable hosts include eukaryotic cells. Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of the above-described kinase or subunit thereof in insects cells (Jasny, *Science* 238:1653 (1987); Miller et al., In: *Genetic Engineering* (1986), Setlow, J. K., et al., eds., Plenum, Vol. 8, pp. 277–297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the above-described kinase or subunit thereof. Furthermore, different vector/host expression systems can effect processing reactions such as proteolytic cleavages to different extents.

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of the above-described kinase or subunits thereof.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of the above-described kinase or subunits thereof in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (*London*) 290:304–310 (1981)); the yeast gal4 gene sequence promoter (Johnston et al., *Proc. Natl. Acad. Sci.* (*USA*) 79:6971–6975 (1982); Silver et al., *Proc. Natl. Acad. Sci.* (*USA*) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the above-described kinase or a subunit thereof does not contain any intervening codons which are capable of encoding a methionine (i.e., AUG). The presence of such codons results either in a formation of a fusion protein (if the AUG codon is in the same reading frame as the above-described kinase subunit coding sequence) or a frame-shift mutation (if the AUG codon is not in the same reading frame as the above-described kinase subunit coding sequence).

An above-described kinase subunit nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)).

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of an above-described kinase subunit(s). This can take place in the transformed cells as such, or following the induction of these cells to differentiate (for example, by administration of bromodeoxyuracil to neuroblastoma cells or the like).

VII. An Antibody Having Specific Binding Affinity to the Kinase or Subunit Thereof and a Hybridoma Containing the Antibody.

In another embodiment, the present invention relates to an antibody having binding affinity specifically to the above-described kinase or subunit thereof as described above or specifically to an above-described kinase binding fragment thereof. Those antibodies which bind selectively to the above-described kinase or a subunit thereof would be chosen for use in methods which could include, but should not be limited to, the analysis of altered kinase or subunit expression.

The above-described kinase or subunits thereof of the present invention can be used in a variety of procedures and methods, such as for the generation of antibodies, for use in identifying pharmaceutical compositions, and for studying DNA/protein interaction.

The above-described kinase or subunits thereof of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to the above-described kinase or subunits thereof which are produced in humans, or are "humanized" (i.e. nonimmunogenic in a human) by recombinant or other technology. Humanized antibodies can be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody. A hybridoma is an immortalized cell line which is capable of secreting a specific monoclonal antibody. In general, techniques for preparing monoclonal antibodies and hybridomas are well known in the art (Campbell, "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization. For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass is determined using procedures known in the art (Campbell, *Monoclonal Antibody Technology: Laboratory Techniques in Biochemistry and Molecular Biology, supra* (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, NY, pp. 289–307 (1992), and Kaspczak et al., *Biochemistry* 28:9230–8 (1989).

Anti-peptide peptides can be generated in one of two fashions. First, the anti-peptide peptides can be generated by replacing the basic amino acid residues found in the above-described kinase or subunit thereof sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting the Kinase or a Subunit Thereof in a Sample.

In another embodiment, the present invention relates to a method of detecting the above-described kinase or a subunit thereof in a sample, comprising: a) contacting the sample with an above-described antibody, under conditions such that immunocomplexes form, and b) detecting the presence of the antibody bound to the polypeptide. In detail, the methods comprise incubating a test sample with one or more of the antibodies of the present invention and assaying whether the antibody binds to the test sample. Altered levels of the above-described kinase or subunits thereof in a sample as compared to normal levels can indicate a specific disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising Antibodies to the Kinase or a Subunit Thereof.

In another embodiment of the present invention, a kit is provided which contains all the necessary reagents to carry out the previously described methods of detection. The kit can comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

X. Diagnostic Screening and Treatment.

It is to be understood that although the following discussion is specifically directed to human patients, the teachings are also applicable to any animal that expresses the above-described kinase or a subunit thereof.

The diagnostic and screening methods of the invention are especially useful for a patient suspected of being at risk for developing a disease associated with an altered expression level of the above-described kinase or a subunit thereof based on family history, or a patient in which it is desired to diagnose a disease related to the above-described kinase.

According to the invention, presymptomatic screening of an individual in need of such screening is now possible using DNA encoding the above-described kinase or a subunit thereof. The screening method of the invention allows a presymptomatic diagnosis, including prenatal diagnosis, of the presence of a missing or aberrant kinase subunit gene in individuals, and thus an opinion concerning the likelihood that such individual would develop or has developed a disease associated with the above-described kinase. This is especially valuable for the identification of carriers of altered or missing kinase genes, for example, from individuals with a family history of a disease associated with the above-described kinase. Early diagnosis is also desired to maximize appropriate timely intervention.

In one preferred embodiment of the method of screening, a tissue sample would be taken from such individual, and screened for (1) the presence of the "normal" kinase subunit gene(s); (2) the presence of the kinase subunit mRNA(s) and/or (3) the presence of the kinase or subunits thereof. The normal human gene can be characterized based upon, for example, detection of restriction digestion patterns in "normal" versus the patient's DNA, including RFLP analysis, using DNA probes prepared against the kinase sequence (or a functional fragment thereof) taught in the invention. Similarly, mRNA encoding a kinase subunit(s) can be characterized and compared to normal kinase mRNA (a) levels and/or (b) size as found in a human population not at risk of developing the kinase-associated disease using similar probes. Lastly, the above-described kinase subunits can be (a) detected and/or (b) quantitated using a biological assay for kinase activity or using an immunological assay and the above-described kinase antibodies. When assaying the above-described kinase protein, the immunological assay is preferred for its speed. An (1) aberrant kinase subunit DNA size pattern, and/or (2) aberrant kinase subunit(s) mRNA sizes or levels and/or (3) aberrant kinase protein levels would indicate that the patient is at risk for developing a disease associated with the above-described kinase.

The screening and diagnostic methods of the invention do not require that the entire kinase subunit DNA coding sequence be used for the probe. Rather, it is only necessary to use a fragment or length of nucleic acid that is sufficient to detect the presence of the kinase subunit gene(s) in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal kinase subunit gene is present in a heterozygous state.

In the method of treating a disease associated with the above-described kinase in a patient in need of such treatment, functional kinase or a subunit thereof DNA can be provided to the cells of such patient in a manner and amount that permits the expression of the protein provided by such gene, for a time and in a quantity sufficient to treat such patient.

Many vector systems are known in the art to provide delivery to human patients in need of a gene or protein missing from the cell. For example, retrovirus systems can be used, especially modified retrovirus systems and especially herpes simplex virus systems. Such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441. Delivery of a DNA sequence encoding a functional kinase or subunit thereof (as described above) will effectively replace the missing or mutated gene of the invention.

XI. Ligands of the Kinase.

In another embodiment, the invention relates to ligands of the above-described kinase. Preferably, the ligand interacts selectively with the kinase. Agonists and antagonists of the kinase are examples of ligands. Antibodies that recognize the kinase or a subunit or functional variant thereof are also ligands. Preferably, the ligand is a selective inhibitor of kinase activity.

In another preferred embodiment, the ligand is a substrate for the above-described kinase. Substrates are useful in assay methods for measuring kinase activity. Preferred substrates include IκBα and peptide or polypeptide fragments thereof.

The ability of antagonists and agonists of the above-described kinase to interfere with or enhance the activity of the above-described kinase can be evaluated in samples containing the above-described kinase. An assay for kinase activity in the sample can be used to determine the functionality of the protein in the presence of an agent which may act as antagonist or agonist, and thus, ligands that interfere or enhance the activity of the kinase are identified.

The agents screened in the assays can be, but are not limited to, peptides, carbohydrates, vitamin derivatives, or other pharmaceutical agents. These agents can be selected and screened 1) at random, 2) by a rational selection or 3) by design using for example, protein or ligand modeling techniques.

For random screening, agents such as peptides, carbohydrates, pharmaceutical agents and the like are selected at random and are assayed for their ability to bind to or stimulate/block the activity of the kinase.

Alternatively, agents may be rationally selected or designed. As used herein, an agent is said to be "rationally selected or designed" when the agent is chosen based on the configuration of the above-described kinase or subunit thereof or known ligand.

It is demonstrated herein that Staurosporine and its analogue K252a inhibit the phosphorylation and ubiquitination of IκBα in HeLa cell extracts. Additional agents may be designed based on these structures.

It is also demonstrated herein that a truncation mutant comprising amino acid residues 5–72 of IκBα selectively inhibits phosphorylation of IκBα by purified IκBα kinase. Additional agents may also be designed based on this structure.

Using an above-described kinase ligand (including antagonists and agonists as described above), the present invention further provides a method for modulating the activity of the above-described kinase in a cell. In general, agents (antagonists and agonists) which have been identified to block or stimulate the activity of the above-described kinase can be formulated so that the agent can be contacted with a cell expressing the above-described kinase protein in vivo. The contacting of such a cell with such an agent results in the in vivo modulation of the activity of the above-described kinase. So long as a formulation barrier or toxicity barrier does not exist, agents identified in the assays described in Section XII below, will be effective for in vivo use.

In another embodiment, the present invention relates to a method of administering the above-described kinase or subunit thereof or a ligand thereof (including kinase antagonists and agonists) to an animal (preferably, a mammal (more preferably, a human)) in an amount sufficient to effect an altered level of kinase activity, i.e. the ability to phosphorylate IκBα at serine residues 32 and 36.

NF-κB is an attractive target for drug design and therapeutic intervention because of its involvement in many pathological conditions such as inflammation, autoimmune disease, cancer and viral infection. A number of studies have shown that the inhibition of NF-κB activity can have profound physiological effects (Kitajima, I., *Science* 258:1792–1795 (1992); Higgins, K. A. et al., *Proc. Natl. Acad. Sci. USA* 90:9901–9905 (1993); Kopp & Ghosh, *Science* 265:956–969 (1994); Reed, M. A. et al., *Immunity* 2:1–20 (1995); Jung, M. et al., *Science* 268:1619–1621 (1995); Scheinman, R. I. et al., *Science* 270:283–286 (1995); Auphan, N. et al., *Science* 270:268–290 (1995)). Recent studies of the mechanism of NF-κB activation have provided new targets for drug intervention. The discovery of a novel IκBα kinase reported here provides methods for inhibiting aberrant NF-κB functions.

In a further embodiment, the present invention relates to a method of using antagonists of the above-described kinase to inhibit activation of NF-κB. These antagonists may be used to treat disease states characterized by undesired activation of NF-κB (for example, inflammation, HIV infection, cancer sepsis, psoriasis, restenosis and reperfusion injury).

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of the above-described kinase or ligand, in one or more administrations daily, for one or several days. The above-described kinase or ligand thereof can be administered parenterally by injection or by gradual perfusion over time. It can be administered orally, intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases and the like. See, generally, *Remington's Pharmaceutical Science*, 16th Ed., Mack Eds. (1980).

In another embodiment, the present invention relates to a pharmaceutical composition comprising the above-described kinase or subunit thereof or ligand thereof in an amount sufficient to alter the above-described kinase associated activity, and a pharmaceutically acceptable diluent, carrier, or excipient. Appropriate concentrations and dosage unit sizes can be readily determined by one skilled in the art as described above (See, for example, *Remington's Pharmaceutical Sciences* (16th ed., Osol, A., Ed., Mack, Easton Pa. (1980) and WO 91/19008).

XII. Bioassays for Obtaining Ligands of the Kinase.

The present invention further relates to a method of screening for an agonist or antagonist which stimulates or blocks the activity of the above-described kinase or subunit thereof comprising:

(a) incubating a sample containing the above-described kinase or subunit thereof with an agent to be tested; and (b) evaluating the biological activity mediated by said contact.

In one embodiment, the sample comprises a cell or cell extract. Any cell or cell extract may be used in the above assay so long as it expresses a functional form of the above-described kinase or subunit thereof and the activity can be measured. The preferred expression cells are eukaryotic cells or organisms. Such cells can be modified to contain DNA sequences encoding the above-described kinase subunit(s) using routine procedures known in the art. Alternatively, one skilled in the art can introduce mRNA encoding an above-described kinase subunit protein or proteins directly into the cell.

In a preferred embodiment, the sample comprises the above-described purified kinase in an activated state and a substrate. Ubiquitination enzymes or MEKK1 may be used to activate the kinase. The substrate may be IκBα or a functional variant thereof or a peptide or a polypeptide that is phosphorylated by the kinase.

In a preferred embodiment, the above assay is performed under conditions that support the stable phosphorylation of IκBα. Thus, reaction mixtures comprise labeled IκBα, an ATP regenerating system, E1, an E2, ubiquitin, and a phosphatase inhibitor (Chen et al., *Genes and Dev.* 9:1586–1597 (1995)). The substrate IκBα can contain any detectable label as known to those of ordinary skill in the art, including for example, a radioactive marker, a fluorescent marker, an enzymatic marker, or a chromogenic marker. In the Examples of the current invention, in vitro translated $^{35}$S-labeled IκBα was employed. The E2 is preferably one of the UBC4/UBC5 subfamily. The phosphatase inhibitor may be any one of many phosphatase inhibitors known to those of ordinary skill in the art, including but not limited to, okadaic acid, calyculin A, sodium pyrophosphate, sodium molybdate, sodium orthovanadate, or sodium fluoride. It is preferred that the phosphatase inhibitor be okadaic acid or calyculin A.

At the end of the reaction, phosphorylated substrate, e.g. IκBα, is separated from other components of the reaction mixture and quantified by a method appropriate to the label employed. In the Examples, after terminating the reaction with SDS sample buffer, samples are analyzed by SDS-PAGE and fluorography. It is to be understood that the use of substrates bearing different labels will necessitate the use of different detection methods such as are known to those skilled in the art. When a test substance is present in the reaction mixture, kinase inhibition is indicated by a reduction in the amount phosphorylated substrate produced in the test reaction as compared to that produced in a control reaction mixture that does not contain the test substance.

XIII. Transgenic and "Knock-out" Mice.

Methods of Generating Transgenic Non-Human Animals

The non-human animals of the invention comprise any animal having a transgenic interruption or alteration of the endogenous ubiquitin dependent kinase subunit gene(s) (knock-out animals) and/or into the genome of which has been introduced one or more transgenes that direct the expression of the above-described kinase.

Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J. D., et al., in *Recombinant DNA*, 2d Ed., W. H. Freeman & Co., New York (1992), pages 255–272; Gordon, J. W., *Intl. Rev. Cytol.* 115:171–229 (1989); Jaenisch, R., *Science* 240:1468–1474 (1989); Rossant, J., *Neuron* 2:323–334 (1990)).

The transgenic non-human animals of the invention are produced by introducing transgenes into the germline of the non-human animal. Embryonic target cells at various developmental stages are used to introduce the transgenes of the invention. Different methods are used depending on the stage of development of the embryonic target cell(s).

1. Microinjection of zygotes is the preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 picoliters of a solution containing transgenic DNA sequences. The use of a zygote for introduction of transgenes has the advantage that, in most cases, the injected transgenic DNA sequences will be incorporated into the host animal's genome before the first cell division (Brinster, et al., *Proc. Natl. Acad. Sci.* (*USA*) 82:4438–4442 (1985)). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyst. At this time, the blastomeres may be infected with appropriate retroviruses (Jaenich, R., *Proc. Natl. Sci.* (*USA*) 73:1260–1264 (1976)). Infection of the blastomeres is enhanced by enzymatic removal of the zona pellucida (Hogan, et al., in *Manipulating the Mouse Embryo*, Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., *Proc. Natl. Acad. Sci.* (*USA*) 82:6927–6931 (1985); Van der Putten, et al., *Proc. Natl. Acad. Sci.* (*USA*) 82:6148–6152 (1985)). Transfection is easily and efficiently obtained by culture of blastomeres on a mono-layer of cells producing the transgene-containing viral vector (Van der Putten, et al., *Proc. Natl. Acad. Sci.* (*USA*) 82:6148–6152 (1985); Stewart, et al., *EMBO Journal* 6:383–388 (1987)). Alternatively, infection may be performed at a later stage, such as a blastocoele (Jahner, D., et al., *Nature* 298:623–628 (1982)). In any event, most transgenic founder animals produced by viral integration will be mosaics for the transgenic allele;

that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D., et al., *Nature* 298:623–628 (1982)). However, once a transgene has been introduced into germline cells by this method, offspring may be produced in which the transgenic allele is present in all of the animal's cells, i.e., in both somatic and germline cells.

3. Embryonic stem (ES) cells can also serve as target cells for introduction of the transgenes of the invention into animals. ES cells are obtained from pre-implantation embryos that are cultured in vitro (Evans, M. J., et al., *Nature* 292:154–156 (1981); Bradley, M. O., et al., *Nature* 309:255–258 (1984); Gossler, et al., *Proc. Natl. Acad. Sci. (USA)* 83:9065–9069 (1986); Robertson et al., *Nature* 322:445–448 (1986); Robertson, E. J., in *Teratocarcinomas and Embryonic Stem Cells: A Practical Approach*, Robertson, E. J., ed., IRL Press, Oxford (1987), pages 71–112). ES cells, which are commercially available (from, e.g., Genome Systems, Inc., St. Louis, Mo.), can be transformed with one or more transgenes by established methods (Lovell-Badge, R. H., in *Teratocarcinomas and Embryonic Stem Cells: A Practical Approach*, Robertson, E. J., ed., IRL Press, Oxford (1987), pages 153–182). Transformed ES cells can be combined with an animal blastocyst, whereafter the ES cells colonize the embryo and contribute to the germline of the resulting animal, which is a chimera (composed of cells derived from two or more animals) (Jaenisch, R., *Science* 240:1468–1474 (1988); Bradley, A., in *Teratocarcinomas and Embryonic Stem Cells: A Practical Approach*, Robertson, E. J., ed., IRL Press, Oxford (1987), pages 113–151). Again, once a transgene has been introduced into germline cells by this method, offspring may be produced in which the transgenic allele is present in all of the animal's cells, i.e., in both somatic and germline cells.

However it occurs, the initial introduction of a transgene is a Lamarckian (non-Mendelian) event. However, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into non-human animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism) (Leder et al., U.S. Pat. No. 5,175,383 (Dec. 29, 1992); Kindt et al., U.S. Pat. No. 5,183,949 (Feb. 2, 1993); Small et al., *Cell* 46:13–18 (1986); Hooper et al., *Nature* 326:292–295 (1987); Stacey et al., *Nature* 332:131–136 (1988); Windle et al., *Nature* 343:665–669 (1990); Katz et al., *Cell* 74:1089–1100 (1993)). Transgenically introduced mutations further comprise null ("knock-out") alleles in which a DNA sequence encoding a selectable and/or detectable marker is substituted for a genetic sequence normally endogenous to a non-human animal. Resultant transgenic non-human animals that are predisposed to a disease, or in which the transgene causes a disease, may be used to identify compositions that induce the disease and to evaluate the pathogenic potential of compositions known or suspected to induce the disease (Berns, A. J. M., U.S. Pat. No. 5,174,986 (Dec. 29, 1992)), or to evaluate compositions which may be used to treat the disease or ameliorate the symptoms thereof (Scott et al., WO 94/12627 (1994)).

Offspring that have inherited the transgenes of the invention are distinguished from littermates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the selectable marker of the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention, such as the selectable marker thereof. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc.

The present invention is described in further detail in the following non-limiting examples.

EXAMPLES

The following protocols and experimental details are referenced in the examples that follow.

Plasmids, Proteins and Antibodies cDNAs encoding, IκBα and its mutants have been described (Brockman, J. A. et al., *Mol. Cell. Biol.* 15:2809–2818 (1995); Chen, Z. J. et al., *Genes & Dev.* 9:1586–1597 (1995)), $^{35}$S-labeled IκBα proteins were prepared by in vitro translation in wheat germ extracts (Promega). pGEX-2TK-UBCh5 was constructed by PCR using UBCh5 cDNA (provided by Dr. P. Howley) as a template. The active site mutants of UBCh5, pGEX-2TK-UBCh5 (C85A) and pGEX-2TK-UBCh5(C85S), were created by site-directed mutagenesis using the Unique Site Elimination (U.S.E) mutagenesis kit (Pharmacia). The mutagenic primers (anneal to noncoding strand) were:

5' TTG TGA CCT CAG GAT ATC GAG AGC AAT ACT TCC ATT 3' for C85A, and

5' TTG TGA CCT CAG GAT ATC GAG AGA AAT ACT TCC AT 3' for C85S.

All constructs were confirmed by DNA sequencing. For expression of GST-UBCh5 and its mutants, the appropriate expression constructs were transformed into the *E. coli* strain BL21/DE3, and protein expression was induced with 200 μM IPTG. GST fusion proteins were purified using Glutathione-Sepharose (Pharmacia). Yeast UBC4 (yUBC4) was expressed in the *E. coli* AR58 harboring the UBC4 expression vector (pLλUBC4, provided by Dr. V. Chau). After heat induction (30° C. to 42° C.), UBC4 was purified by ubiquitin-Sepharose covalent chromatography, followed by gel filtration on FPLC/Superdex-200. Recombinant RelA homodimer was prepared according to Thanos and Maniatis, *Cell* 80:529–532 (1992) (provided by Dr. J. Hagler). Purified recombinant human UBC2 was provided by Dr. O. Coux. Purification of E1, $E2_{14K}$, $E2_{7K}$, $E2_{20K}$, $E2_{25K}$, $E2_{35K}$ from rabbit reticulocytes were according to Haas and Bright, *J. Biol. Chem.* 263:13258–13267 (1988). Preparation of methylated ubiquitin and ubiquitin aldehyde have been described (Chen, Z. J. et al., *Genes & Dev.* 9:1586–1597 (1995)). $^{125}$I-ubiquitin was prepared by the Chloramine T method. Antibodies against IκBα and RelA were from Santa Cruz Biotechnology.

Preparation of Recombinant Proteins (His)$_6$MEKK1Δ and (His)$_6$MEKK1Δ (K432M) were purified using Ni-NTA agarose from Sf9 cells infected with baculovirus prepared using the Bac-to-Bac Expression System (GIBCO-BRL Life Technologies). pFastBacHT-MEKK1Δ and pFastBacHT-MEKK1Δ (K432M) were constructed by subcloning the 1.2 kb NcoI/XbaI coding sequence fragment of pcDNA3-FlagMEKK1Δ and pcDNA3-FlagMEKK1Δ (K432M), respectively, into the Nco I/Xba I site of pFastBacHTa. Recombinant bacmids and baculovirus were subsequently prepared according to the manufacturer's instructions. GST-MKK4 and GST-JNK1 were purified from *E. coli* HB101 transformed with pGEX-MKK4 and pGEX-JNK1, respectively, employing glutathione agarose affinity chromatography as described (Smith, D. B. and Johnson, K. S., *Gene* 67:31–40 (1988)). pGEX-MKK4 was constructed by subcloning the 1.1 kb BamHI (blunt)/Bsp1201 (blunt) fragment of pcDNA3-FlagMKK4 containing the MKK4 coding sequence into the SmaI site of pGEX-3X (Pharmacia). pGEX-JNK1 was constructed by subcloning the 1.4 kb NcoI (blunt)/SalI fragment of pSRαHA-JNK1 containing the JNK1 coding sequence into the EcoRI (blunt)/SalI site of pGEX-5X-1 (Pharmacia). (His)$_6$IκBα was purified using Ni-NTA agarose from *E. coli* BL21(DE3)LysS transformed with pRSET-IκBα. pRSET-IκBα was constructed by subcloning the EagI (blunt)/HindIII fragment of pBS-IκBα containing the IκBα coding sequence into the PvuII/HindIII site of pRSET A (Invitrogen). The E2 enzymes Ubc4 and GST-Ubc5 were prepared as described (Chen, Z. J. et al., *Cell* 84:853–862 (1996)). Concentrations of recombinant proteins were determined by SDS-PAGE followed by staining with Coomassie blue and comparison with bovine serum albumin standards.

pCMV5-MEKK1 (which encodes the C-terminal 672 residues of MEKK1), pcDNA3-FlagMKK4, and pSRαHA-JNK1 were gifts of Dr. Roger Davis (University of Massachusetts, Worcester) and have been described (Derijard, B. et al., *Cell* 76:1025–1037 (1994); Derijard, B. et al., *Science* 267:682–685 (1995); Whitmarsh, A. J. et al., *Science* 269:403–407 (1995)). pcDNA3-MEKK1 was constructed by subcloning the 2.4 kb EcoRI/EcoRI/EcoNI (blunt) fragment of pCMV5-MEKK1 encoding MEKK1 into the EcoRI/EcoRV site of pcDNA3. pcDNA3-Flag MEKK1Δ (K432M) consists of an N-terminal Flag epitope fused to the C-terminal 321 amino acid fragment of MEKK1 with the indicated mutation (amino acid numbering according to Lange-Carter, C. A. et al., *Science* 260:315–319 (1993)) and was constructed by polymerase chain reaction (Ausubel, F. M. et al., *Current protocols in Molecular Biology*, John Wiley & Sons, Inc., New York, N.Y. (1989)). pcDNA3-FlagMEKK1Δ was constructed by replacing the 2.1 kb StuI fragment of pcDNA3-FlagMEKK1Δ (K432M), which encodes the C-terminal 262 amino acids with the corresponding fragment of pcDNA3-MEKK1. pCMV4-FlagIκBα and pCMV4-FlagIκBα (S32A/S36A) were gifts of Dr. Dean Ballard (Vanderbilt University) and have been described (Brockman, J. A. et al., *Mol. Cell. Biol.* 15:2809–2818 (1995)). pcDNA1-cJun has been described (Du, W. and Maniatis, T., *Cell* 74:887–898 (1993)). pcDNA1-cJun(S63A/S73A) was constructed using overlapping polymerase chain reaction (Ausubel, F. M. et al., *Current protocols in Molecular Biology*, John Wily & Sons, Inc., New York, N.Y. (1989)). PBS-IκBα, pBS-IκBα (S32A/S36A), pBS-FlagIκBα, pBS-FlagIκBα (S32A/S36A), (PRDII)$_2$CAT, (PRDIV)$_6$CAT, (CRE)$_6$CAT, -110IFN-βCAT, and pCMV-lacZ have been described (MacGregor, G. R. and Caskey, C. T., *Nucl. Acids Res.* 17:2365 (1989); Du, W. and Maniatis, T., *Proc. Natl. Acad. Sci (USA)* 89:2150–2154 (1992); Thanos, D. and Maniatis, *Cell* 71:777–789 (1992); Chen, Z. J. et al., *Genes & Dev.* 9:1586–1597 (1995)).

Extract Preparation

HeLa $S_3$ cell cytoplasmic extracts were prepared by two methods. In the first ("rapid lysis procedure"), mid-logarithmic growth phase HeLa $S_3$ cells cultured in RPMI 1640 media supplemented with 5% horse serum, 2 mM L-glutamine, 100 U/ml penicillin, and 100 μg/ml streptomycin were centrifuged at 2,600× g for 10 min. Cells were resuspended in RPMI media containing 5% horse serum, and then either mock treated or incubated with 1000 U/ml TNF-α at 37° C. At various times, cells were centrifuged at 1,000× g for 1 min at ambient temperature. Cells were then rapidly washed with ice-cold PBS, centrifuged again at 1,000× g for 1 min, resuspended in ice-cold 50 mM Tris (pH 7.5), 1 mM EGTA, and then immediately lysed by dounce homogenization (15–20 strokes with an A-type pestle). The crude lysate was clarified by centrifugation at 4,600× g for 10 min at 4° C., and the resulting supernatant immediately frozen at −80° C. In the second method ("S100"), HeLa $S_3$ cells were swollen in a hypotonic buffer and lysed, followed by removal of nuclei and centrifugation at 100,000× g as described (Dignam et al., 1983). The supernatant was then dialyzed extensively against 20 mM Tris (pH 7.5), 0.5 mM DTT. If not employed immediately, the extract was stored at −80° C.

Fractionation of HeLa Cytoplamic Extracts and Purification of IκBα Kinase

Method A

HeLa S100 cytoplasmic extracts were concentrated by ammonium sulfate (80%) precipitation, followed by dialysis in 20 mM Tris-HCl, pH 7.2, 0.5 mM DTT. The dialyzed extracts were applied to FPLC/monoQ (Pharmacia) equilibrated in Buffer A (50 mM Tris-HCl, pH 7.5, 0.5 mM DTT), and the flow through was collected and concentrated using Centriprep-10 (Amicon). The concentrated flow-through was designated as fraction I. To prepare fraction II, bound proteins were eluted with Buffer B (Buffer A+0.5 M KCl) and concentrated. To purify IκBα kinase, proteins bound to monoQ were eluted stepwise with 0.1, 0.2, 0.3, 0.4 and 0.5M KCl in Buffer A. The IκBα kinase containing fractions (0.2–0.3M KCl eluate) were pooled and further fractionated by ammonium sulfate (40%) precipitation. The precipitates were resuspended with a minimum volume of Buffer A, and then separated by size exclusion chromatography on FPLC/Superdex 200 in Buffer C (50 mM Tris-HCl, pH 7.5, 0.5 mM DTT, 150 mM NaCl). The active fractions were pooled and applied to FPLC/monoQ which had been equilibrated with Buffer C. The column was eluted with a linear gradient of 0.15M–0.4M NaCl in Buffer C. The fractions containing IκBα kinase were concentrated by Centricon-10 and then re-sized on FPLC/Superdex-200 as described above. Active fractions were pooled, concentrated and stored at −80° C. The storage buffer is Buffer A plus 10% glycerol.

Method B

HeLa cell S100 cytoplasmic extract, prepared as above, was applied to a Mono-Q anion exchange column. The IκBα kinase activity was eluted with 0.2–0.3 M KCl in Buffer D (50 mM Tris, pH 7.5, 0.5 mM DTT), and then precipitated with 40% ammonium sulfate. The resuspended precipitates were dialyzed against 10 mM $K_2HPO_4$—$KH_2PO_4$ (pH 7.0), 0.5 mM DTT, and then applied to a hydroxylapatite column. After elution with 0.2 M $K_2HPO_4$—$KH_2PO_4$ (pH 7.0), the kinase-containing fractions were applied to a Superdex-200 gel filtration column equilibrated with 50 mM Tris (pH 7.5), 0.5 mM DTT, and 150 mM NaCl. The high molecular weight fractions that contained the kinase activity were applied to a Mono-Q column and eluted with a linear gradient of 150–325 mM NaCl in Buffer D. Fractions from the Superdex-200 and second Mono-Q chromatographies were assayed for IκBα kinase activity in the presence of ubiquitination components (Ubc4 and ubiquitin, in addition to E1 supplied by the wheat germ extract employed for in vitro translation of IκBα) (Chen, Z. J. et al., *Cell* 84:853–862 (1996)), or recombinant MEKK1Δ.

Figure 18:
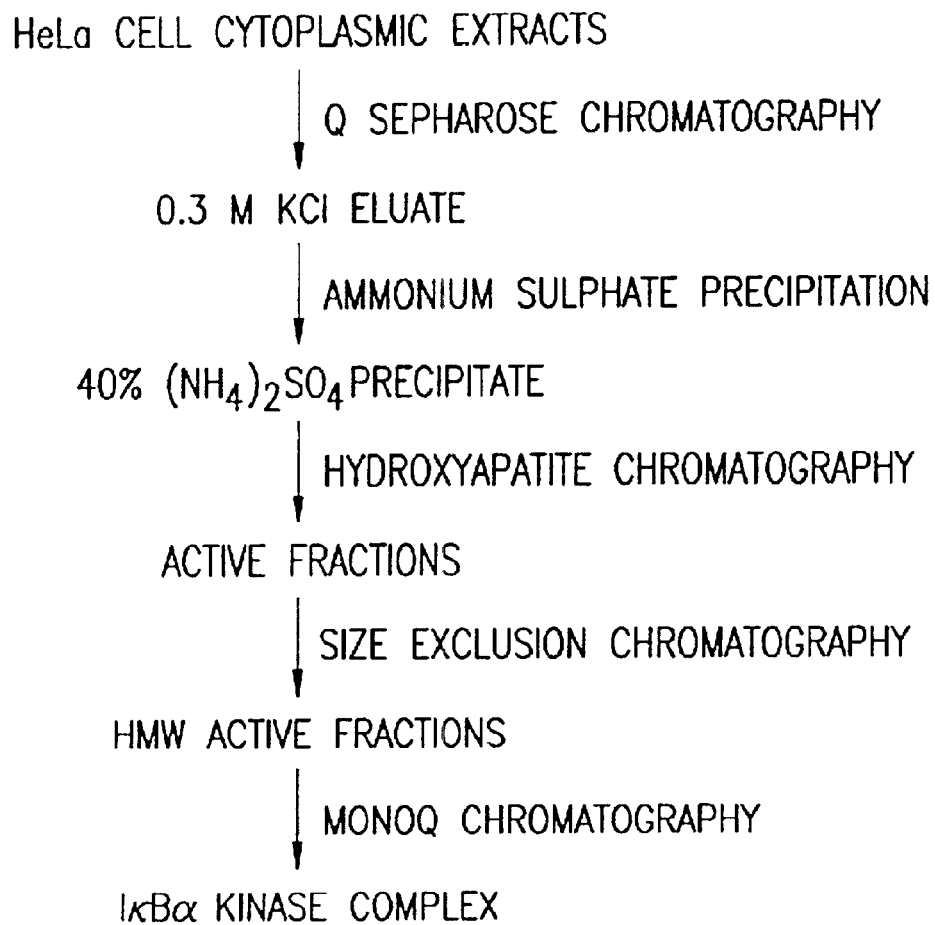
FIG. 18. Schematic representation of a purification scheme for IκBα kinase.

Method C (FIG. 18)

HeLa cell cytoplasmic extracts were loaded onto a MonoQ anion exchange column and the IκBα kinase activity was eluted with 0.3 M KCl in Buffer A (50 mM Tris-HCl, pH 7.6, 0.5 mM DTT). Solid ammonium sulfate was then added to the kinase containing fractions so that the final concentration equals to 40% saturation. The precipitates were resuspended in Buffer B (10 mM $K_2HPO_4$—$KH_2PO_4$, pH 7.0, 0.5 mM DTT) and dialyzed again Buffer B at 4° C. overnight. The dialyzed material was then applied to a hydroxyapatite column and IκBα kinase was eluted with a linear gradient of 0–0.2 M $K_2HPO_4$—$KH_2$—$PO_4$, pH 7.0. The active kinase fractions were pooled and applied to a Superdex-200 column in Buffer A containing 150 mM NaCl. The high molecular fractions containing the IκBα kinase activity was pooled and further fractionated on Mono Q column with a linear gradien of 150–325 mM NaCl in Buffer A. Each fraction was assayed for IκBα kinase activity and analyzed for protein content by electrophoresis on 2–15% native gel followed by silver staining.

Phosphorylation and Ubiquitination Assays

Unless otherwise indicated, phosphorylation of IκBα was usually carried out at 37° C. for 1 hour in a reaction volume of 10 μl containing: an ATP regenerating system (50 mM Tris-HCl, pH 7.6, 5 mM $MgCl_2$, 2 mM ATP, 10 mM creatine phosphate, 3.5 units/ml creatine kinase, 0.6 units/ml inorganic pyrophosphatase), 0.5 μl of in vitro translated $^{35}$S-labeled IκBα, 2 μg/ml of recombinant RelA homodimer (to form complex with IκBα), 3 μM okadaic acid, 60 μM ubiquitin, 50 nM E1 (rabbit), 1 μM UBC4 (yeast) or GST-UBCh5 (human), and 0.5–3 μl of IκBα kinase containing fractions. In some experiments, HeLa fraction I (1 mg/ml) was used as a source of E2s. At the end of each reaction, SDS sample buffer was added to quench the reaction, and the samples were analyzed by SDS-PAGE (9%) followed by flourography. Phosphorylation of IκBα was quantitated by PhosphorImager analysis. Ubiquitination of IκBα has been described previously (Chen, Z. J. et al., *Genes & Dev.* 9:1586–1597 (1995)).

Thioester Assays

The thioester reaction mixtures contain: 50 mM Tris, pH 7.6, 0.1 μM of E1 (rabbit), approximately 1 μM of E2, 0.6 μM of $^{125}$I-labeled ubiquitin ($10^7$ cpm/nmol). After 3 minutes at 37° C., the reactions were quenched by adding equal volume of SDS sample buffer lacking reducing agents. The samples were subject to SDS-PAGE (10–20% gradient gel) and fluorography.

Phosphatase and Thrombin Treatment

Following phosphorylation of IκBα, RIPA buffer (50 mM Tris-HCl pH 8.0, 150 mM NaCl, 1% NP40, 0.5% deoxycholate, also include 0.1% SDS) and anti-IκBα antisera (against the C-terminus of IκBα) were added to the reaction mixture which was then incubated at 4° C. for 45 min. Protein A-Trisacryl was added to the mixture and the incubation was continued at 4° C. for another 45 min. The beads were washed three times with RIPA buffer lacking SDS, and three times with Buffer A. In dephosphorylation reactions, 1 μl of calf intestine alkaline phosphatase (CIP, 18U/μl) and 1 μl of 10× dephosphorylation buffer (0.5 M Tris-HCl, pH 8.5, 1 mM EDTA) was added to the beads containing the IκBα immune complex and incubated at 37° C. for 30 min. The reaction was quenched with SDS sample buffer and analyzed by SDS-PAGE (9%) and fluorography. Control reactions contain either dephosphorylation buffer alone or CIP plus a phosphatase inhibitor cocktail (50 mM NaF, 50 mM glycerol-2-phosphate 1 mM sodium orthovanadate, 5 μM okadaic acid).

To cleave off the N-terminus of IκBα with thrombin, immunoprecipitates containing IκBα (+/−CIP treatment) were washed three times with thrombin buffer (20 mM Tris, pH 8.3, 150 mM NaCl, 2.5 mM $CaCl_2$, and 10% glycerol.), and then treated with 3U of thrombin (Sigma) at 30° C. for 2 hours. The supernatant containing the cleaved N-terminal fragment of IκBα was mixed with SDS sample buffer, and then analyzed on 16.5% Tris-tricine gels followed by flourography (Whiteside, S. T. et al., *Mol. Cell. Biol.* 15:5339–5345 (1995)).

Tissue Culture and Transfection

HeLa and L929 cells were maintained in DME media supplemented with 10% fetal bovine serum, 2 mM L-glutamine, 100 U/ml penicillin, and 100 μg/ml streptomycin. Transfections and virus infections, performed in 3.5 cm diameter wells, were conducted as described (Thanos, D. and Maniatis, *Cell* 71:777–789 (1992)). Cells were typically harvested at 41 to 49 hr posttransfection. CAT and β-galactosidase assays were performed as described (Sambrook, J. et al., *Molecular Cloning: A Laboratory Manual*, Second Edition, Cold Srping Harbor Laboratory Press, Cold Spring Harbor, N.Y. (1989)). Protein concentrations were measured by the Bradford method.

Immunoprecipitations

Transfected IκBα

Cell pellets obtained by harvesting 3.5 cm diameter wells were by the addition of 200 μl of Buffer A (20 mM Tris, pH 7.5, 0.4 M KCl, 4 mM β-glycerolphosphate, 0.1 mM sodium orthovanadate, 0.1% NP-40, 10% glycerol, 10 μg/ml leupeptin, 1 mM PMSF, and 1 mM DTT), followed by three freeze/thaw cycles. After centrifugation at 14,000× g for 5 min at 4° C., the supernatant (320 μg protein) was incubated with 20 μl of M2-agarose (IBI-Kodak) in 1 ml of Buffer A with end-over-end rotation for 1 hr at 4° C. Resins were then washed three times with Buffer A and once with 0.1× Buffer A.

$^{35}$S-Labeled FlagIκBα

In vitro-translated FlagIκBα was immunoprecipitated by incubation with 10 μl of M2-agarose in 1 ml of Buffer B (10 mM Tris, pH 7.6, 100 mM NaCl, 0.1% NP-40, 10 µg/ml leupeptin, 1 mM DTT) with end-over-end rotation for 1 hr at 4° C. Resins were then washed three times with Buffer B, once with Buffer C (10 mM Tris, pH 7.6, 1 mg/ml BSA, 10 µg/ml leupeptin, 1 mM DTT), and then eluted by the addition of 24 µl of Buffer C containing 0.7 mg/ml Flag peptide for 30 min on ice.

Western Blotting

Proteins were electrophoresed by SDS-PAGE and transferred to lmmobilon-NC membranes (Millipore). The membranes were blocked with 5% nonfat milk and probed with rabbit anti-IκBα polyclonal antibodies (C21, Santa Cruz Biotechnology). Membranes were then incubated with goat anti-rabbit IgG-alkaline phosphatase or donkey anti-rabbit IgG-horseradish peroxidase conjugates, and developed using standard chromogenic or Enhanced Chemiluminescence (Amersham) substrates, respectively. Western blots of purified IκBα kinase employed antibodies (anti-MEKK1 [C22], anti-MKK4 [C20], anti-JNK1 [FL], anti-JNK2 [FL]) obtained from Santa Cruz Biotechnology.

Protein Kinase Assays

Gel Based Assays

Typically, HeLa cell cytoplasmic extracts or purified IκBα kinase (from gel filtration chromatography as described above) was incubated with 0.5 µl of in vitro-translated, $^{35}$S-labeled protein in a total volume of 10 µl containing 50 mM Tris (pH 7.6), 6 mM $MgCl_2$, 2 mM ATP, 10 mM phosphocreatine, 3.5 U/ml creatine phosphokinase, and 2.5 µM okadaic acid. In vitro-translated, $^{35}$S-labeled IκBα, FlagIκBα, and c-Jun, or their phosphorylation defective mutants, were prepared using TnT wheat germ extract kits (Promega) and pBS-IκBα, pBS-4κBα (S32A/S36A), pBS-FlagIκBα, pBS-FlagIκBα (S32A/S36A), pcDNA1-cJun, or pcDNA1-cJun(S63A/S73A) as templates.

[γ-$^{32}$P]ATP Labeling of IκBα

Enzyme was incubated with 0.5 µg (His)$_5$IκBα in 10 µl of 50 mM Tris (pH 7.6), 5 mM $MgCl_2$, 2.5 µM okadaic acid, 200 µM ATP and 5 µCi of [γ-$^{32}$P]ATP. Incubations were carried out at 30° C. for 30 min.

Dephosphorylation of IκBα Kinase Complex

Purified IκBα kinase (from gel filtration chromatography) was treated with MEKK1Δ in 50 mM Tris (pH 7.6), 5 mM $MgCl_2$, 2 mM ATP for 30 min at 30° C. MEKK1Δ-activated IκBα kinase was separated from ATP by centrifugal gel filtration on Sephadex G50 and subsequently incubated with or without calf intestinal alkaline phosphatase (CIP) in 50 mM Tris (pH 7.8), 0.1 mM EDTA for 30 min at 30° C. IκBα kinase was then separated from CIP and MEKK1Δ by chromatography on a Superdex 200 column and assayed for IκBα kinase activity in the absence or presence of MEKK1Δ.

[γ-$^{32}$P]ATP Labeling of IκBα Kinase Complex

Two nanograms of MEKK1Δ was incubated in 7 µl of 70 mM Tris (pH 7.6), 7 mM $MgCl_2$, 3.5 µM okadaic acid, and 140 µM ATP for 15 min at 30° C. Subsequently, purified IκBα kinase (from the second Mono Q chromatography step as described above) and 10 µCi of [γ-$^{32}$P]ATP in a total volume of 3 µl were added and the incubation continued at 30° C. for an additional 30 min. In control reactions, either MEKK1Δ or IκBα kinase was omitted.

Example 1

Ubiquitination of IκBα Requires UBC4 (FIG. 1)

HeLa cell cytoplasmic extracts were separated into fraction I and fraction II by monoQ chromatography. Each fraction alone (lanes 3 & 7) or in combination (lane 8) was assayed for ubiquitination of $^{35}$S-labeled IκBα. To determine whether recombinant yeast UBC4 could substitute for fraction I in the ubiquitination assay, UBC4 was assayed alone (lane 2) or in combination with fraction II (lane 4). As controls, a mock E. coli extract (lane 5) or recombinant yeast UBC3 (lane 6) was added together with fraction II. Both UBC4 and UBC3 form thioesters with $^{125}$I-ubiquitin.

Example 2

A High Molecular Weight Kinase Phosphorylates IκBα at Serines 32 and 36 (FIG. 2)

(A) Fractionation of IκBα kinase on Superdex-200. Fractions containing IBA kinase from monoQ chromatography were pooled and precipitated with 40% ammonium sulfate. The resuspended precipitate was loaded onto a Superdex-200 gel filtration column and fractions were tested for their ability to phosphorylate $^{35}$S-labeled IκBα (the generation of the slower migrating band, as indicated by p-IκBα). Lane 1, IκBα control; lane 2, no kinase fraction; lane 3, kinase fractions (pooled) from monoQ chromatography (Q); lane 4, 40% ammonium sulfate precipitate (Qa); lanes 5–13, fractions 17–25. No kinase activity was detected in fractions 26–36. The number 670 and 440 above the autoradiogram indicates approximate molecular masses. The band above p-IκBα is mono-ubiquitinated IκBα due to the presence of fraction I in the reaction.

(B) Re-chromatography of IκBα kinase on Superdex-200. IκBα kinase containing fractions from Superdex-200 (fraction 18–21, FIG. 2A) were re-applied to a monoQ column and eluted with a linear gradient from 150 mM to 400 mM NaCl. The active fractions were pooled, concentrated and then re-chromatographed on a Superdex-200 column. Lane 1, no kinase fraction; lane 2, kinase fractions (fraction 18–20) from the first Superdex-200 column (S1, FIG. 2A); lane 3, kinase fractions (fraction 24–26) from the second monoQ column (Q2); lanes 4–10, fractions 17–23 from the second Superdex-200 column.

(C) Phosphorylation of IκBα mutants. In vitro synthesized IκBα mRNAs encoding mutant proteins were translated in vitro and then tested for their ability to be phosphorylated by IκBα kinase. Lanes 1 & 2, wild type IκBα; lanes 3 and 4, S32A/S36A mutant IκBα; lanes 5 and 6, S32E/S36F mutant; lanes 7 and 8, ΔN mutant, lanes 1, 3, 5, and 7, control reaction; lanes 2, 4, 6, and 8, incubation with the IκBα kinase. Phosphorylated IκBα is indicated by *.

(D) Phosphatase treatment of phosphorylated IκBα. $^{35}$S-IκBα was phosphorylated with the IκBα kinase, immunoprecipitated with antisera against the C-terminus of IκBα (c-21), and then incubated with (lanes 2, 4 and 6) or without (lane 1, 3 and 5) phosphatase (CIP). The samples were analyzed by 9% SDS-PAGE. Lanes 1 and 2, wild type IκBα (no epitope tags); lanes 3 and 4, IκBα tagged with the Flag epitope at the N-terminus; lanes 5 and 6, S32A/S36A (also with Flag epitope).

(E) Thrombin treatment of phosphorylated IκBα. The immunoprecipitates shown in 2D above were digested with thrombin and the supernatants containing the N-terminal fragments analyzed on 16.5% Tris-tricine polyacrylamide gel. The assignments of lanes are the same as FIG. 2D.

Example 3

Phosphorylation of IκBα Requires UBC4/UBC5 (FIG. 3)

(A) Phosphorylation of IκBα requires fraction I. $^{35}$S-labeled IκBα was phosphorylated by IκBα kinase in reaction mixtures containing (lanes 2 and 5) or lacking (lanes 1, 3 and 4) fraction I. Lanes 1 and 2, iκBα mutant S32A/S36A; lanes 3–5, wild type IκBα. In lanes 1 and 3, IκBα kinase was not added to the reaction.

(B) Phosphorylation of IκBα requires UBC4/UBC5. $^{35}$S-labeled IκBα was incubated with IκBα kinase in a reaction mixture containing purified recombinant UBC4 (yeast, lane 3) or purified GST-UBC5 (human, lane 4), or no E2 (lane 2). In lane 1, no IκBα kinase was added to the reaction.

(C) Only functional UBC4/UBC5 stimulates the phosphorylation of IκBα. E2s purified from rabbit reticulocytes were tested for their ability to stimulate the phosphorylation of IκBα. These E2s include: $E2_{14K}$ (lane 2), $E2_{17K}$ (lane 3), $E2_{20K}$ (lane 4), $E2_{25K}$ (lane 5) and $E^2{}_{35K}$ (lane 6). Other E2s that were tested include: purified recombinant human UBC2 (lane 7), yeast UBC4 (lane 8), and human GST-UBC5 (μg, lane 9). In lanes 10 and 11, the active site mutants of human UBC5 were tested. C85A, the active site cysteine at residue 85 (C85) of UBC5 was substituted with alanine. C85S, C85 of UBC5 was changed to serine. No E2 was added in lane 1.

(D). Thioester assays of E2s. The E2s and E2 mutants shown in FIG. 3C were also tested for their ability to form thioesters with $^{125}$I -ubiquitin in the presence of E1.

(E) Dominant negative effect of UBCh5 mutants. Eight μg of C85A (lane 1), C85S (lane 2), or GST (lane 3) was added to IκBα phosphorylation reactions containing 0.4 μg of wild type UBCh5, and the phosphorylation of IκBα was analyzed by SDS-PAGE. The doublets above IκBα in lane 3 probably correspond to proteins phosphorylated at one or both serine residues at position 32and 36.

Example 4

Phosphorylation of IκBα Requires Ubiquitin (FIG. 4)

(A) Concentration-dependent stimulation of IκBα phosphorylation by ubiquitin. $^{35}$S-labeled IκBα was incubated with IκBα kinase in the presence of different concentrations of ubiquitin, and the phosphorylation of IκBα was analyzed on SDS-PAGE.

(B) Inhibition of ubiquitin-dependent phosphorylation of IκBα by methylated ubiquitin (MeUb). $^{35}$S-labeled IκBα was incubated with IκBα kinase in the presence of ubiquitin (lanes 2 and 3) or MeUb (lane 6). In lanes 4 and 5, ubiquitin (2.4 μM or 60 μM) was preincubated with E1 (0.1 μM) and UBC4 (1 μM) at 37° C. for 3 minutes to form an E2-Ub thioester. This mixture was then added to the phosphorylation reaction mixture containing $^{35}$S-labeled IκBα, IκBα kinase, and MeUb (40 μM). In lanes 7–8, the preincubation mixture contains MeUb (40 μM) instead of ubiquitin. The E2-MeUb thioester mixture was then added to the phosphorylation reaction mixture containing 2.4 μM (lane 7) or 60 μM (lane 8) of ubiquitin.

Example 5

Phosphorylation of IκBα Requires E1, but does not Require Okadaic Acid or Binding to RelA (FIG. 5)

(A) E1 requirement. $^{35}$S-labeled IκBα translated in a wheat germ extract was allowed to associate with recombinant RelA and then precipitated with anti-RelA antisera. The immune complex was used as a substrate for phosphorylation by IκBα kinase. All reactions contain ubiquitin and GST-UBCh5. Lane 1, no E1; lane 2, E1 added; lane 3, wheat germ extract added.

(B) Okadaic acid and RelA requirement. $^{35}$S-labeled IκBα was phosphorylated by IκBα kinase in a reaction mixture containing all necessary components except for the following subtractions: lane 1, no kinase; lane 3, no Re1A; lane 4, no okadaic acid (OA).

Example 6

IκBα Kinase is Activated by a Prior Ubiquitination Event (FIG. 6)

(A) Preincubation of IκBα kinase with ubiquitination enzymes and ubiquitin eliminates the lag phase in the phosphorylation of IκBα. $^{35}$S-labeled IκBα was incubated with IκBα kinase in the presence of E1, ubiquitin and UBC4. After 0, 3, 6, 10, and 20 minutes at 37° C. an aliquot of the reaction was analyzed by SDS-PAGE (lanes 1–5). In lanes 10–13, IκBα kinase was preincubated with E1, ubiquitin, and UBC4 in the presence of ATP at 37° C. for 10 min before the addition of $^{35}$S-labeled IκBα which initiated the phosphorylation reaction. In lanes 6–9, ubiquitin was omitted from the preincubation mixture but added together with $^{35}$S-labeled IκBα. The doublets above IκBα probably represent phosphorylation at one or both serine residues at position 32 and 36.

(B) Kinetics of IκBα phosphorylation. Phosphorylated IκBα (P-IκBα) shown in FIG. 6A was quantitated by PhosphorImager analysis, and expressed as the percentage of IκBα converted to P-IκBα. Open circle, no preincubation; close circle, preincubation in the presence Of IκBα kinase and ubiquitin; open triangle, preincubation in the absence of IκBα kinase; close triangle, preincubation in the absence of ubiquitin; open square, no ubiquitination enzymes or ubiquitin in the reaction.

Example 7

Ubiquitination of IκBα Kinase Complex (FIG. 7)

(A) Formation of high molecular weight ubiquitin conjugates in the presence of UBC4 and IκBα kinase. IκBα kinase (2 μl per 10 μl reaction) was incubated with E1 (80 nM), UBC4 (2.5 μM) and $^{125}$I-labeled ubiquitin (28 μM, 1.6×10$^6$ cpm/nmol) in the presence of an ATP regenerating system. After 0, 3, 6, 10, 20, and 40 minutes at 37° C. (lanes 1–6), the reaction was quenched and analyzed by SDS-PAGE (5% stacking gel, 9% separating gel). In lanes 7–11, the ubiquitination reactions were carried out at 37° C. for 45 minutes in the presence or absence of UBC4 or IκBα kinase as shown in the figure. In lane 11, MeUb (0.15 mM) was added to the reaction. In lanes 2, 3 and 4, free ubiquitin ran off the gel. NS, nonspecific bands.

(B) Kinetics of IκBα kinase ubiquitination. The high molecular weight conjugates on the top of the gel shown in (A, lanes 1–6) were quantitated by PhosphorImager analysis, and expressed as a function of time.

Example 8

Figure 9:
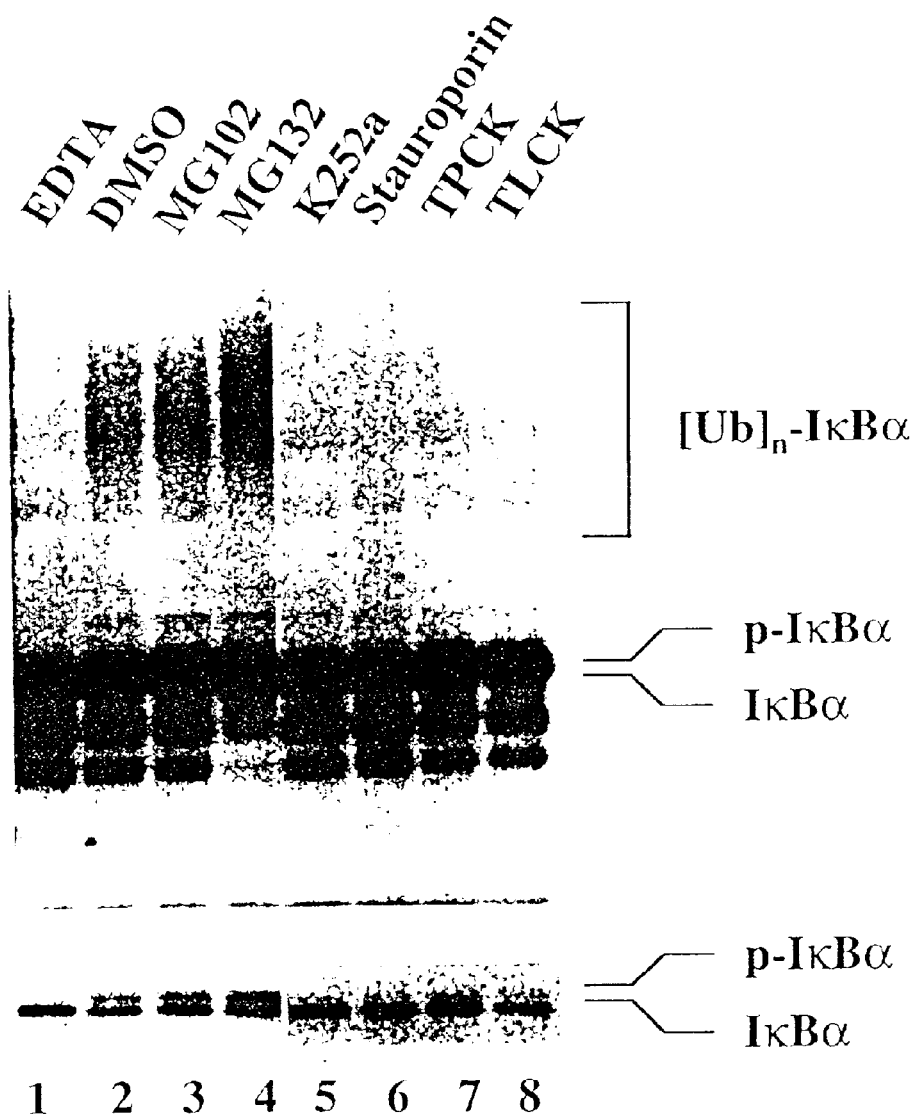
FIG. 9. Representation of an autoradiograph of an SDS-PAGE gel demonstrating that staurosporine and its analog K252a inhibit phosphorylation and ubiquitination of IκBα in HeLa cell extracts.

Staurosporine and its Analogue K252a Inhibit the Phosphorylation and Ubiquitination of IκBα in HeLa Cell Extracts (FIG. 9)

$^{35}$S-labeled IκBα was synthesized by in vitro translation, and used as a substrate for phosphorylation (bottom panel, short exposure) and ubiquitination (top panel, long exposure) assays in HeLa cell cytoplasmic extracts in the presence of okadaic acid (Chen et al., *Genes and Dev.* 9:1586–1597 (1995)). Various agents were included in the reaction to test their ability to inhibit the phosphorylation and ubiquitination of IκBα. Lane 1: EDTA (40 mM); lane 2: DMSO; lane 3: MG102 (50 μM) (Ac-L-Leu-L-Leu-L-Met-H); lane 4: MG132 (50 μM) (Cbz-L-Leu-L-Leu-L-Leu-H); lane 5: K252a (10 μM) (Calbiochem; Kase, H., et al., Biochem. Biophys. Res. Commun. 142:436 (1987); lane 6: Staurosporine (10 μM) (Calbiochem; Tomaoki, T., et al., Biochem. Biophys. Res. Commun. 135:397 (1986)); lane 7: TPCK (50 μM) (N-tosyl-L-phenylalanine chloromethyl ketone); lane 8: TLCK (50 μM) (Nα-p-tosyl-L-lysine chloromethyl ketone). TPCK and TLCK are alkylating agents that have previously been shown to inhibit the phosphorylation and degradation of IκBα in vivo (Beg et al., Mol. Cell. Biol. 13:3301–3310 (1993); Henkel et al., Nature 365:182–185 (1993); Sun et al., Science 259:1912–1915 (1993)). Staurosporine and K252a inhibit the activation of NF-κB in vivo by several agonists, including PMA and ionomycin, TNF-α, and LPS. K252a also inhibits the phosphorylation of IκBα by partially purified IκBα kinase.

Example 9

IκBα Kinase Activity is Inducible and is Correlated with JNK Activity (FIG. 10)

(A) HeLa cells were treated with TNF-α for the indicated times, and cytoplasmic extracts prepared by the rapid lysis procedure. Extracts (14 μg) were then subjected to 10% SDS-PAGE, transferred to nitrocellulose membrane, and probed with anti-IκBα antibodies. The positions of unphosphorylated (IκBα) and phosphorylated (P-IκBα) IκBα are indicated to the left. Molecular weight marker (in kilodaltons) is indicated to the right (B) HeLa cells were treated with TNF-α. for the indicated times, and cytoplasmic extracts prepared by the rapid lysis procedure. Extracts (9 μg) were then incubated with $^{35}$S-labeled IκBα in the absence or presence of 6 μM okadaic acid for 1 hr at 30° C. Reaction products were subjected to 9% SDS-PAGE and analyzed by autoradiography. The positions of unphosphorylated (IκBα) and phosphorylated (P-IκBα) IκBα are indicated to the left.

(C) HeLa cells were either mock or TNF-α (5-min) treated, and cytoplasmic extracts prepared by the rapid lysis procedure. Extracts (8 μg) were then incubated with $^{35}$S-labeled wild-type (WT) or mutant (S32A/S36A, M)IκBα, or wild-type (WT) or mutant (S63A/S73A, M) c-Jun for 0 or 60 min at 30° C. in the presence of 2.5 μM okadaic acid. Reaction products were subjected to 10% SDS-PAGE and analyzed by autoradiography. Molecular weight markers (in kilodaltons) are indicated to the left. The positions of unphosphorylated (cJun) and phosphorylated (P-cJun) c-Jun are indicated to the right; those for IκBα are indicated to the left.

(D) HeLa cell S100 extracts (18 μg) were incubated with $^{35}$S-labeled wild-type (WT) or mutant (S32A/S36A, M) IκBα, or wild-type (WT) or mutant (S63A/S73A, M) c-Jun for 0 or 60 min at 30° C. in the presence of 2.5 μM okadaic acid. Reaction products were subjected to 10% SDS-PAGE and analyzed by autoradiography. Molecular weight markers (in kilodaltons) are indicated to the left.

Example 10

MEKK1 Activates NF-κB in Vivo (FIG. 11)

(A) HeLa cells were transfected with 3 μg of (PRDII)$_2$CAT, (PRDIV)$_6$CAT or –110IFN-βCAT, 2 μg pCMV-lacZ, and 4 μg of pCMV5-MEKK1 of pcDNA3. Twenty-six to 28 hr posttransfection, cells in one well were infected with Sendai virus for 15 hr. All cells were harvested 41 to 43 hr posttransfection. CAT activities were normalized to protein concentrations of cell extracts. Shown are the averages and standard deviations from three independent experiments.

(B and C) HeLa (B) and L929(C) cells were transfected with 3 μg of (PRDII)$_2$CAT, 2 μg pCMV-lacZ, and 4 μg of pcDNA3-FlagMEKK1Δ (K432M) or pcDNA3. Forty to 41 hr posttransfection, some cells were treated with 20 ng/ml mouse TNF-α (Boehringer) for 8 hr. All cells were harvested 48 to 49 hr posttransfection. CAT activities were normalized to those for β-galactosidase. Shown are the averages and standard deviations from (B) one experiment performed in triplicate or (C) three independent experiments.

(D) L929 cells were transfected with 3 μg of (CRE)$_6$CAT, 2 μg pCMV-lacZ, and 4 μg of pcDNA3-FlagMEKK1Δ (K432M) or pcDNA3. Forty to 41 hr posttransfection, some cells were treated with 1 mM 8-Br-cAMP for 8 hr. All cells were harvested 48 to 49 hr posttransfection. CAT activities were normalized to those for β-galactosidase. Shown are the aveages and standard deviations from three independent experiments.

Example 11

Figure 12:
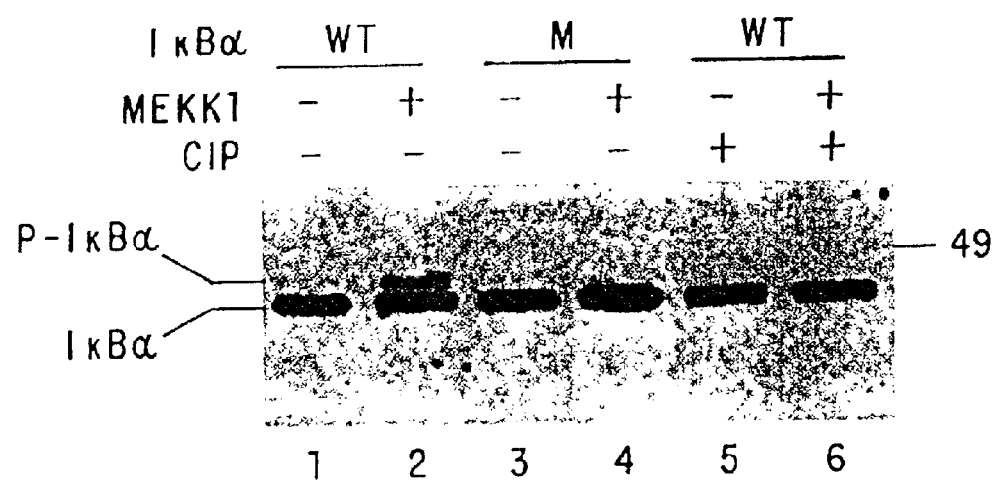
FIG. 12. Representation of an autoradiograph of an SDS-PAGE gel demonstrating that MEKK1 induces site specific phosphorylation of IκBα.

MEKK1 Activation of NF-κB is Through Site-Specific Phosphorylation of IκBα (FIG. 12)

HeLa cells were transfected with 0.3 μg of expression vectors for wild-type (WT) (pCMV4-Flag IκBα) or mutant (M) (pCMV4-Flag IκBα [S32A/S36A]) IκBα, 3 μg of pCMV5-MEKK1 of pCMV5, and 3 μg of SP72. Forty-one hr posttransfection, epitope-tagged IκBα was immunoprecipitated, and some samples were treated with calf intestinal alkaline phosphatase (CIP). All samples were then subjected to 10% SDS-PAGE, transferred to nitrocellulose membrane, and probed with anti-IκBα antibodies.

Example 12

MEKK1 Directly Activates the IκBα Kinase (FIG. 13)

(A) Uninduced HeLa cell cytoplasmic extracts (2 μg) prepared by the rapid lysis procedure were incubated with $^{35}$S-labeled wild-type (WT) or mutant (S32A/S36A, M)IκBα, or wild-type (WT) or mutant (S63A/S73A, M) c-Jun in the absence or presence of 20 ng MEKK1Δ for 1 hr at 30C in the presence of 2.5 μM okadaic acid. An additional incubation (lane 1) contained 20 ng MEKK1Δ and $^{35}$S-labeled IκBα in the absence of extract. Reaction products were subjected to 10% of SDS-PAGE and analyzed by autoradiography. Molecular weight markers (in kilodaltons) are indicated to the left.

(B) Uninduced HeLa cell cytoplasmic extracts (2 μg) prepared by the rapid lysis procedure were incubated with $^{35}$S-labeled IκBα in the absence or presence of 20 ng MEKK1Δ and/or 2.5 μM okadaic acid for 1 hr at 30° C. Reaction products were subjected to 10% SDS-PAGE and analyzed by autoradiography.

(C) Purified IκBα kinase was incubated with wild-type (WT), mutant (S32A/S36A) (M), or immunoprecipitated wild-type (IP) $^{35}$S-labeled Flag IκBα in the absence or presence of 20 ng wild-type (WT) or mutant (K432M) (M) MEKK1Δ, or 0.9 μg GST-Ubc5+0.5 mg/ml ubiquitin for 1 hr at 30° C. in the presence of 2.5 μM okadaic acid. An additional incubation (lane 1) contained 20 ng MEKK1Δ and $^{35}$S-labeled Flag IκBα in the absence of IκBα kinase.

Reaction products were subjected to 10% SDS-PAGE and analyzed by autoradiography. In lane 8, additional bands at higher molecular weights than phosphorylated IκBα represent ubiquitinated IκBα species, owing to the presence of ubiquitination components (Chen et al., 1995, 1996).

(D) Purified IκBα kinase in the absence or presence of 5, 10, or 20 ng MEKK1Δ was incubated with $^{35}$S-labeled Flag IκBα for 1 hr at 30° C. in the presence of 2.5 µM okadaic acid. Reaction products were subjected to 10% SDS-PAGE and analyzed by autoradiography.

Example 13

The MEKK1-Inducible IκBα Kinase is a High Molecular Weight Complex (FIG. 14)

HeLa cell cytoplasmic extracts were fractionated as described in Experimental Procedures and then chromatographed on (A and B) a Superdex-200 gel filtration column followed by a (C and D) Mono-Q ion exchange column. Fractions were assayed for IκBα kinase activity with $^{35}$S-labeled Flag IκBα in the presence of either (A and C) ubiquitination components or (B and D) 10 ng MEKK1Δ for 1 hr at 37° C. in the presence of 3 µM okadaic acid. Reaction products were subjected to 9% SDS-PAGE and analyzed by autoradiography. The numbers 670 and 400 in (A) and (B) indicate elution positions of molecular weight standards (in kilodaltons).

Example 14

MEKK1 is a Selective Activator of the IκBα Kinase (FIG. 15)

(A) MEKK1Δ (10 ng), CKII (0.35 ng, 250 mU, New England Biolabs PKA (0.8 ng, 1 mU, New England Biolabs),and PKCζ (15 ng. Pan Vera), either alone or in combination with purified IκBα kinase, were incubated with $^{35}$S-labeled Flag IκBα for 30 min at 30° C. in the presence of 2.5 µM okadaic acid. An additional incubation (lane 2) contained purified IκBα kinase and $^{35}$S-labeled Flag IκBα. Reaction products were subjected to 10% SDS-PAGE and analyzed by autoradiography.

(B) Purified IκBα kinase, MEKK1Δ, CKII, PKA, and PKCζ in the amounts employed in (A) were incubated with 0.5 µg (His)$_6$ IκBα in the presence of [γ-$^{32}$P]ATP. Reaction products were subjected to 10% SDS-PAGE and analyzed by autoradiography. Relative kinase activities determined by phosphorimager analysis for the IκBα kinase, MEKK1Δ, CKII, PKA, and PKCζ are 1, 0.6, 2.2, 1.0, and 1.3 respectively.

Example 15

MEKK1 Activates the IκBα Kinase Complex by Phosphorylation (FIG. 16)

(A) MEKK1Δ-activated IκBα kinase was incubated with or without calf intestinal alkaline phosphatase (CIP, as indicated), and subsequently incubated with or without 12 ng MEKK1Δ (as indicated) and with $^{35}$S-labeled FlagIκBα for 60 min at 37° C. in the presence of 3 µM okadaic acid. Reaction products were subjected to 9% SDS-PAGE and analyzed by autoradiography. The doublet above the IκBα probably represents phosphorylation at one or both serines at positions 32 and 36.

(B) MEKK1Δ and purified IκBα kinase, either alone or in combination, were incubated in the presence of [γ-$^{32}$P]ATP. Reaction products were subjected to 8% SDS-PAGE and analyzed by autoradiography. Molecular weight markers (in kDA) are shown to the left. Dots indicate bands (approximately 200, 180, and 120 kDa) present when the IκBα kinase incubated with [γ-$^{32}$P]ATP in the absence of MEKK1Δ. Bracket indicates bands present when MEKK1Δ is incubated with [γ-$^{32}$P]ATP in the absence of the IκBα kinase, showing MEKK1Δ autophosphorylation.

Example 16

Figures 19A, 19B:
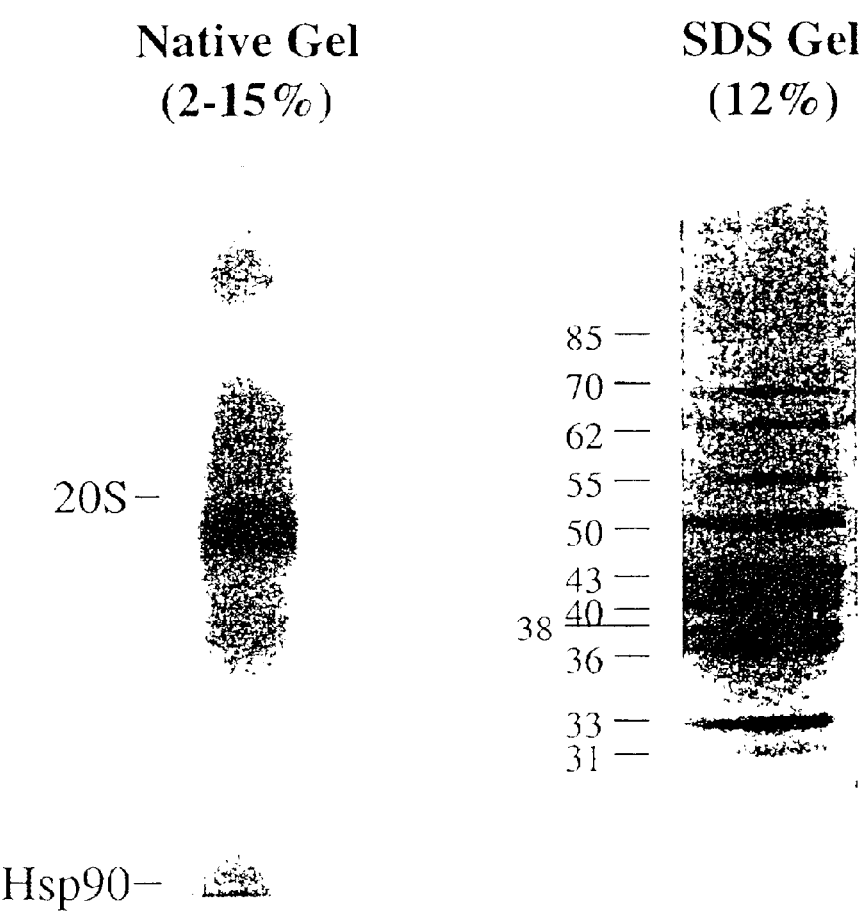
FIG. 19A is a representation of a silver stained native gel of a purified IκBα kinase fraction.
FIG. 19B is a representation of a silver stained SDS-PAGE gel of the same purified IκBα kinase fraction.

Subunit Composition of the Kinase Capable of Site-Specific Phosphorylation of IκBα (FIG. 19)

Purified IκBα kinase was obtained according to method C above. Fraction 24 from the last MonoQ column was run on 2–15% native gel at 4° C., 45 mV overnight and the protein contents analyzed by silver staining (FIG. 19, left page). Shown on the left are the protein markers: 20S: 700 kDa; HSP90: 90 kDa. The predominant band beneath the 20S marker on the left panel (Native gel) was excised and run on 12% SDS gel at 25° C., 200V. The subunit composition of the kinase complex was analyzed by silver staining (FIG. 19, right panel) shown on the left are the molecular weights of each individual subunit.

Example 17

Figure 20:
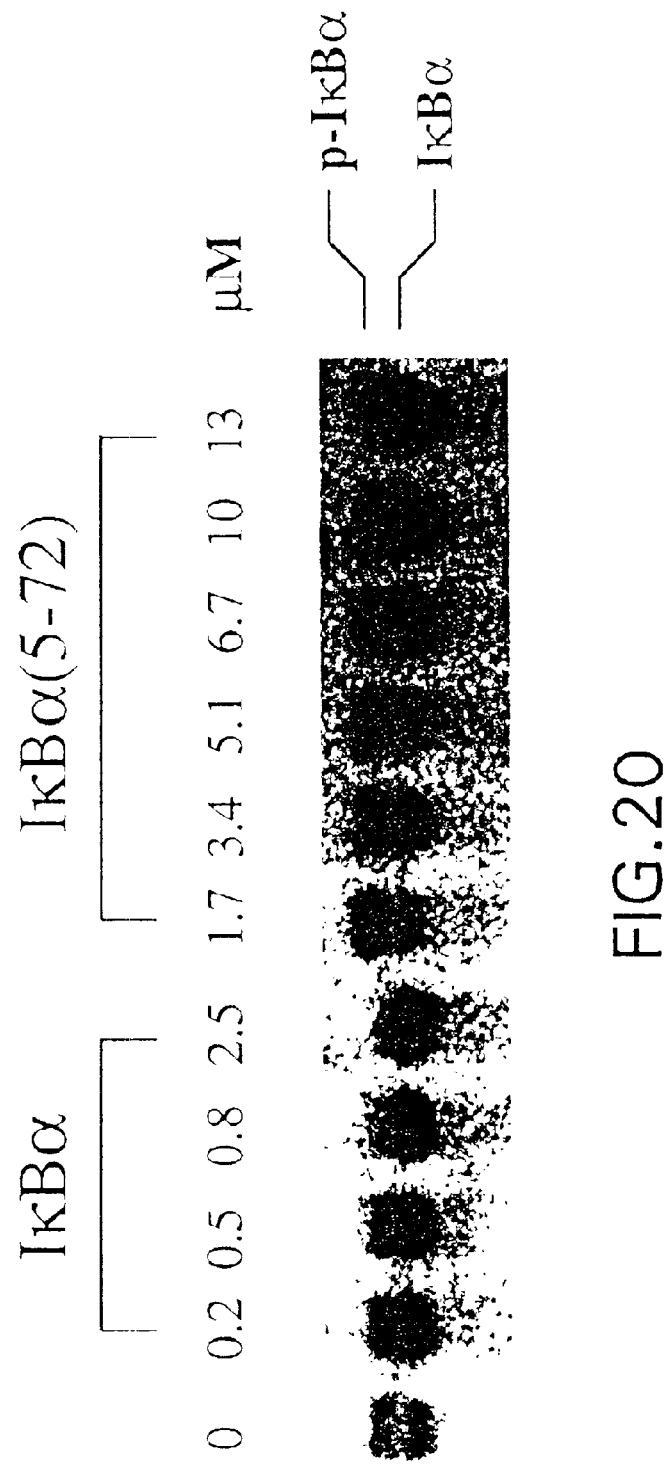
FIG. 20. Representation of an autoradiograph of an SDS-PAGE gel demonstrating inhibition of phosphorylation of $^{35}$S-IκBα by full-length IκBα and by IκBα (5–72), an N-terminal truncation mutant of IκBα.

A Polypeptide Inhibitor of IκBα Kinase (FIG. 20)

An N-terminal fragment (residues 5–72) of IκBα was expressed in *E. coli* as a recombinant protein containing a poly-histidine (His6) tag at the N-terminus. Protein purification was accomplished by nickel affinity chromatography. As a control, the full-length IκBα (SEQ ID NO:9; Haskill (1991) *Cell* 65:1281) was also expressed and purified in a similar fashion.

Recombinant full-length IκBα or IκBα (5–72) was added at indicated concentration to 10 µl of reaction mixture containing an ATP regenerating system (50 mM Tris at pH 7.6, 5 mM MgCl$_2$, 2 mM ATP, 10 mM phosphocreatine, 3.5 U/ml creatine phosphokinase, 0.6 U/ml inorganic pyrophosphatase), 60 µM Ubiquitin, 50 nM E1, 1 µM UBC4, 0.5 µl of in vitro translated $^{35}$S- IκBα, 0.5 µl of IκBα kinase (fraction 19 from Superdex 200 column), and 3 µM okadaic acid. After incubation at 37° C. for 40 min., the reaction was quenched by the addition of SDS sample buffer, separated by electrophoresis on 9% SDS-polyacrylamide gel, and then analyzed by fluorography.

Example 18

Gel-Based IκBα Kinase Assay

HeLa cell extract was prepared by hypotonic lysing followed by 100,000× g centrifugation (S-100). Supernatant was collected and a 80% ammonium sulfate precipitation step was followed by dialysis against 20 mM Tris pH 7.6, 1 mM DTT. Cell extract was loaded onto Mono-Q anion exchange column at pH 7.6 and the kinase was eluted with a 300 mM KCl step gradient. Eluate was further concentrated with 40% ammonium sulfate, then dialyzed against 50 mM HEPES pH 7.6, 1 mM DTT. This partially purified kinase was activated by incubating with 250 nM E1, 750 nM UBC4, 60 µM ubiquitin, 2.5 mM ATP regeneration system, 3 µM okadaic acid, for 90 minutes at 37° C. Peptides from 10 mM stock were added to a nominal concentration of 1 mM and allowed to equilibrate for 30 minutes. In vitro translated IκBα labeled with [$^{35}$S] was added for 20 minutes and the phosphorylation reactions were quenched with 5×

SDS sample buffer, then chromatographed on 9% reducing SDS-PAGE. For $IC_{50}$ determination, peptides were serially diluted in the range of 1 mM-1 µM prior to assaying. All quantification of phosphorylation activity by this gel-shift assay was performed with a phosphorimager. The Mono-Q anion exchange column, Superose-6 size-exclusion beads were obtained from Pharmacia, Upsala, Sweden.

Example 19

ATP Km Determination

Michaelis constant for ATP was determined by first activating the partially purified kinase either with components of the ubiquitination system for 90 minutes or with 30 nM MEKK1Δ for 30 minutes at 37° C. using 2.5 mM MgATP. Samples were then passed through desalting Biospin-6 columns (Biorad, Hercules, Calif.). Various concentrations of ATP were added back to the desalted kinase sample together with in vitro translated [$^{35}$S] IκBα substrate for 20 minutes before quenching and chromatographing on SDS-PAGE. By this analysis, the Km of IκBα kinase for ATP was determined to be approximately 300 µM.

Example 20

Amino Acid and Nucleic Acid Sequences of p40 and p50

Each protein subunit shown in FIG. 19 was excised from the polyacrylamide gel and digested with trypsin in situ. The digested peptides were extracted, separated by HPLC, and microsequenced by tandem mass spectrometry (MS/MS) in the Harvard Microchemistry Facility. The peptide sequences of p50 and p40 are shown in FIG. 21.

In FIG. 21, an asterisked residue cannot be unambiguously differentiated within its isobaric pair in mass spectrometric sequencing (Confidence: A=High; [A]=Probable/Reasonable; (A)=Possible/Low).

The peptide sequences shown in FIG. 21 were used to search the public EST database, and matches are shown in FIGS. 22A and B. FIG. 22A shows the nucleotide sequence whose translated amino acid sequence contains pep2 (LQEVIETLLSLEK). FIG. 22B represents the nucleotide sequence whose translated amino acid sequence contains pep4 (TYHALSNLPK).

The nucleic acid sequences shown in FIGS. 22A and 22B can be radiolabeled and used as probes to obtain the full length clone of p50 and p40, respectively, by screening a cDNA library (i.e., HeLa cell cDNA library, for example, see Chen and Pickart, *J. Biol. Chem.* 265: 21835–21842 (1990)).

Example 21

Figure 23:
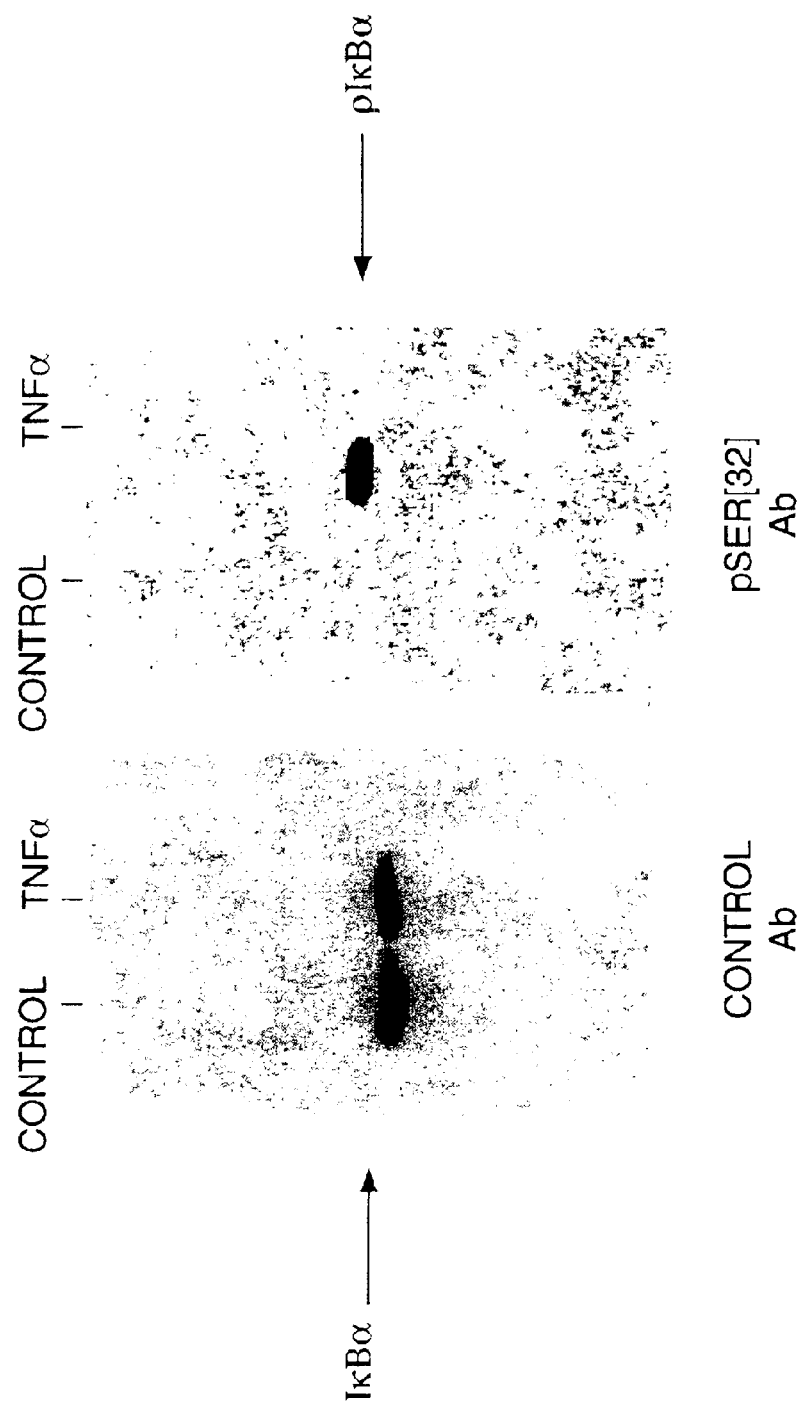
FIG. 23. Representation of a Western blot of an SDS-PAGE gel demonstrating that phosphorylated IκBα can be detected by Western blot analysis using an antibody specific for phosphoserine[32]-IκBα.

Western Blot Analysis of Endogenous IκBα Phosphorylation in TNF-α Stimulated HeLa Cells (FIG. 23)

HeLa cells were treated with TNF-α for 5 minutes then lysed by rapid dounce method. Samples were chromatographed on SDS-PAGE, transferred onto nitrocellulose membrane, then probed with either control IκBα antibody or with phosphoserine[32] specific IκBα antibody.

Example 22

Kinase Purification for ELISA Assays

IκBα kinase was prepared by first diluting S-100 HeLa cell extracts [1:10] with 50 mM HEPES pH 7.6 and 40% ammonium sulfate was added for 30 minutes on ice. Collected pellet was redissolved to a minimum volume, centrifuged, and filtered through a 0.22 µm filter. Sample was loaded onto a Superose-6 FPLC column equilibrated with 50 mM HEPES pH 7.6, 25 mM NaCl, 1 mM DTT, operated at 4° C. at 1 mL/min flow rate. Fractions were assayed for activity by the gel-shift assay. Active fractions peaked at ~700 kD were collected, pooled, and protein concentration was determined.

Example 23

ELISA-Based IκBα Kinase Assays

ELISA Scheme 1

Biotinylated peptide substrate at 500 µM was incubated with partially purified kinase alone, with 30 nM MEKK1Δ alone, or in combination for 2 hrs at 37° C. with 2.5 mM ATP, 10 mM DTT, 5 µM okadaic acid in the presence or absence of inhibitor. Kinase reactions were quenched by diluting [1:50] with PBS-BTE (PBS, 0.1% BSA, 0.05% Tween-20, 20 mM EDTA). Quenched reactions at 200 µL or phosphopeptide standards were added to Streptavidin pre-coated 96-well microplate and incubated for 2 hrs at 25° C. After three washes with PBS-T (PBS, 0.05% Tween-20), IκBα phosphoserine[32]-specific antibody (New England Biolabs, Beverly, Mass.) was added at [1:500] dilution in PBS-T for 2 hrs. After three washes, anti-rabbit gamma-chain specific monoclonal antibody conjugated with horseradish peroxidase diluted to [1:5000]with PBS-BTE was added for 1 hr. Color development was performed with o-phenylenediamine dihydrochloride (Sigma FAST o-PD) and signals were recorded at 450 nm. Alternatively, peroxidase reaction was quenched with 3 N HCl and signals were read at 492 nm.

When control primary antibody which recognizes all IκBα species was used, all samples containing biotinylated peptide substrate produced peroxidase activity as detected by the o-PD conversion. Activated kinase without any peptide or with non-biotinylated peptide gave background signals. However, when using specific phosphoserine[32] antibody for detection, only samples containing biotinylated peptide substrate with MEKK1 activated kinase produced positive signals. Furthermore, this MEKK1 dependent kinase activity can be fully inhibited by adding 10 µM K-252a to activated kinase prior to adding the biotinylated peptide substrate.

Reactibind Streptavidin coated 96-well plates, Reactibind Protein-A coated 96-well plates, streptavidin conjugated horseradish peroxidase were obtained from Pierce, Rockford, Ill. Anti-rabbit γ-chain specific monoclonal antibody conjugated with horseradish peroxidase, Sigma FAST o-phenylenediamine dihydrochloride substrate kit, were obtained from Sigma, St. Louis, Mo. 3,3',5,5'-tetramethylbenzidine (TMB) 1-Component peroxidase substrate, 1-Component Stop solution were obtained from Kirkegaard & Perry Laboratories, Gaithersburg, Md. Phosphatase inhibitors Okadaic acid potassium salt and Microcystin LR, kinase inhibitors Staurosporine and K-252a, all were obtained from Calbiochem, La Jolla, Calif.

Protein-A microplate was pre-blocked for 1 hr with 5% non-fat dry milk and 10 µM peptide 8 in PBS. Phosphoserine [32]-specific IκBα antibody diluted [1:400] with PBS-T at 100 µL was added for 2 hrs. Phosphopeptide calibration standards (100–0.1 nM) serially diluted into PBS-BTE buffer solution containing 1 µM biotinylated peptide substrate were added and incubated for 2 hrs. Following 3 washes with PBS-T, 100 µL of Streptavidin conjugated horseradish peroxidase at 0.5 µg/mL was added for 1 hr.

After 5 washes with PBS-T and once with water, 100 μL TMB substrate was added for 10 minutes at room temperature. Color development was stopped by adding 100 μL of 0.18 M H₂SO₄. Signals were recorded at 450 nm. Calibration curve standard samples were fitted with a semi-log linear regression for phosphopeptide range 0.25–20 μM (pane A), or with 4-parameter linear regression for the phosphopeptide range 0.1–100 nM (panel B).

ELISA scheme 2—Kinase at 50 μg/mL was activated by preincubation with 100 nM MEKK1Δ, 2 mM MgATP, 10 mM DTT, 2.5 μM phosphatase inhibitors, for 20 minutes at 37° C. Compounds at various concentrations were added for 30 minutes at 37° C. Biotinylated peptide substrate at 10 μM was added for another 30 minutes before quenching with 9× volumes of PBS-BTE. Quenched samples at 100 μL were added to each well of Protein-A 96-well plate which had been pre-blocked for 1 hr with 5% non-fat dry milk and 10 μM 8 peptide in PBS, and coated for 2 hrs with IκBα phosphoserine[32]-specific antibody diluted [1:400] with PBS-T. Kinase reactions or phosphopeptide calibration standards (0.1–100 nM) were allowed to incubate for 2 hrs. Following 3 washes with PBS-T, 100 μL of Streptavidin conjugated horseradish peroxidase diluted to 0.5 μg/mL with PBS-BTE was added for 1 hr. After 5 washes with PBS-T and once with water, 100 μL TMB substrate was added for <15 minutes at room temperature. Color development was stopped by adding 100 μL of 1-Component stop solution or 0.18 M H₂SO₄. Signals were recorded at 450 nm. Calibration curve standard samples were fitted with a semi-log linear regression for phosphopeptide with the range of 0.2–20 nM.

$$y = m^*(\log(x)) + D$$

Alternatively, a dose-response 4-parameter linear regression was used for 0.05–100 nM phosphopetide range.

$$y = \frac{(A - D)}{1 + \left(\frac{x}{C}\right)^B} + D \quad (1)$$

Phosphorylation levels can be correlated with absorbance values with proper background substracted.

Specificity of IκBα phosphoserine[32] antibody HeLa cells when treated with TNF-α induced okadaic-acid sensitive phosphorylation of IκBα within 5 minutes of treatment. This event could be observed with the gel-shift assay when cells were lysed by the rapid dounce method. Samples of TNF-α stimulated HeLa cells were analyzed by Western blot analysis using either a control antibody or an affinity-purified phosphoserine[32] specific antibody (FIG. 23). With control antibody, endogenous IκBα from both non-stimulated and TNF-α stimulated cells reacted to the antibody. However, with phosphoserine[32] specific antibody, only TNF-α stimulated cells showed an IκBα species reactive to the antibody.

Example 24

Figure 24:
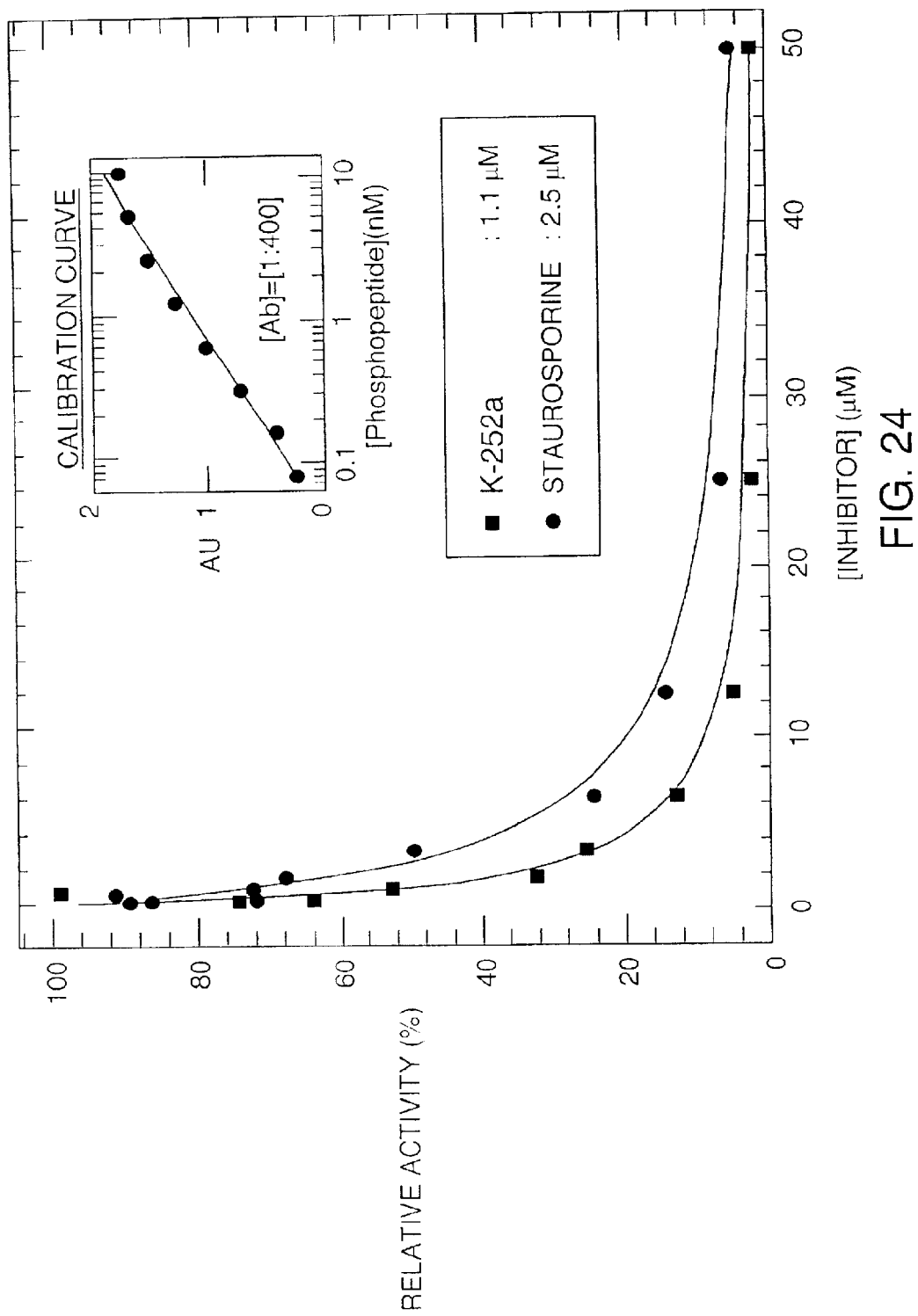
FIG. 24. Graphical representation of IκBα kinase activity as a function of inhibitor concentration, from which it can be determined that the $IC_{50}$ for staurosporine is 2.5 μM and the $IC_{50}$ for K252a is 1.1 μM.

Inhibition Profiles of Staurosporine and K-252a Against IκBα Kinase (FIG. 24)

Kinase purified by SEC was incubated with 100 nM MEKK1Δ for 20 minutes at 37° C., inhibitors at various concentrations were added for 30 minutes, then 10 μM biotynylated peptide substrate was added for 30 minutes at 37° C. before quenching by adding 9× volumes of PBS-BTE buffer. Samples and standards (0.1–10 nM at 100 μL were added for 2 hrs to pre-blocked Protein-A plate coated for 2 hrs with [1:400] antibody (see ELISA scheme 2 in Example 23). Streptavidin conjugated peroxidase was added and color development was performed with TMB and stopped with 100 μL of 0.18 M H₂SO₄. Phosphorylation level was calculated from a calibration curve, showing $IC_{50}$ values of 1 μM and 3 μM for K-252a and staurosporine, respectively (FIG. 24).

Abbreviations Used—ELISA: Enzyme linked immunosorbent assay; TMB: 3,3',5,5'-tetramethylbenzidine; o-PD: phenylenediamine dihydrochloride; HEPES: N-[2-Hydroxyethyl]piperazine-N'-[2-ethanesulfonic acid]; DT: dithiothrietol; ATP: Adenosine triphosphate; SDS-PAGE: sodium dodecyl sulfate—polyacrylamide gel electrophoresis; EDTA: ethylenediamine tetra-acetic acid; TFA: trifluoroacetic acid; PBS: phosphate buffered saline; HPLC: High performance liquid chromatography; FPLC: Fast protein liquid chromatography; SEC: size-exclusion chromatography.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A purified kinase which phosphorylates IκBα (SEQ ID NO:9) at seine residues 32 and 36, the kinase being a complex of approximately 700 kDa molecular weight as determined by gel filtration chromatography or size exclusion chromatography.

2. The kinase according to claim 1, wherein the kinase is purified by chromatographic purification of cell extracts.

3. The kinase according to claim 2, wherein the extracts are cell cytoplasmic extracts.

4. The kinase according to claim 2, wherein the chromatographic purification comprises ion-exchange chromatography and size exclusion chromatography.

5. A method for identifying an agonist for the activity of a kinase which phosphorylates IκBα (SEQ ID NO:9) at serine residues 32 and 36, the method comprising:

(a) contacting a sample comprising a purified kinase which phosphorylates IκBα at serine residues 32 and 36, the kinase being a complex of approximately 700 kDa molecular weight as determined by gel filtration chromatography or size exclusion chromatography, IκBα, and a test substance under conditions in which the kinase phosphorylates IκBα; and (b) measuring the phosphorylation of IκBα, wherein an increase in the amount of phosphorylation of IκBα in the presence of the test substance compared to the phosphorylation in the absence of the test substance indicates that the test substance is an agonist of the kinase.

6. A method for identifying an antagonist for the activity of a kinase which phosphorylates IκBα (SEQ ID NO:9) at serine residues 32 and 36, the method comprising:

(a) contacting a sample comprising a purified kinase which phosphorylates IκBα at serine residues 32 and 36, the kinase being a complex of approximately 700 kDa molecular weight as determined by gel filtration chromatography or size exclusion chromatography, IκBα, and a test substance under conditions in which the kinase phosphorylates IκBα; and (b) measuring the phosphorylation of IκBα, wherein a decrease in the amount of phosphorylation of IκBα in the presence of the test substance compared to the phosphorylation in the absence of the test substance indicates that the test substance is an antagonist of the kinase.

* * * * *

SEQUENCE LISTING

<160> NUMBER OF SEQ ID NOS: 9

<210> SEQ ID NO 1
<211> LENGTH: 36
<212> TYPE: DNA
<213> ORGANISM: Artificial Sequence
<220> FEATURE:
<223> OTHER INFORMATION: primer

<400> SEQUENCE: 1
ttgtgacctc aggatatcga gagcaatact tccatt                        36

<210> SEQ ID NO 2
<211> LENGTH: 35

```
<212> TYPE: DNA
<213> ORGANISM: Artificial Sequence
<220> FEATURE:
<223> OTHER INFORMATION: primer

<400> SEQUENCE: 2
ttgtgacctc aggatatcga gagaaatact tccat                                35

<210> SEQ ID NO 3
<211> LENGTH: 7
<212> TYPE: PRT
<213> ORGANISM: homo sapiens
<220> FEATURE:
<221> NAME/KEY: VARIANT
<222> LOCATION: 1,5
<223> OTHER INFORMATION: Xaa = Leu or Ile

<400> SEQUENCE: 3

Xaa Tyr Val Glu Xaa Glu Arg
 1               5

<210> SEQ ID NO 4
<211> LENGTH: 13
<212> TYPE: PRT
<213> ORGANISM: homo sapiens
<220> FEATURE:
<221> NAME/KEY: VARIANT
<222> LOCATION: 1,5,8,9,11
<223> OTHER INFORMATION: Xaa = Leu or Ile
<220> FEATURE:
<221> NAME/KEY: VARIANT
<222> LOCATION: 2
<223> OTHER INFORMATION: Xaa = Gln or Lys

<400> SEQUENCE: 4

Xaa Xaa Glu Val Xaa Glu Thr Xaa Xaa Ser Xaa Glu Lys
 1               5                  10

<210> SEQ ID NO 5
<211> LENGTH: 9
<212> TYPE: PRT
<213> ORGANISM: homo sapiens
<220> FEATURE:
<221> NAME/KEY: VARIANT
<222> LOCATION: 1,7
<223> OTHER INFORMATION: Xaa = Leu or Ile

<400> SEQUENCE: 5

Xaa Phe Thr Thr Met Glu Xaa Met Arg
 1               5

<210> SEQ ID NO 6
<211> LENGTH: 10
<212> TYPE: PRT
<213> ORGANISM: homo sapiens

<400> SEQUENCE: 6

Thr Tyr His Ala Leu Ser Asn Leu Pro Lys
 1               5                  10

<210> SEQ ID NO 7
<211> LENGTH: 404
<212> TYPE: DNA
<213> ORGANISM: homo sapiens
<220> FEATURE:
<221> NAME/KEY: unsure
<222> LOCATION: (1)...(404)
<223> OTHER INFORMATION: n = any nucleotide
```

<400> SEQUENCE: 7

```
gggtgacgag tggtggccga agcaggggga cagcaaggga cgctcaggcg gggaccatgg    60
cggacggcgg ctcggagcgg gctgacgggc gcatcgtcaa gatggaggtg gactacagcg   120
ccacggtgga tcagcgccta cccgagtgtg cgaagtatgc caaggaagga agacttcaag   180
aagtcattga aacccttctc tctctggaaa agcagactcg tactgcttcc gatatggtat   240
cgacatcccg tatcttagtt gcagtagtga agntgtgcta tgaggctaaa gaatgggatt   300
tacttaatta aaaatattat tgcttttgt ccaaaaggcg gagtcaagtt aaaaacaagc    360
tagttgacaa aaaatggatt naacagttgc tgtnacttat tgtt                    404
```

<210> SEQ ID NO 8
<211> LENGTH: 323
<212> TYPE: DNA
<213> ORGANISM: homo sapiens

<400> SEQUENCE: 8

```
ataccaagag gtaccaggaa gcattgcatt tgggttctca gctgctgcgg gagttgaaaa    60
agatggacga caaagctctt ttggtggaag tacagctttt agaaagcaaa acataccatg   120
ccctgagcaa cctgccgaaa gcccgagctg ccttaacttc ttctcgaacc acagcaaatg   180
ccatctactg ccccctaaat tgcaggccac cttggacatg cagtcgggta ttatccatgc   240
agcagaagag aaggcttgaa actcgtactc atacttctat gaggcattta gggtatgact   300
catcgacagc ccaaggcatc aca                                           323
```

<210> SEQ ID NO 9
<211> LENGTH: 317
<212> TYPE: PRT
<213> ORGANISM: Homo sapiens

<400> SEQUENCE: 9

```
Met Phe Gln Ala Ala Glu Arg Pro Gln Glu Trp Ala Met Glu Gly Pro
  1               5                  10                  15

Arg Asp Gly Leu Lys Lys Glu Arg Leu Leu Asp Asp Arg His Asp Ser
             20                  25                  30

Gly Leu Asp Ser Met Lys Asp Glu Glu Tyr Glu Gln Met Val Lys Glu
         35                  40                  45

Leu Gln Glu Ile Arg Leu Glu Pro Gln Glu Val Pro Arg Gly Ser Glu
     50                  55                  60

Pro Trp Lys Gln Gln Leu Thr Glu Asp Gly Asp Ser Phe Leu His Leu
 65                  70                  75                  80

Ala Ile Ile His Glu Glu Lys Ala Leu Thr Met Glu Val Ile Arg Gln
                 85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190
```

-continued

```
His Gly Tyr Leu Gly Ile Val Glu Leu Leu Val Ser Leu Gly Ala Asp
        195             200             205

Val Asn Ala Gln Glu Pro Cys Asn Gly Arg Thr Ala Leu His Leu Ala
    210             215             220

Val Asp Leu Gln Asn Pro Asp Leu Val Ser Leu Leu Leu Lys Cys Gly
225             230             235             240

Ala Asp Val Asn Arg Val Thr Tyr Gln Gly Tyr Ser Pro Tyr Gln Leu
            245             250             255

Thr Trp Gly Arg Pro Ser Thr Arg Ile Gln Gln Leu Gly Gln Leu
            260             265             270

Thr Leu Glu Asn Leu Gln Met Leu Pro Glu Ser Glu Asp Glu Glu Ser
        275             280             285

Tyr Asp Thr Glu Ser Glu Phe Thr Glu Phe Thr Glu Asp Glu Leu Pro
    290             295             300

Tyr Asp Asp Cys Val Phe Gly Gly Gln Arg Leu Thr Leu
305             310             315
```